US012760070B2

(12) United States Patent
Pei et al.

(10) Patent No.: US 12,760,070 B2
(45) Date of Patent: *Oct. 13, 2026

(54) CYCLIC CELL PENETRATING PEPTIDES AND METHODS OF MAKING AND USING THEREOF

(71) Applicant: Ohio State Innovation Foundation, Columbus, OH (US)

(72) Inventors: Dehua Pei, Columbus, OH (US); Ziqing Qian, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/329,358

(22) Filed: Sep. 15, 2025

(65) Prior Publication Data

US 2026/0008816 A1 Jan. 8, 2026

Related U.S. Application Data

(63) Continuation of application No. 17/832,107, filed on Jun. 3, 2022, now Pat. No. 12,454,552, which is a continuation of application No. 16/462,920, filed as application No. PCT/US2017/063020 on Nov. 22, 2017, now Pat. No. 11,352,394.

(60) Provisional application No. 62/425,438, filed on Nov. 22, 2016.

(51) Int. Cl.

| | |
|---|---|
| ***C07K 7/64*** | (2006.01) |
| ***A61P 35/00*** | (2006.01) |
| ***C07K 14/00*** | (2006.01) |
| *A61K 38/00* | (2006.01) |
| *A61K 45/06* | (2006.01) |

(52) U.S. Cl.

CPC ................ *C07K 7/64* (2013.01); *A61P 35/00* (2018.01); *C07K 14/001* (2013.01); *A61K 38/00* (2013.01); *A61K 45/06* (2013.01); *C07K 2319/10* (2013.01)

(58) Field of Classification Search

CPC .... C07K 7/64; C07K 14/001; C07K 2319/10; A61P 35/00; A61K 38/00; A61K 45/06

See application file for complete search history.

(56) References Cited

U.S. PATENT DOCUMENTS

| | | | | |
|---|---|---|---|---|
| 5,523,308 | A | 6/1996 | Costanzo et al. | |
| 5,804,558 | A | 9/1998 | Lehrer et al. | |
| 6,864,355 | B1 | 3/2005 | May et al. | |
| 6,960,648 | B2 | 11/2005 | Bonny | |
| 7,850,949 | B2 | 12/2010 | Fang | |
| 8,901,071 | B2 | 12/2014 | O'Neil et al. | |
| 9,303,075 | B2 | 4/2016 | Brinkmann et al. | |
| 9,868,767 | B2 | 1/2018 | Pei et al. | |
| 10,626,147 | B2 | 4/2020 | Pei et al. | |
| 10,738,093 | B2 | 8/2020 | Qian et al. | |
| 11,225,506 | B2 | 1/2022 | Pei et al. | |
| 11,352,394 | B2 * | 6/2022 | Pei | A61K 45/06 |
| 11,878,046 | B2 | 1/2024 | Pei et al. | |
| 11,987,647 | B2 | 5/2024 | Pei | |
| 12,171,838 | B2 | 12/2024 | Pei et al. | |
| 12,454,552 | B2 * | 10/2025 | Pei | A61K 45/06 |
| 2002/0035243 | A1 | 3/2002 | Imfeld et al. | |
| 2002/0120100 | A1 | 8/2002 | Bonny | |
| 2003/0032594 | A1 | 2/2003 | Bonny | |
| 2004/0014669 | A1 | 1/2004 | Selsted et al. | |
| 2007/0041904 | A1 | 2/2007 | Jiang et al. | |
| 2008/0234183 | A1 | 9/2008 | Hallbrink et al. | |
| 2009/0186802 | A1 | 7/2009 | Alluis et al. | |
| 2010/0221235 | A1 | 9/2010 | Arranz | |
| 2010/0292148 | A1 | 11/2010 | Krippner et al. | |
| 2012/0016005 | A1 | 1/2012 | Samarsky et al. | |
| 2014/0294942 | A1 | 10/2014 | French et al. | |
| 2015/0297742 | A1 | 10/2015 | Strieker et al. | |
| 2016/0115202 | A1 | 4/2016 | Pei et al. | |
| 2016/0235807 | A1 | 8/2016 | Shailubhai | |
| 2016/0271216 | A1 | 9/2016 | Kemper et al. | |
| 2017/0190743 | A1 | 7/2017 | Pei et al. | |
| 2017/0355730 | A1 | 12/2017 | Pei et al. | |
| 2018/0030094 | A1 | 2/2018 | Pei et al. | |
| 2019/0282654 | A1 | 9/2019 | Pei et al. | |
| 2019/0284240 | A1 | 9/2019 | Pei et al. | |
| 2024/0158445 | A1 | 5/2024 | Pei et al. | |
| 2024/0173423 | A1 | 5/2024 | Pei | |
| 2024/0360174 | A1 | 10/2024 | Pei et al. | |
| 2024/0368227 | A1 | 11/2024 | Pei | |
| 2025/0090675 | A1 | 3/2025 | Pei et al. | |
| 2026/0001916 | A1 | 1/2026 | Pei | |
| 2026/0008812 | A1 | 1/2026 | Pei et al. | |

(Continued)

FOREIGN PATENT DOCUMENTS

| | | | |
|---|---|---|---|
| EP | 2420255 | A2 | 2/2012 |
| JP | 2010526091 | A | 7/2010 |

(Continued)

OTHER PUBLICATIONS

Bowie et al (Science, 1990, 247:1306-1310) (Year: 1990).*
Burgess et al (J. Cell Biol. 111:2129-2138, 1990) (Year: 1990).*
Lazar et al (Mol. Cell. Biol., 8:1247-1252, 1988) (Year: 1988).*
He et al, Molecules, 2019, 24, 1855, 1-34 (Year: 2019).*
Lu et al, International Journal of Molecular Sciences, 2016, 17, 561, 1-22]. (Year: 2016).*
Chen et al. Adv. Drug Deliv. Rev. 65:1357-1369, 2013). (Year: 2013).*

(Continued)

*Primary Examiner* — Sudhakar Katakam
(74) *Attorney, Agent, or Firm* — Knowles Intellectual Property Strategies, LLC

(57) ABSTRACT

Disclosed herein are peptides having activity as cell penetrating peptides. In some embodiments, the peptides can comprise a cell penetrating peptide moiety and beta-haripin turn creating moiety. In other embodiments, the peptides also comprise a cargo moiety.

10 Claims, 12 Drawing Sheets

Specification includes a Sequence Listing.

(56) References Cited

U.S. PATENT DOCUMENTS

| | | | |
|---|---|---|---|
| 2026/0008813 A1 | 1/2026 | Pei et al. |
| 2026/0070947 A1 | 3/2026 | Pei |
| 2026/0070948 A1 | 3/2026 | Pei et al. |
| 2026/0115301 A1 | 4/2026 | Pei et al. |
| 2026/0146063 A1 | 5/2026 | Pei et al. |

FOREIGN PATENT DOCUMENTS

| | | |
|---|---|---|
| WO | WO-2001052875 A1 | 7/2001 |
| WO | WO-2002031109 A2 | 4/2002 |
| WO | WO-2007055578 A1 | 5/2007 |
| WO | WO-2008134761 A2 | 11/2008 |
| WO | WO-2009098450 A2 | 8/2009 |
| WO | WO-2010072406 A1 | 7/2010 |
| WO | WO-2014053882 A1 | 4/2014 |
| WO | WO-2014086835 A1 | 6/2014 |
| WO | WO-2014190313 A2 | 11/2014 |
| WO | WO-2015051030 A2 | 4/2015 |
| WO | WO-2015179434 A1 | 11/2015 |
| WO | WO-2015179691 A2 | 11/2015 |
| WO | WO-2016054510 A1 | 4/2016 |
| WO | WO-2017109076 A1 | 6/2017 |
| WO | WO-2018098231 A1 | 5/2018 |

OTHER PUBLICATIONS

Verdine et al (Methods in Enzymology, 2012, vol. 503, 3-33) (Year: 2012).*

U.S. Appl. No. 19/329,353, filed Sep. 15, 2025, Pei et al.

U.S. Appl. No. 19/329,410, filed Sep. 15, 2025, Pei et al.

U.S. Appl. No. 19/329,417, filed Sep. 15, 2025, Pei et al.

U.S. Appl. No. 19/329,423, filed Sep. 15, 2025, Dehua Pei.

U.S. Appl. No. 19/329,427, filed Sep. 15, 2025, Dehua Pei.

U.S. Appl. No. 19/329,431, filed Sep. 15, 2025, Pei et al.

U.S. Appl. No. 19/329,440, filed Sep. 15, 2025, Pei et al.

Ali S.A., et al., "A Review of Methods Available to Estimate Solvent-Accessible Surface Areas of Soluble Proteins in the Folded and Unfolded States," Current Protein and Peptide Science, 2014, vol. 15, No. 3, 21 Pages.

Almarsson O., et al., "Crystal Engineering of the Composition of Pharmaceutical Phases. Do Pharmaceutical Co-Crystals Represent a New Path to Improved Medicines," Chemical Communications, 2004, vol. 17, pp. 1889-1896.

Alzani R., et al., "Suramin Induces Deoligomerization of Human Tumor Necrosis Factor (Alpha)," Journal of Biological Chemistry, Jun. 15, 1993, vol. 268, No. 17, pp. 12526-12529.

Angelini A., et al., "Bicyclic Peptide Inhibitor Reveals Large Contact Interface with a Protease Target," ACS Chemical Biology, 2012, vol. 7, No. 5, pp. 817-821.

Appelbaum U.S., et al., "Arginine Topology Controls Escape of Minimally Cationic Proteins from Early Endosomes to the Cytoplasm," Chemistry and Biology, Jul. 27, 2012, vol. 19, No. 7, pp. 819-830.

Ardi V.C., et al., "Macrocycles that Inhibit the Binding between Heat Shock Protein 90 and TPR—Containing Proteins," ACS Chemical Biology Journal, Dec. 16, 2011, vol. 6, No. 12, pp. 1357-1366 (18 Pages).

Baud V., et al., "Is NF-κB a Good Target for Cancer Therapy Hopes and Pitfalls," Nature Reviews Drug Discovery, Jan. 2009, vol. 8, No. 1, pp. 33-40 (18 Pages).

Bedewy W., et al., "Generation of a Cell-Permeable Cycloheptapeptidy1 Inhibitor against Peptidy1-Prolyl Isomerase Pin1," Organic & Biomolecular Chemistry, May 31, 2017, vol. 15, No. 21, pp. 4540-4543 (9 Pages).

Beste G., et al., "Small Antibody-like Proteins With Prescribed Ligand Specificities Derived From the Lipocalin Fold," Proceedings of the National Academy of Sciences of the United States of America, Mar. 1999, vol. 96, pp. 1898-1903.

Beutler B., et al., "Purification of Cachectin, A Lipoprotein Lipase-suppressing Hormone Secreted by Endotoxin-Induced Raw 264.7 Cells," The Journal of Experimental Medicine, May 1, 1985, vol. 161, pp. 984-995.

Birts C.N., et al., "A Cyclic Peptide Inhibitor of C-Terminal Binding Protein Dimerization Links Metabolism with Mitotic Fidelity in Breast Cancer Cells," Chemical Science, 2013, vol. 4, pp. 3046-3057 (13 Pages).

Buller F., et al., "Discovery of TNF Inhibitors from a DNA-Encoded Chemical Library Based on Diels-Alder Cycloaddition," Chemistry & Biology, Oct. 30, 2009, vol. 16, pp. 1075-1086.

Chan D.S-H., et al., "Structure-Based Discovery of Natural-Product-Like TNF-(Alpha) Inhibitors," Angewandte Chemie International Edition in English, Apr. 6, 2010, vol. 49, No. 16, pp. 2860-2864 (09 Pages).

Chatterjee J., et al., "N-Methylation of Peptides: A New Perspective in Medicinal Chemistry," Accounts of Chemical Research, Oct. 2008, vol. 41, No. 10, pp. 1331-1342.

Chen G., et al., "TNF-R1 Signaling: A Beautiful Pathway," Science, May 31, 2002, vol. 296, pp. 1634-1635.

Chen S., et al., "Bicyclic Peptide Ligands Pulled out of Cysteine-Rich Peptide Libraries," Journal of the American Chemical Society, Apr. 5, 2013, vol. 135, No. 17, pp. 6562-6569.

Chen S., et al., "Dithiol Amino Acids can Structurally Shape and Enhance the Ligand-Binding Properties of Polypeptides," Nature Chemistry, 2014, vol. 6, No. 11, pp. 1009-1016.

Chen S., et al., "Structurally Diverse Cyclisation Linkers Impose Different Backbone Conformations in Bicyclic Peptides," ChemBioChem, 2012, vol. 13, pp. 1032-1038.

Chen X., et al., "On-Bead Screening of Combinatorial Libraries: Reduction of Nonspecific Binding by Decreasing Surface Ligand Density," Journal of Combinatorial Chemistry, 2009, vol. 11, No. 4, pp. 604-611, (English).

Cheng S.H., et al., "Defective Intracellular Transport and Processing of CFTR is the Molecular Basis of Most Cystic Fibrosis," Cell, Nov. 16, 1990, vol. 63, No. 4, pp. 827-834.

Choi H., et al., "Discovery of the Inhibitors of Tumor Necrosis Factor Alpha with Structure-Based Virtual Screening," Bioorganic & Medicinal Chemistry Letters, 2010, vol. 20, pp. 6195-6198.

Cildir G., et al., "Noncanonical NF-κB Signaling in Health and Disease," Trends in Molecular Medicine, May 2016, vol. 22, No. 5, pp. 414-429.

Cochran A.G., et al., "Tryptophan Zippers: Stable, Monomeric B-Hairpins," Proceedings of the National Academy of Sciences, May 8, 2001, vol. 98, No. 10, pp. 5578-5583 (8 Pages).

Cooley C.B., et al., "Oligocarbonate Molecular Transporters: Oligomerization-Based Syntheses and Cell-Penetrating Studies," Journal of the American Chemical Society, 2009, vol. 131, No. 45, pp. 16401-16403.

Craik D.J., et al., "The Future of Peptide-Based Drugs," Chemical Biology and Drug Design, 2013, vol. 81, No. 1, pp. 136-147.

Cushing P.R., et al., "A Stabilizing Influence: CAL PDZ Inhibition Extends the Half-Life of (Delta)F508-CFTR," Angewandte Chemie International Edition, Dec. 2010, vol. 49, No. 51, pp. 9907-9911.

Dai S., et al., "The IkB Kinase (IKK) Inhibitor, NEMO-Binding Domain Peptide, Blocks Osteoclastogenesis and Bone Erosion in Inflammatory Arthritis," Journal of Biological Chemistry, Sep. 3, 2004, vol. 279, No. 36, pp. 37219-37222 (5 Pages).

Dave S.H., et al., "Amelioration of Chronic Murine Colitis by Peptide-Mediated Transduction of the IkB Kinase Inhibitor NEMO Binding Domain Peptide," The Journal of Immunology, 2007, vol. 179, No. 11, pp. 7852-7859 (9 Pages).

Delfin D.A., et al., "Improvement of Cardiac Contractile Function by Peptide-Based Inhibition of NF-κB in the Utrophin/Dystrophin-Deficient Murine Model of Muscular Dystrophy," Journal of Translational Medicine, May 17, 2011, vol. 9, No. 1, 68, 10 Pages.

Deshayes S., et al., "Cell-Penetrating Peptides: Tools for Intracellular Delivery of Therapeutics," Cellular and Molecular Life Sciences CMLS, 2005, vol. 62, No. 16, pp. 1839-1849.

Desimmie B.A., et al., "Phage Display-Directed Discovery of LEDGF/p75 Binding Cyclic Peptide Inhibitors of HIV Replication," Molecular Therapy, Nov. 2012, vol. 20, No. 11, pp. 2064-2075.

(56) References Cited

OTHER PUBLICATIONS

Dewan V., et al., "Cyclic Peptide Inhibitors of HIV-I Capsid-Human Lysyl-tRNA Synthetase Interaction," ACS Chemical Biology, 2012, vol. 7, pp. 761-769.
Do H., et al., "Difatty Acyl-Conjugated Linear and Cyclic Peptides for siRNA Delivery," ACS Omega, 2017, vol. 2, No. 10, pp. 6939-6957.
Dong S-L., et al., "A Photocontrolled (Beta)-Hairpin Peptide," Chemistry—A European Journal, 2006, vol. 12, No. 4, pp. 1114-1120.
Doran T.M., et al., "Role of Amino Acid Hydrophobicity, Aromaticity, and Molecular vol. on IAPP(20-29) Amyloid Self-assembly," Proteins: Structure, Function, and Bioinformatics, 2012, vol. 80, No. 4, pp. 1053-1065.
D'Souza C., et al., "Structural Parameters Modulating the Cellular Uptake of Disulfide-Rich Cyclic Cell-penetrating Peptides: MCoTI-II and SFTI-1," European Journal of Medicinal Chemistry, Elsevier Masson, Amsterdam, NL, Dec. 1, 2014, vol. 88, No. 99, pp. 10-18 (9 Pages), ISSN: 0223-5234, XP055725965, Retrieved from URL: http://dx.doi.org/10.1016/j.ejmech.2014.06.047.
Duchardt F., et al., "A Comprehensive Model for the Cellular Uptake of Cationic Cell-Penetrating Peptides," Traffic, 2007, vol. 8, No. 7, pp. 848-866.
Eguchi A., et al., "Protein Transduction Domain of HIV-1 Tat Protein Promotes Efficient Delivery of DNA into Mammalian Cells," Journal of Biological Chemistry, Jul. 13, 2001, vol. 276, No. 28, p. 26204-26210 (8 Pages).
Eisenberg D., et al., "The Hydrophobic Moment Detects Periodicity in Protein Hydrophobicity," Proceedings of the National Academy of Sciences, Jan. 1984, vol. 81, No. 1, pp. 140-144.
El Andaloussi S., et al., "Design of a Peptide-Based Vector, PepFect6, for Efficient Delivery of siRNA in Cell Culture and Systemically in Vivo," Nucleic Acids Research, May 2011, vol. 39, No. 9, pp. 3972-3987.
El-Sayed A., et al., "Delivery of Macromolecules using Arginine-Rich Cell-Penetrating Peptides: Ways to Overcome Endosomal Entrapment," The AAPS Journal, Mar. 2009, vol. 11, No. 1, pp. 13-22.
Engleman D.M., et al., "Identifying Nonpolar Transbilayer Helices in Amino Acid Sequences of Membrane Proteins," Annual Review of Biophysics and Biomolecular Structure, 1986, vol. 15, No. 1, pp. 321-353 (35 Pages).
Esposito E., et al., "TNF-Alpha as a Therapeutic Target in Inflammatory Diseases, Ischemia-Reperfusion Injury and Trauma," Current Medicinal Chemistry, 2009, vol. 16, No. 24, pp. 3152-3167.
Ferrari A., et al., "Caveolae-Mediated Internalization of Extracellular HIV-1 Tat Fusion Proteins Visualized in Real Time," Molecular Therapy, Aug. 2003, vol. 8, No. 2, pp. 284-294.
Fittipaldi A., et al., "Cell Membrane Lipid Rafts Mediate Caveolar Endocytosis of HIV-1 Tat Fusion Proteins," Journal of Biological Chemistry, Sep. 5, 2003, vol. 278, No. 36, pp. 34141-34149 (10 Pages).
Fosgerau K., et al., "Peptide Therapeutics: Current Status and Future Directions," Drug Discovery Today, Jan. 2015, vol. 20, No. 1, pp. 122-128.
Frankel A.D., et al., "Cellular Uptake of the Tat Protein from Human Immunodeficiency Virus," Cell, Dec. 23, 1988, vol. 55, No. 6, pp. 1189-1193.
Furka A., et al., "General Method for Rapid Synthesis of Multicomponent Peptide Mixtures," Internal Journal of Peptide and Protein Research, 1991, vol. 37, pp. 487-493.
Futaki S., "Membrane-permeable Arginine-rich Peptides and the Translocation Mechanisms," Advanced Drug Delivery Reviews, 2005, vol. 57, No. 4, pp. 547-558.
Gaurnier-Hausser A., et al., "NEMO-Binding Domain Peptide Inhibits Constitutive NF-(Kappa)B Activity and Reduces Tumor Burden in a Canine Model of Relapsed, Refractory Diffuse Large B-Cell Lymphoma," Clinical Cancer Research, Jul. 15, 2011, vol. 17, No. 14, pp. 4661-4671 (12 Pages).
Gotoh Y., et al., "A Homogeneous Time-Resolved Fluorescence-Based High-Throughput Screening System for Discovery of Inhibitors of IKK(Beta)-NEMO Interaction," Analytical Biochemistry, 2010, vol. 405, No. 1, pp. 19-27.
Goun E.A., et al., "Molecular Transporters: Synthesis of Oligoguanidinium Transporters and Their Application to Drug Delivery and Real-time Imaging," ChemBioChem, Oct. 2006, vol. 7, No. 10, pp. 1497-1515.
Green M., et al., "Autonomous Functional Domains of Chemically Synthesized Human Immunodeficiency Virus Tat Trans-Activator Protein," Cell, Dec. 23, 1988, vol. 55, No. 6, pp. 1179-1188.
Guo B., et al., "Protein Engineering of the N-Terminus of NEMO: Structure Stabilization and Rescue of IKK(Beta) Binding," Biochemistry, Oct. 6, 2014, vol. 53, No. 43, pp. 6776-6785.
Gupta B., et al., "Intracellular Delivery of Large Molecules and Small Particles by Cell-Penetrating Proteins and Peptides," Advanced Drug Delivery Reviews, 2005, vol. 57, No. 4, pp. 637-651.
Gupta S.C., et al., "Inhibiting NF-(Kappa)B Activation by Small Molecules as a Therapeutic Strategy," Biochimica et Biophysica Acta (BBA)-Gene Regulatory Mechanisms, 2010, vol. 1799, No. 10-12, pp. 775-787 (32 Pages).
Hancock R., et al., "Peptide Inhibitors of the Keap1-Nrf2 Protein-Protein Interaction," Free Radical Biology and Medicine, 2012, vol. 52, pp. 444-451.
He M.M., et al., "Small-molecule Inhibition of TNF-(Alpha)," Science, Nov. 11, 2005, vol. 310, pp. 1022-1025.
Heinis C., et al., "Phage-Encoded Combinatorial Chemical Libraries Based on Bicyclic Peptides," Nature Chemical Biology, Jul. 2009, vol. 5, No. 7, pp. 502-507.
Herce H.D., et al., "Arginine-Rich Peptides Destabilize the Plasma Membrane, Consistent with a Pore Formation Translocation Mechanism of Cell-Penetrating Peptides," Biophysical Journal, Oct. 2009, vol. 97, No. 7, pp. 1917-1925.
Herce H.D., et al., "Molecular Dynamics Simulations Suggest a Mechanism for Translocation of the HIV-1 TAT Peptide Across Lipid Membranes," Proceedings of the National Academy of Sciences, Dec. 26, 2007, vol. 104, No. 52, pp. 20805-20810.
Herndon T.M., et al., "U.S. Food and Drug Administration Approval: Carfilzomib for the Treatment of Multiple Myeloma," Clinical Cancer Research, Sep. 1, 2013, vol. 19, No. 17, pp. 4559-4563 (6 Pages).
Herrington F.D., et al., "Modulation of NF-κB Signaling as a Therapeutic Target in Autoimmunity," Journal of Biomolecular Screening, 2016, vol. 21, No. 3, pp. 223-242.
Hintersteiner M., et al., "Single Bead Labeling Method for Combining Confocal Fluorescence on-bead Screening and Solution Validation of Tagged One-Bead One-Compound Libraries," Chemical Biology, Jul. 31, 2009, vol. 16, pp. 724-735.
Hirose H., et al., "Transient Focal Membrane Deformation Induced by Arginine-rich Peptides Leads to Their Direct Penetration Into Cells, " Molecular Therapy, May 2012, vol. 20, No. 5, pp. 984-993.
Hopp T.P., et al., "Prediction of Protein Antigenic Determinants from Amino Acid Sequences," Proceedings of the National Academy of Sciences, Jun. 1981, vol. 78, No. 6, pp. 3824-3828.
Houghten R.A., et al., "Generation and Use of Synthetic Peptide Combinatorial Libraries for Basic Research and Drug Discovery," Nature, Nov. 7, 1991, vol. 354, pp. 84-86.
Hoyer J., et al., "Peptide Vectors for the Nonviral Delivery of Nucleic Acids," Accounts of Chemical Research, 2012, vol. 45, No. 7, pp. 1048-1056.
Hu B-H., et al., "Method for Screening and MALDI-TOF MS Sequencing of Encoded Combinatorial Libraries," Analytical Chemistry, Oct. 1, 2007, vol. 79, No. 19, pp. 7275-7285.
Huang H-C., et al., "Regulation of the Antioxidant Response Element by Protein Kinase C-Mediated Phosphorylation of NF-E2-Related Factor 2," Proceedings of the National Academy of Sciences, Nov. 7, 2000, vol. 97, No. 23, pp. 12475-12480 (7 Pages).
Inoyama D., et al., "Optimization of Fluorescently Labeled Nrf2 Peptide Probes and the Development of a Fluorescence Polarization Assay for the Discovery of Inhibitors of keapl-Nrf2 Interaction," Journal of Biomolecular Screening, 2012, vol. 17, No. 4, pp. 435-447.

(56) References Cited

OTHER PUBLICATIONS

International Search Report and Written Opinion. Issued by the International Searching Authority (US) in Application No. PCT/US2017/063020 on May 4, 2018. 14 pages.
Ishii T., et al., "Transcription Factor Nrf2 Coordinately Regulates a Group of Oxidative Stress-inducible Genes in Macrophages," Journal of Biological Chemistry, May 26, 2000, vol. 275, No. 21, pp. 16023-16029 (8 Pages).
Janin J., "Surface and Inside vols. in Globular Proteins," Nature, Feb. 8, 1979, vol. 277, No. 5696, pp. 491-492 (3 Pages).
Jeong J.H., et al., "siRNA Conjugate Delivery Systems," Bioconjugate Chemistry, 2009, vol. 20, No. 1, pp. 5-14.
Jimi E., et al., "Selective Inhibition of NF-(Kappa)B Blocks Osteoclastogenesis and Prevents Inflammatory Bone Destruction in Vivo," Nature Medicine, Jun. 2004, vol. 10, No. 6, pp. 617-624.
Joo S.H., "Cyclic Peptides as Therapeutic Agents and Biochemical Tools," Biomolecules & Therapeutics, 2012, vol. 20, No. 1, pp. 19-26.
Joo S.H., et al., "High-Throughput Sequence Determination of Cyclic Peptide Library Members by Partial Edman Degradation/Mass Spectrometry," Journal of the American Chemical Society, 2006, vol. 128, No. 39, pp. 13000-13009.
Josephson L., et al., "High-Efficiency Intracellular Magnetic Labeling with Novel Superparamagnetic-Tat Peptide Conjugates," Bioconjugate Chemistry, 1999, vol. 10, No. 2, pp. 186-191.
Junkes C., et al., "Cyclic Antimicrobial R-, W-rich Peptides: the Role of Peptide Structure and *E. coli* Outer and Inner Membranes in Activity and the Mode of Action," European Biophysics Journal, 2011, vol. 40, No. 4, pp. 515-528.
Kansanen E., et al., "The Keap1-Nrf2 Pathway: Mechanisms of Activation and Dysregulation in Cancer," Redox Biology, 2013, vol. 1, No. 1, pp. 45-49.
Kaplan I.M., et al., "Cationic TAT Peptide Transduction Domain Enters Cells by Macropinocytosis," Journal of Controlled Release, 2005, vol. 102, No. 1, pp. 247-253.
Kawakami M., et al., "Studies of Endotoxin-induced Decrease in Lipoprotein-lipase Activity," The Journal of Experimental Medicine, Sep. 1, 1981, vol. 154, pp. 631-639.
Kerem B-S., et al., "Identification of the Cystic Fibrosis Gene: Genetic Analysis," Science, Sep. 8, 1989, vol. 245, No. 4922, pp. 1073-1080.
Khabar K.S.A., et al., "WEHI-13VAR: A Stable and Sensitive Variant of WEHI 164 Clone 13 Fibrosarcoma for Tumor Necrosis Factor Bioassay," Immunology Letters, 1995, vol. 46, pp. 107-110.
Khakshoor O., et al., "Artificial P-Sheets: Chemical Models of (Beta)-Sheets," Current Opinion in Chemical Biology, 2008, vol. 12, No. 6, pp. 722-729.
Kimber M.S., et al., "Structural Basis for Specificity Switching of the Src SH2 Domain," Molecular Cell, Jun. 2000, vol. 5, No. 6, pp. 1043-1049.
Kodadek T., et al., "Optimized Protocols for the Isolation of Specific Protein-Binding Peptides or Peptoids from Combinatorial Libraries Displayed on Beads," Molecular Omics, 2006, vol. 2, pp. 25-35.
Koide A., et al., "The Fibronectin Type III Domain as a Scaffold for Novel Binding Proteins," Journal of Molecular Biology, 1998, vol. 284, pp. 1141-1151.
Kornegay J.N., et al., "NBD Delivery Improves the Disease Phenotype of the Golden Retriever Model of Duchenne Muscular Dystrophy," Skeletal Muscle, 2014, vol. 4, No. 1, 18, 17 Pages.
Kriegler M., et al., "A Novel Form of TNF/Cachectin Is a Cell Surface Cytotoxic Transmembrane Protein: Ramifications for the Complex Physiology of TNF," Cell, Apr. 8, 1988, vol. 53, pp. 45-53.
Kyte J., et al., "A Simple Method for Displaying the Hydropathic Character of a Protein," Journal of Molecular Biology, 1982, vol. 157, No. 1, pp. 105-132.
Lai J.R., et al., "Design of Non-Cysteine-Containing Antimicrobial (Beta)-Hairpins: Structure-Activity Relationship Studies with Linear Protegrin-1 Analogues," Biochemistry, 2002, vol. 41, No. 42, pp. 12835-12842.
Lam K.S., et al., "A New Type of Synthetic Peptide Library for Identifying Ligand-binding Activity," Nature, Nov. 7, 1991, vol. 354, No. 6348, pp. 82-84.
Langham A.A., et al., "Comparison of Interactions Between Beta-Hairpin Decapeptides and SDS/DPC Micelles from Experimental and Simulation Data," BMC Biochemistry, 2007, vol. 8, No. 11, pp. 1-13.
Larochelle J.R., et al., "Fluorescence Correlation Spectroscopy Reveals Highly Efficient Cytosolic Delivery of Certain Penta-Arg Proteins and Stapled Peptides," Journal of the American Chemical Society, 2015, vol. 137, No. 7, pp. 2536-2541.
Lattig-Tunnemann G., et al., "Backbone Rigidity and Static Presentation of Guanidinium Groups Increases Cellular Uptake of Arginine-Rich Cell-Penetrating Peptides," Nature Communications, 2011, vol. 2, No. 453, 6 Pages.
Leduc A-M., et al., "Helix-stabilized Cyclic Peptides as Selective Inhibitors of Steroid Receptor-coactivator Interactions, " Proceedings of the National Academy of Sciences of the United States of America, Sep. 30, 2003, vol. 100, No. 20, pp. 11273-11278.
Leung C-H., et al., "Structure-based Repurposing of FDA-Approved Drugs as TNF(alpha) Inhibitors," ChemMedChem, 2011, vol. 6, pp. 765-768.
Lewis K.N., et al., "Nrf2, A Guardian of Healthspan and Gatekeeper of Species Longevity," Integrative and Comparative Biology, 2010, vol. 50, No. 5, pp. 829-843.
Lian W., et al., "Cell-Permeable Bicyclic Peptide Inhibitors Against Intracellular Proteins," Journal of the American Chemical Society, Jun. 27, 2014, vol. 136, No. 28, pp. 9830-9833.
Lian W., et al., "Screening Bicyclic Peptide Libraries for Protein-Protein Interaction Inhibitors: Discovery of a Tumor Necrosis Factor-A Antagonist," Journal of the American Chemical Society, Aug. 14, 2013, vol. 135, No. 32, pp. 11990-11995 (12 Pages).
Liu J., et al., "Nanostructured Materials Designed for Cell Binding and Transduction," Biomacromolecules, 2001, vol. 2, No. 2, pp. 362-368.
Liu R., et al., "A Novel Peptide-Based Encoding System for "One-Bead One-Compound" Peptidomimetic and Small Molecule Combinatorial Libraries," Journal of the American Chemical Society, 2002, vol. 124, No. 26, pp. 7678-7680.
Liu T., et al., "High-Throughput Screening of One-Bead-One Compound Libraries: Identification of Cyclic Peptidyl Inhibitors Against Calcineurin/NFAT Interaction," ACS Combinatorial Science Journal, 2011, vol. 13, pp. 537-546.
Liu T., et al., "Membrane Permeable Cyclic Peptidyl Inhibitors Against Human Peptidylprolyl Isomerase Pin1," Journal of Medicinal Chemistry, 2010, vol. 53, No. 6, pp. 2494-2501.
Liu T., et al., "Synthesis and Screening of a Cyclic Peptide Library: Discovery of Small-Molecule Ligands Against Human Prolactin Receptor," Bioorganic & Medicinal Chemistry, Feb. 1, 2009, vol. 17, No. 3, pp. 1026-1033 (14 Pages).
Liu X., et al., "Do We Need to Optimize Plasma Protein and Tissue Binding in Drug Discovery?," Current Topics in Medicinal Chemistry, 2011, vol. 11, No. 4, pp. 450-466.
Lo S-C., et al., "Structure of the Keap1:Nrf2 Interface Provides Mechanistic Insight Into Nrf2 Signaling," The EMBO Journal, 2006, vol. 25, No. 15, pp. 3605-3617.
Luzi S., et al., "Subunit Disassembly and Inhibition of TNF(Alpha) by a Semi-Synthetic Bicyclic Peptide," Protein Engineering, Design and Selection, 2015, vol. 28, No. 2, pp. 45-52, XP055507589.
Ma B., et al., "Total Synthesis of the Antimitotic Bicyclic Peptide Celogentin C," Journal of the American Chemical Society, Jan. 27, 2010, vol. 132, No. 3, pp. 1159-1171 (37 Pages), XP055300884.
Ma L., et al., "A Novel Small-molecule Tumor Necrosis Factor Alpha Inhibitor Attenuates Inflammation in a Hepatitis Mouse Model," The Journal of Biological Chemistry, May 2, 2014, vol. 289, No. 18, pp. 12457-12466 (11 Pages).
Ma Y., et al., "Direct Cytosolic Delivery of Cargoes in Vivo by a Chimera Consisting of D- and L-Arginine Residues," Journal of Controlled Release, 2012, vol. 162, No. 2, pp. 286-294.
Maiolo J.R., et al., "Effects of Cargo Molecules on the Cellular Uptake of Arginine-rich Cell-penetrating Peptides," Biochimica et Biophysica Acta (BBA)—Biomembranes, Jul. 2005, vol. 1712, No. 2, pp. 161-172.

(56) References Cited

OTHER PUBLICATIONS

Mancini F., et al., "Inhibition of Tumor Necrosis Factor-(Alpha) (TNF-Alpha)/ TNF-(Alpha) Receptor Binding by Structural Analogues of Suramin," Biochemical Pharmacology, 1999, vol. 58, No. 5, pp. 851-859.
Mandal D., et al., "Cell-Penetrating Homochiral Cyclic Peptides as Nuclear-Targeting Molecular Transporters," Angewandte Chemie International Edition, 2011, vol. 50, No. 41, pp. 9633-9637.
Martin T.L., et al., "The Light Side of Horseradish Peroxidase Histochemistry," Journal of Histochemistry and Cytochemistry, 1984, vol. 32, No. 7, p. 793.
May M.J., et al., "Selective Inhibition of NF-κB Activation by a Peptide That Blocks the Interaction of NEMO with the IkB Kinase Complex," Science, Sep. 1, 2000, pp. 1550-1554.
Meyer D., et al., "Aromatic Interactions with Naphthylalanine in a (Beta)-Hairpin Peptide," Journal of Peptide Science, 2013, vol. 19, No. 5, pp. 277-282.
Millward S.W., et al., "Design of Cyclic Peptides That Bind Protein Surfaces with Antibody-Like Affinity," ACS Chemical Biology, 2007, vol. 2, No. 9, pp. 625-634, Published Online on Sep. 21, 2007.
Miranda E., et al., "A Cyclic Peptide Inhibitor of HIF-1 Heterodimerization That Inhibits Hypoxia Signaling in Cancer Cells," Journal of the American Chemical Society, 2013, vol. 135, pp. 10418-10425.
Mishra A., et al., "Translocation of HIV TAT Peptide and Analogues Induces by Multiplexed Membrane and Cytoskeletal Interactions," Proceedings of the National Academy of Sciences of the United States of America, Oct. 11, 2011, vol. 108, No. 41, pp. 16883-16888.
Mitra S., et al., "Highly Sensitive Peptide-Based Probes for Protein Tyrosine Phosphatase Activity Utilizing a Fluorogenic Mimic of Phosphotyrosine," Bioorganic and Medicinal Chemistry Letters, 2005, vol. 15, No. 23, pp. 5142-5145.
Mueller J., et al., "Comparison of Cellular Uptake Using 22 CPPs in 4 Different Cell Lines," Bioconjugate Chemistry, 2008, vol. 19, No. 12, pp. 2363-2374.
Muratovska A., et al., "Conjugate for Efficient Delivery of Short Interfering RNA (siRNA) into Mammalian Cells," FEBS Letters, 2004, vol. 558, No. 1-3, pp. 63-68.
Nakase I., et al., "Efficient Intracellular Delivery of Nucleic Acid Pharmaceuticals Using Cell-Penetrating Peptides," Accounts of Chemical Research, 2012, vol. 45, No. 7, pp. 1132-1139, E-Published Dec. 30, 2011.
Nakase I., et al., "Interaction of Arginine-Rich Peptides with Membrane-Associated Proteoglycans is Crucial for Induction of Actin Organization and Macropinocytosis," Biochemistry, 2007, vol. 46, No. 2, pp. 492-501.
Ndikuyeze G.H., et al., "A Phase I Clinical Trial of Systemically Delivered NEMO Binding Domain Peptide in Dogs with Spontaneous Activated B-Cell Like Diffuse Large B-Cell Lymphoma," PloS one, May 2014, vol. 9, Issue. 5, e95404, 10 Pages.
Nevola L., et al., "Modulating Protein-Protein Interactions: The Potential of Peptides," Chemical Communications, 2015, vol. 51, No. 16, pp. 3302-3315 (15 Pages).
Nguyen L.T., et al., "Serum Stabilities of short Tryptophan-and Arginine-rich Antimicrobial Peptide Analogs," Plos One, Sep. 10, 2010, vol. 5, No. 9 (e12684), pp. 1-8.
Nori A., et al., "Tat-conjugated Synthetic Macromolecules Facilitate Cytoplasmic Drug Delivery to Human Ovarian Carcinoma Cells," Bioconjugate Chemistry, 2003, vol. 14, No. 1, pp. 44-50.
Oeckinghaus A., et al., "The NF-κB Family of Transcription Factors and its Regulation," Cold Spring Harbor Perspectives in Biology, 2009, vol. 1, No. 4, a000034, 15 Pages.
Oh D., et al., "Enhanced Cellular Uptake of Short Polyarginine Peptides through Fatty Acylation and Cyclization," Molecular Pharmaceutics, 2014, vol. 11, No. 8, pp. 2845-2854.
Orange J.S., et al., "Cell Penetrating Peptide Inhibitors of Nuclear Factor-kappa B," Cellular and Molecular Life Sciences, 2008, vol. 65, No. 22, pp. 3564-3591.
Palm-Apergi C., et al., "The Membrane Repair Response Masks Membrane Disturbances Caused by Cell-penetrating Peptide Uptake," The FASEB Journal, Jan. 2009, vol. 23, No. 1, pp. 214-223 (11 Pages).
Pande S.V., et al., "Synthesis and Antibacterial Evaluation of Carboxamide Derivatives of Amino Acids," Pharmaceutical Chemistry Journal, Apr. 2014, vol. 48, No. 1, 5 Pages.
Pelay-Gimeno M., et al., "Structure-based Design of Inhibitors of Protein-protein Interactions: Mimicking Peptide Binding Epitopes," Angewandte Chemie International Edition, 2015, vol. 54, No. 31, pp. 8896-8927.
Pelay-Gimeno M., et al., "Structure-based Design of Protein-protein Interaction Inhibitors: Stabilization and Mimicking of Peptide Ligands," Angewandte Chemie, 2015, vol. 127, No. 31, pp. 9022-9054.
Pennica D., et al., "Human Tumour Necrosis Factor: Precursor Structure, Expression and Homology to Lymphotoxin, " Nature, Dec. 20-27, 1984, vol. 312, pp. 724-729.
Peterson J.M., et al., "Peptide-based Inhibition of NF-(Kappa)B Rescues Diaphragm Muscle Contractile Dysfunction in a Murine Model of Duchenne Muscular Dystrophy," Molecular Medicine, May-Jun. 2011, vol. 17, No. 5-6, pp. 508-515.
Pham W., et al., "Enhancing Membrane Permeability by Fatty Acylation of Oligoarginine Peptides," ChemBioChem, 2004, vol. 5, No. 8, pp. 1148-1151.
Pooga M., et al., "Cellular Translocation of Proteins by Transportan," The FASEB Journal, 2001, vol. 15, No. 8, pp. 1451-1453 (23 Pages).
Qian Z., et al., "Early Endosomal Escape of a Cyclic Cell-Penetrating Peptide Allows Effective Cytosolic Cargo Delivery," Biochemistry, 2014, vol. 53, No. 24, pp. 4034-4046, DOI: 10.1021/bi5004102.
Qian Z., et al., "Efficient Delivery of Cyclic Peptides into Mammalian Cells with Short Sequence Motifs," ACS Chemical Biology, 2013, vol. 8, No. 2, pp. 423-431.
Qian Z., et al., "Enhancing the Cell Permeability and Metabolic Stability of Peptidyl Drugs by Reversible Bicyclization," Angewandte Chemie International Edition, Feb. 1, 2017, vol. 56, No. 6, pp. 1525-1529 (11 Pages).
Qian Z., et al., "Intracellular Delivery of Peptidyl Ligands by Reversible Cyclization: Discovery of a PDZ Domain Inhibitor That Rescues CFTR Activity," Angewandte Chemie International Edition, May 11, 2015, vol. 54, No. 20, (127), (5972), pp. 5874-5878 (11 Pages).
Qian, Ziqing, et al. "Monitoring the cytosolic entry of cell-penetrating peptides using a pH-sensitive fluorophore." Chemical Communications 51.11 (2015): 2162-2165.
Qian Ziqing et al., "Discovery and Mechanism of Highly Efficient Cyclic Cell-Penetrating Peptides", Biochemistry, vol. 55, No. 18, doi:10.1021/acs.biochem.6b00226, ISSN 0006-2960, (May 10, 2016), pp. 2601-2612, URL: https://pubs.acs.org/doi/pdf/10.1021/acs.biochem.6b00226, XP055854712.
Rajendran P., et al., "Antioxidants and Human Diseases," Clinica Chimica Acta, 2014, vol. 436, pp. 332-347.
Reay D.P., et al., "Systemic Delivery of NEMO Binding Domain/IKKγ Inhibitory Peptide to Young Max Mice Improves Dystrophic Skeletal Muscle Histopathology," Neurobiology of Disease, Sep. 2011, vol. 43, No. 3, pp. 598-608 (21 Pages).
Rezai T., et al., "Conformational Flexibility, Internal Hydrogen Bonding, and Passive Membrane Permeability: Successful in Silico Prediction of the Relative Permeabilities of Cyclic Peptides," Journal of the American Chemical Society, 2006, vol. 128, No. 43, pp. 14073-14080.
Richard J.P., et al., "Cellular Uptake of Unconjugated TAT Peptide Involves Clathrin-dependent Endocytosis and Heparan Sulfate Receptors," Journal of Biological Chemistry, Apr. 15, 2005, vol. 280, No. 15, pp. 15300-15306.
Rizo J., et al., "Constrained Peptides: Models of Bioactive Peptides and Protein Substructures," Annual Review of Biochemistry, 1992, vol. 61, pp. 387-418.
Robinson J.A., "(Beta)-Hairpin Peptidomimetics: Design, Structures and Biological Activities," Accounts of Chemical Research, Oct. 2008, vol. 41, No. 10, pp. 1278-1288.

(56) References Cited

OTHER PUBLICATIONS

Rothbard J.B., et al., "Conjugation of Arginine Oligomers to Cyclosporin a Facilitates Topical Delivery and Inhibition of Inflammation," Nature Medicine, Nov. 2000, vol. 6, No. 11, pp. 1253-1257.
Rothwarf D.M., et al., "IKK-(gamma) is An Essential Regulatory Subunit of the IkB Kinase Complex," Nature, Sep. 17, 1998, vol. 395, No. 6699, pp. 297-300.
Rueping M., et al., "Cellular Uptake Studies With (Beta)-Peptides," ChemBioChem, Mar. 2002, vol. 3, No. 2-3, pp. 257-259.
Rushe M., et al., "Structure of a NEMO/IKK-Associating Domain Reveals Architecture of the Interaction Site, " Structure, May 2008, vol. 16, No. 5, pp. 798-808.
Rutledge S.E., et al., "A. Molecular Recognition of Protein Surfaces: High Affinity Ligands for the CBP KIX Domain," Journal of the American Chemical Society, 2003, vol. 125, No. 47, pp. 14336-14347.
Saar K., et al., "Cell-penetrating Peptides: A Comparative Membrane Toxicity Study," Analytical Biochemistry, 2005, vol. 345, No. 1, pp. 55-65.
Saito H., et al., "A Tumor Necrosis Factor Receptor Loop Peptide Mimic Inhibits Bone Destruction to the Same Extent as Anti-tumor Necrosis Factor Monoclonal Antibody in Murine Collagen-induced Arthritis," Arthritis & Rheumatism, Apr. 2007, vol. 56, No. 4, pp. 1164-1174.
Sako Y., et al., "Ribosomal Synthesis of Bicyclic Peptides via Two Orthogonal Inter-Side-Chain Reactions," Journal of the American Chemical Society, 2008, vol. 130, No. 23, pp. 7232-7234.
Sandberg M., et al., "NRF2-regulation in Brain Health and Disease: Implication of Cerebral Inflammation," Neuropharmacology, Apr. 2014, vol. 79, pp. 298-306.
Schmidt N., et al., "Arginine-rich Cell-penetrating Peptides," FEBS Letters, 2010, vol. 584, No. 9, pp. 1806-1813.
Scholl M., et al., "Dendritic and Hyperbranched Polyamides," Progress in Polymer Science, 2009, vol. 34, No. 1, pp. 24-61.
Schwarze S.R., et al., "In Vivo Protein Transduction: Delivery of a Biologically Active Protein into the Mouse," Science, Sep. 3, 1999, vol. 285, No. 5433, pp. 1569-1572(5 Pages).
Shen Q., et al., "De Novo Design of Helical Peptides to Inhibit Tumor Necrosis Factor-(alpha) by Disrupting Its Trimer Formation," Medicinal Chemistry Communications, 2016, vol. 7, pp. 725-729 (7 Pages).
Shibata W., et al., "Cutting Edge: The IkB kinase (IKK) Inhibitor, NEMO-Binding Domain Peptide, Blocks Inflammatory Injury in Murine Colitis," The Journal of Immunology, 2007, vol. 179, No. 5, pp. 2681-2685 (6 Pages).
Shrake A., et al., "Environment and Exposure to Solvent of Protein Atoms. Lysozyme and Insulin," Journal of Molecular Biology, 1973, vol. 79, No. 2, pp. 351-371 (22 Pages).
Skelton N.J., et al., "(Beta)-Hairpin Polypeptides by Design and Selection," Journal of Spectroscopy, 2003, vol. 17, No. 2-3, pp. 213-230.
Srinivas N., et al., "Biaryl Amino Acid Templates in Place of D-Pro-L-Pro in Cyclic (Beta)-hairpin Cationic Antimicrobial Peptidemimetics," Organic and Biomolecular Chemistry, 2007, vol. 5, pp. 3100-3105.
Stanford S.M., et al., "High-Throughput Screen using a Single-Cell Tyrosine Phosphatase Assay Reveals Biologically Active Inhibitors of Tyrosine Phosphatase CD45," Proceedings of the National Academy of Sciences, Aug. 28, 2012, vol. 109, No. 35, p. 13972-13977.
Steiner D., et al., "Efficient Selection of DARPins With Subnanomolar Affinities Using SRP Phage Display," Journal of Molecular Biology, 2008, vol. 382, pp. 1211-1227.
Stewart K.M., et al., "Cell-Penetrating Peptides as Delivery Vehicles for Biology and Medicine," Organic and Biomolecular Chemistry, 2008, vol. 6, No. 13, pp. 2242-2255.
Suhorutsenko J., et al., "Cell-penetrating Peptides, PepFects, Show No Evidence of Toxicity and Immunogenicity in Vitro and in Vivo," Bioconjugate Chemistry, Nov. 2011, vol. 22, No. 11, pp. 2255-2262.
Sun S-C., et al., "Regulation of Nuclear Factor-KB in Autoimmunity," Trends in Immunology, Jun. 2013, vol. 34, No. 6, pp. 282-289 (18 Pages).
Sun Y., et al., "A Thioester Ligation Approach to Amphipathic Bicyclic Peptide Library," Organic Letters, 2001, vol. 3, No. 11, pp. 1681-1684.
Sweeney M.C., et al., "Decoding Protein-protein Interactions Through Combinatorial Chemistry: Sequence Specificity of SHP-1, SHP-2, and Ship SH2 Domains," Biochemistry, 2005, vol. 44, No. 45, pp. 14932-14947.
Taguchi K., et al., "Molecular Mechanisms of the Keap1-Nrf2 Pathway in Stress Response and Cancer Evolution," Genes to Cells, 2011, vol. 16, No. 2, pp. 123-140.
Takada Y., et al., "Evodiamine Abolishes Constitutive and Inducible NF-κB Activation by Inhibiting IkBa Kinase Activation, Thereby Suppressing NF-KB-Regulated Antiapoptotic and Metastatic Gene Expression, Up-Regulating Apoptosis, and Inhibiting Invasion," Journal of Biological Chemistry, Apr. 29, 2005, vol. 280, No. 17, pp. 17203-17212.
Takasaki W., et al., "Structure-based Design and Characterization of Exocyclic Peptidomimetics That Inhibit TNF(Alpha) Binding to Its Receptor," Nature Biotechnology, Nov. 1997, vol. 15, pp. 1266-1270.
Tang P., et al., "Human pro-Tumor Necrosis Factor Is a Homotrimer," Biochemistry (Mosc), 1996, vol. 35, No. 25, pp. 8216-8225.
Tavassoli A., et al., "Inhibition of HN Budding by a Genetically Selected Cyclic Peptide Targeting the Gag-TSG101 Interaction," ACS Chemical Biology, 2008, vol. 3, No. 12, pp. 757-764.
Thakkar A., et al., "Global Analysis of Peptide Cyclization Efficiency," ACS Combinatorial Science, Feb. 11, 2013, vol. 15, No. 2, pp. 120-129 (21 Pages).
Thakkar A., et al., "Traceless Capping Agent for Peptide Sequencing by Partial Edman Degradation and Mass Spectrometry," Analytical Chemistry, Aug. 15, 2006, vol. 78, No. 16, pp. 5935-5939.
Tien M.Z., et al., "Maximum Allowed Solvent Accessibilites of Residues in Proteins," Public Library of Science ONE, Nov. 21, 2013, vol. 8, No. 11, e80635, pp. 1-8.
Timmerman P., et al., "A Combinatorial Approach for the Design of Complementarity Determining Region-Derived Peptidomimetics with in Vitro Anti-Tumoral Activity," Journal of Biological Chemistry, Dec. 4, 2009, vol. 284, No. 49, pp. 34126-34134.
Tong K.I., et al., "Different Electrostatic Potentials Define ETGE and DLG Motifs as Hinge and Latch in Oxidative Stress Response," Molecular and Cellular Biology, Nov. 2007, vol. 27, No. 21, pp. 7511-7521.
Tong K.I., et al., "Keap1 Recruits Neh2 Through Binding to ETGE and DLG Motifs: Characterization of the Two-site Molecular Recognition Model," Molecular and Cellular Biology, Apr. 2006, vol. 26, No. 8, pp. 2887-2900.
Trinh T.B., et al., "Discovery of a Direct Ras Inhibitor by Screening a Combinatorial Library of Cell-Permeable Bicyclic Peptides," ACS Combinational Science, American Chemical Society, Jan. 11, 2016, vol. 18, No. 1, pp. 75-85, XP055431276.
Upadhyaya P., et al., "Direct Ras Inhibitors Identified From a Structurally Rigidified Bicyclic Peptide Library," Tetrahedron, Elsevier Sience Publishers, Amsterdam, NL, Oct. 21, 2014, vol. 70, No. 42, pp. 7714-7720 (15 Pages).
Upadhyaya P., et al., "Inhibition of Ras Signaling by Blocking Ras-effector Interactions With Cyclic Peptides," Angewandte Chemie, Int Ed, 2015, vol. 54, No. 26, (127), pp. 7602-7606 (6 Pages). pp. 7712-7716.
Varkouhi A.K., et al., "Endosomal Escape Pathways for Delivery of Biologicals," Journal of Controlled Release, May 2011, vol. 151, No. 3, pp. 220-228, Epublished on Nov. 13, 2010.
Virta P., et al., "Solid-Supported Synthesis of Cryptand-Like Macrobicyclic Peptides," The Journal of Organic Chemistry, 2003, vol. 68, No. 22, pp. 8534-8538.
Vriens K., et al., "Antifungal Plant Defensins: Mechanisms of Action and Production, " Molecules, Aug. 14, 2014, vol. 19, No. 8, pp. 12280-12303.
Wadia J.S., et al., "Transmembrane Delivery of Protein and Peptide Drugs by TAT-mediated Transduction in the Treatment of Cancer,"

(56) References Cited

OTHER PUBLICATIONS

Advanced Drug Delivery Reviews, Feb. 2005, vol. 57, No. 4, pp. 579-596, Epublished on Dec. 19, 2004.
Wajant H., et al., "Tumor Necrosis Factor Signaling," Cell Death and Differentiation, 2003, vol. 10, pp. 45-65.
Wells J.A., et al., "Reaching for High-hanging Fruit in Drug Discovery at Protein-protein Interfaces," Nature, Dec. 13, 2007, vol. 450, No. 7172, pp. 1001-1009.
White T.R., et al., "On-resin N-methylation of Cyclic Peptides for Discovery of Orally Bioavailable Scaffolds," Nature Chemical Biology, 2011, vol. 7, No. 11, pp. 810-817.
Wolde M., et al., "Targeting CAL as a Negative Regulator of (Delta)F508-CFTR Cell-surface Expression an RNA Interference and Structure-based Mutagenetic Approach," Journal of Biological Chemistry, Mar. 16, 2007, vol. 282, No. 11, pp. 8099-8109, Epublished Dec. 11, 2006.
Wu X., et al., "Inhibition of Ras-effector Interactions by Cyclic Peptides," Medchemcomm, 2013, vol. 4, pp. 378-382.
Xu L., et al., "Directed Evolution of High-Affinity Antibody Mimics Using mRNA Display," Chemistry & Biology, Aug. 2002, vol. 9, pp. 933-942.
Yamagishi Y., et al., "Natural Product-Like Macrocyclic N-Methyl-Peptide Inhibitors Against a Ubiquitin Ligase Uncovered From a Ribosome-Expressed De Novo Library," Chemistry and Biology, Dec. 23, 2011, vol. 18, pp. 1562-1570.
Yamaoka S., et al., "Complementation Cloning of NEMO, A Component of the I(Kappa)B Kinase Complex Essential for NF-(Kappa)B Activation," Cell, Jun. 26, 1998, vol. 93, No. 7, pp. 1231-1240.
Yin J., et al., "Genetically Encoded Short Peptide Tag for Versatile Protein Labeling by Sfp Phosphopantetheinyl Transferase," Proceedings of the National Academy of Sciences of the United States of America, Nov. 1, 2005, vol. 102, No. 44, pp. 15815-15820.
Zhang D.D., et al., "Distinct Cysteine Residues in Keapl Are Required for Keapl-Dependent Ubiquitination of Nrf2 and for Stabilization of Nrf2 by Chemopreventive Agents and Oxidative Stress," Molecular and Cellular Biology, Nov. 2003, vol. 23, No. 22, pp. 8137-8151.
Zhang M., et al., "Emerging Roles of Nrf2 and Phase II Antioxidant Enzymes in Neuroprotection," Progress in Neurobiology, 2013, vol. 100, pp. 30-47.
Zhao B., et al., "A Thioether-Stabilized D-Proline-L-Proline Induced [Beta]-Hairpin Peptide of Defensin Segment Increases Its Anti-Candida Albicans Ability", ChemBioChem: A European Journal of Chemical Biology, 2016, vol. 17, No. 15, pp. 1416-1420, Published Online Jun. 20, 2016, XP055510467.
Zhao K., et al., "Enhanced Activity of Cyclic Transporter Sequences Driven by Phase Behavior of Peptide—lipid Complexes," Soft Matter, 2012, vol. 8, No. 24, pp. 6430-6433 (5 Pages).
Zhou H., et al., "Structure-Based Design of High-Affinity Macrocyclic Peptidomimetics to Block the Menin-Mixed Lineage Leukemia 1 (MLL1) Protein-Protein Interaction," Journal of Medicinal Chemistry, 2013, vol. 56, pp. 1113-1123.
Cardote, T.A.F. et al., "Cyclic and Macrocyclic Peptides as Chemical Tools to Recognize Protein Surfaces and Probe Protein-Protein Interactions," ChemMedChem, vol. 11, No. 8, pp. 787-794, 2016.
Cascales, L. et al., "Identification and Characterization of a New Family of Cell-Penetrating Peptides," Journal of Biological Chemistry, vol. 286, No. 42, pp. 36932-36943 (13 Pages), Oct. 21, 2011.
Cerrato, C.P. et al., "Novel Cell-Penetrating Peptide Targeting Mitochondria," The FASEB Journal, vol. 29, No. 11, pp. 4589-4599 (11 Pages), Nov. 2015.
Duchardt, F. et al., "A Cell-Penetrating Peptide Derived from Human Lactoferrin with Conformation-Dependent Uptake Efficiency," Journal of Biological Chemistry, vol. 284, No. 52, pp. 36099-36108, Dec. 25, 2009.
Futaki, S. et al., "Arginine-Rich Peptides. An Abundant Source of Membrane-Permeable Peptides Having Potential as Carriers for Intracellular Protein Delivery," The Journal of Biological Chemistry, vol. 276, No. 8, pp. 5836-5840 (6 Pages), Feb. 23, 2001.
Goncalves, E. et al., "Binding of Oligoarginine to Membrane Lipids and Heparan Sulfate: Structural and Thermodynamic Characterization of a Cell-Penetrating Peptide," Biochemistry, vol. 44, No. 7, pp. 2692-2702, 2005.
Li, Qian et al., "Arginine-rich membrane-permeable peptides are seriously toxic." Pharmacology research & perspectives 5.5, e00334, 5 pgs, 2017.
Lindgren, M. et al., "Classes and Prediction of Cell-Penetrating Peptides," Chapter 1 In: Cell-Penetrating Peptides: Methods and Protocols, Methods in Molecular Biology, Springer Science+ Business Media, LLC, vol. 683, pp. 3-19, 2011.
Noguchi, H. et al., "A New Cell-permeable Peptide Allows Successful Allogeneic Islet Transplantation in Mice," Nature Medicine, vol. 10, No. 3, pp. 305-309, Mar. 2004.
Pomilio, A.B. et al., "Naturally-Occurring Cyclopeptides: Structures and Bioactivity," Current Organic Chemistry, vol. 10, No. 16, pp. 2075-2121, Nov. 2006.
Qian, Z., "Developments and Applications of Cyclic Cell Penetrating Peptides" Dissertation; Ohio State University Graduate Program in chemistry; Embargoed until Oct. 2016.
Qian, Z. et al., "Structure-based Optimization of a Peptidyl Inhibitor Against Calcineurin-nuclear Factor of Activated T Cell (NFAT) Interaction," Journal of Medicinal Chemistry, vol. 57, No. 18, pp. 7792-7797, 2014.
Reissmann, Siegmund, "Cell penetration: scope and limitations by the application of cell penetrating peptides." Journal of Peptide Science 20.10, 760-784, 2014.
Rothbard et al., "Arginine-Rich Molecular Transporters for Drug Delivery: Role of Backbone Spacing in Cellular Uptake" J. Med Chem, pp. 3612-3618, 2002.

* cited by examiner

Molecular Weight: 1220.29

Molecular Weight: 1383.63

Molecular Weight: 1252.34

CYCLIC CELL PENETRATING PEPTIDES AND METHODS OF MAKING AND USING THEREOF

CROSS-REFERENCE TO RELATED APPLICATIONS

This application is a continuation of U.S. application Ser. No. 17/832,107, filed on Jun. 3, 2022, which is a continuation of U.S. application Ser. No. 16/462,920, filed May 21, 2019, which is a national stage application filed under 35 U.S.C. § 371 of PCT/US2017/063020 filed Nov. 22, 2017, which claims priority to U.S. Application No. 62/425,438, filed Nov. 22, 2016. The entirety of each of these applications is hereby incorporated by reference for all purposes.

STATEMENT REGARDING FEDERALLY FUNDED RESEARCH

This invention was made with government support under grant numbers GM062820, GM110208, and GM122459 awarded by the National Institutes of Health. The government has certain rights in the invention.

INCORPORATION BY REFERENCE

The Sequence Listing XML file named "25063-204US2_ST26" created on Sep. 15, 2025, and having a size of 461,725 bytes, is hereby incorporated by reference.

BACKGROUND

The plasma membrane presents a major challenge in drug discovery, especially for biologics such as peptides, proteins and nucleic acids. One potential strategy to subvert the membrane barrier and deliver the biologics into cells is to attach them to "cell-penetrating peptides" (CPPs). Since the initial observation that HIV trans-activator of transcription, Tat, internalizes into mammalian cells and activates viral replication in the late 1980s (Frankel, A D and Pabo, C O. *Cell,* 1988, 55, 1189-1193; Green, M and Loewenstein, P M. *Cell,* 1988, 55, 1179-1188) a large number of CPPs consisting of 6-20 residues have been reported (Langel, U. *Cell-penetrating peptides: methods and protocols*, Humana Press, New York, 2011, p xv; Schmidt, N et al. *FEBS Lett.,* 2010, 584, 1806-1813; Futaki, *S. Adv. Drug Delivery Rev.,* 2005, 57, 547-558; Stewart, K M et al. *Org. Biomol. Chem.,* 2008, 6, 2242-2255; Deshayes, S et al. *Cell. Mol. Life Sci.,* 2005, 62, 1839-1849; Goun, E A et al. *ChemBioChem,* 2005, 7, 1497-1515). CPPs have been used to deliver small-molecule drugs (Rothbard, J B et al. *Nat. Med.,* 2000, 6, 1253-1257; Nori, A et al. *Bioconjugate Chem.,* 2003, 14, 44-50), DNA (Hoyer, J and Neundorf, I. *Acc. Chem. Res.,* 2012, 45, 1048-1056; Eguchi, A et al. *J. Biol. Chem.,* 2001, 276, 26204-26210), RNA (Nakase, I et al. *Acc. Chem. Res.,* 2012, 45, 1132-1139; Andaloussi, S E et al. *Nucleic Acids Res.,* 2011, 39, 3972-3987; Jeong, J H et al. *Bioconjugate Chem.,* 2009, 20, 5-14; Muratovska, A and Eccles, M R. *FEBS Lett.,* 2004, 558, 63-68), proteins (Wadia, J S and Dowdy, S F. *Adv. Drug Delivery Rev.,* 2005, 57, 579-596; Pooga, M et al. *FASEB J.,* 2001, 15, 1451-1453; Schwarze, S R et al. *Science,* 1999, 285, 1569-1572), and nanoparticles (Josephson, L et al. *Bioconjugate Chem.,* 1999, 10, 186-191; Gupta, B et al. *Adv. Drug Delivery Rev.,* 2005, 57, 637-651; Liu, J et al. *Biomacromolecules,* 2001, 2, 362-8), into mammalian cells and tissues through either covalent attachment or electrostatic association. Many CPPs display minimal toxicity and immunogenicity at physiologically relevant concentrations (Saar, K et al. *Anal. Biochem.,* 2005, 345, 55-65; Suhorutsenko, J et al. *Bioconjugate Chem.,* 2011, 22, 2255-2262) and the incorporation of specific unnatural amino acids (Rueping, M et al. *ChemBioChem,* 2002, 3, 257-259) and other chemical moieties (Cooley, C B et al. *J. Am. Chem. Soc.,* 2009, 131, 16401-16403; Pham, W et al. *Chembiochem,* 2004, 5, 1148-1151) have been found to increase stability and cytosolic delivery.

Despite three decades of investigation, the fundamental basis for CPP activity remains incompletely defined. Two distinct and non-mutually exclusive mechanisms have been proposed for the CPPs whose primary sequences are characterized by having multiple arginine residues. In the first mechanism (direct membrane translocation), the arginine guanidinium groups interact with phospholipids of the plasma membrane to generate neutral ion pairs that passively diffuse across the membrane (Herce, H D and Garcia, A E. *Proc. Natl. Acad. Sci. U.S.A.,* 2007, 104, 20805-20810; Hirose, H et al. *Mol. Ther.,* 2012, 20, 984-993) or promote the formation of transient pores that permit the CPPs to traverse the lipid bilayer (Herce, H D et al. *Biophys. J.,* 2009, 97, 1917-1925; Palm-Apergi, C et al. *FASEB J.,* 2009, 23, 214-223). In the second mechanism, CPPs associate with cell surface glycoproteins and membrane phospholipids, internalize into cells through endocytosis (Richard, J P et al. *J. Biol. Chem.,* 2005, 280, 15300-15306; Ferrari, A et al. *Mol. Ther.,* 2003, 8, 284-294; Fittipaldi, A et al. *J. Biol. Chem.,* 2003, 278, 34141-34149; Kaplan, I M et al. *J. Controlled Release,* 2005, 102, 247-253; Nakase, I et al. *Biochemistry,* 2007, 46, 492-501) and subsequently exit from endosomes into the cytoplasm. It is now generally accepted that at low CPP concentrations, cellular uptake occurs mostly through endocytosis, whereas direct membrane translocation becomes prevalent at concentrations above 10 μM (Duchardt, F et al. Traffic, 2007, 8, 848-866). However, the mechanism(s) of entry and the efficiency of uptake may vary with the CPP identity, cargo, cell type, and other factors (Mueller, J et al. *Bioconjugate Chem.,* 2008, 19, 2363-2374; Maiolo, J R et al. *Biochim. Biophys. Acta.,* 2005, 1712, 161-172).

CPPs that enter cells via endocytosis must exit from endocytic vesicles in order to reach the cytosol. Unfortunately, the endosomal membrane has proven to be a significant barrier towards cytoplasmic delivery by these CPPs; often a negligible fraction of the peptides escapes into the cell interior (El-Sayed, A et al. *AAPS J.,* 2009, 11, 13-22; Varkouhi, A K et al. *J. Controlled Release,* 2011, 151, 220-228; Appelbaum, J S et al. (hem. Biol., 2012, 19, 819-830). For example, even in the presence of the fusogenic hemagglutinin peptide HA2, which has been demonstrated to enhance endosomal cargo release, >99% of a Tat-Cre fusion protein remains entrapped in macropinosomes 24 h after initial uptake (Kaplan, I M et al. *J. Controlled Release,* 2005, 102, 247-253). As a result, the first generation of CPPs have very low cytosolic delivery efficiencies, which is defined as the ratio of cytosolic over extracellular cargo concentrations. For example, Tat and R9, two of the most efficient as well as most widely used CPPs, have cytosolic delivery efficiencies of 1.9% and 4.4%, respectively (LaRochelle, J R et al., *J. Am. Chem. Soc.* 2015, 137, 2536-2541.).

Recently, two new types of CPPs with improved endosomal escape efficiencies have been discovered. Appelbaum et al. showed that folded miniature proteins containing a discrete penta-arginine motif were able to effectively overcome endosomal entrapment and reach the cytosol of mammalian cells (Appelbaum, J S et al. *Chem. Biol.,* 2012, 19, 819-830). This motif consists of five arginines across three turns of an α-helix, and proteins containing this motif were released from early (Rab5) endosomes into the cell interior. It has also been found that cyclization of certain arginine-rich CPPs enhances their cellular uptake (Qian, Z et al. *ACS Chem. Biol.,* 2013, 8, 423-431; Lattig-Tunnemann, G et al. *Nat. Commun.,* 2011, 2, 453; Mandal, D et al. *Angew. Chem. Int. Ed.,* 2011, 50, 9633-9637; Zhao, K et al. Soft Matter, 2012, 8, 6430-6433). Small amphipathic cyclic peptides such as cyclo (FΦRRRRQ) SEQ ID NO: 131 (cFΦ$R_4$, where Φ is L-2-naphthylalanine (SEQ ID NO: 6)) are internalized by mammalian cells in an energy-dependent manner, and enter the cytoplasm and nucleus with efficiencies 2-5-fold higher than that of nonaarginine ($R_9$; SEQ ID NO: 132) (Qian, Z et al. *ACS Chem. Biol.,* 2013, 8, 423-431). Moreover, membrane impermeable cargos such as phosphopeptides can be inserted into the cFΦ$R_4$ ring (SEQ ID NO: 6) resulting in their delivery into the cytoplasm of target cells. However, insertion of a cargo into the cyclic peptide ring, which is referred to herein as the "endocyclic" delivery method, is limited to relatively short peptides (≤13 amino acids), as large rings are conformationally flexible and have poor cell permeability and proteolytic stability (Qian, Z et al. *ACS Chem. Biol.,* 2013, 8, 423-431).

Introducing structural constraints to the ring has been shown to be effective for improving the efficiency of intracellular delivery. However, the previous method involved conversion of monocyclic peptides into bicyclic structures, in which one ring contains the CPP sequence while the other contains the target-binding sequence (Lian et al. *J. Am. Chem. Soc.* 2014, 136, 9830-9833). An alternative approach to increasing structural constraints and therefore the size of cyclic peptides for endocyclic delivery is to induce the formation of beta-hairpin structures. Previous studies have demonstrated that incorporation of a D-Pro-L-Pro motif into a cyclic peptide biases the cyclic peptide into a beta-hairpin structure, with the D-Pro-L-Pro motif located at one end of the beta-hairpin (Robinson, J A *Acc. Chem. Res.* 2008, 41, 1278-1288). Beta-hairpin peptides of this type have demonstrated utility in binding to biological targets such as proteins. However, unlike short cyclic peptides with a CPP motif, e.g., FΦ$R_4$ (SEQ ID NO:6), for endocyclic delivery (Qian, Z et al. *ACS Chem. Biol.* 2013, 8, 423-431; Qian, Z et al. *Biochemistry* 2016, 55, 2601-2612), peptides with beta-hairpin turns are impermeable to the cell membrane and therefore limited to targeting extracellular proteins. What is thus needed is an integrated sequence motif that promotes both the formation of beta-hairpin structures in cyclic peptides and efficient cellular uptake. A cyclic CPP of this type can allow efficient delivery of larger peptide cargos (>7 amino acids) by the endocyclic delivery method, because the D-Pro-L-Pro motif would bias the cyclic peptide to form a beta-hairpin structure, with the structured D-Pro-L-Pro/CPP motif at one end of the hairpin for efficient cellular entry and the other end for binding to specific target proteins. Cyclization of the integrated D-Pro-L-Pro/CPP motif in the absence of cargo motif would also provide novel CPP for exocyclic delivery of agents into various types of cells. Compositions and methods using such peptides for delivery of agents into various cell types. The compositions and methods disclosed herein address these and other needs.

SUMMARY

Disclosed herein are compounds having activity as cell penetrating peptides. The disclosed compounds have a beta-hairpin shaped cyclic structure that are cell-permeable and therefore capable of targeting intracellular proteins. In some examples, the compounds can comprise a cyclic structure with a cell penetrating peptide moiety, a beta-hairpin turn creating moiety, and a cargo moiety. The cargo moiety can comprise one or more detectable moieties, one or more therapeutic moieties, one or more targeting moieties, or any combination thereof. The beta-hairpin turn creating moiety can be -D-Pro-L-Pro- or -L-Pro-D-Pro-.

In some embodiments, the present disclosure provides for peptides comprising at least one beta-hairpin turn creating moiety and a cell-penetrating peptide moiety, wherein the peptide is delivered to the cytosol of a cell and binds to an intracellular target. In some embodiments, the beta-hairpin turn creating moiety is -D-Pro-L-Pro-; -L-Pro-D-Pro-; an intramolecular disulfide bond; a sequence comprising anachiral α-aminoisobutyric acid residue in combination with either a D-α-amino acid residue or an achiral α-amino acid residue; an azobenzene residue; a sequence comprising a plurality of tryptophan residues; or an amino acid sequence comprising an azobenzene. In some embodiments, the cell penetrating peptide moiety is a sequence listed in Table 2. In some embodiments, the beta-hairpin turn creating moiety is located within an amino acid sequence comprising the cell penetrating peptide moiety.

In some embodiments, the peptides disclosed herein have a structure according to Formula I:

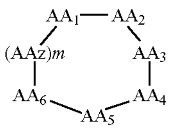

(I)

wherein:

$AA_1$, $AA_2$, $AA_3$, $AA_4$, $AA_5$, and $AA_6$ are each, independently, an amino acid, which is optionally substituted;

AAz, at each instance and when present, is independently an amino acid, which is optionally substituted;

m is an integer from 0 to 50; and wherein:

any two adjacent amino acid residues are a beta-hairpin turn creating moiety of -D-Pro-L-Pro- or -L-Pro-D-Pro;

at least two amino acid residues are an arginine residue; and and at least two amino residue have a hydrophobic side chain.

In some embodiments, the peptides disclosed herein (e.g., the peptides of Formula I) have any one of the following structures:

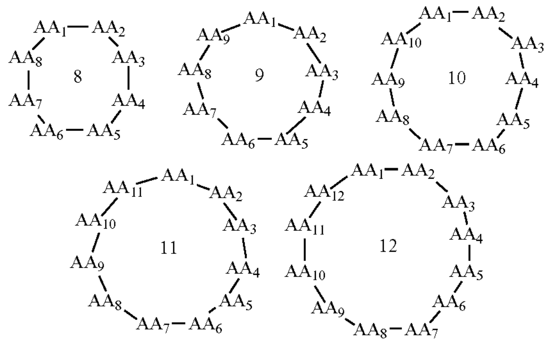

-continued

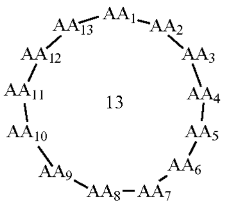

13

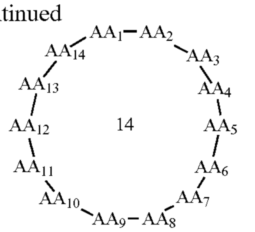

14

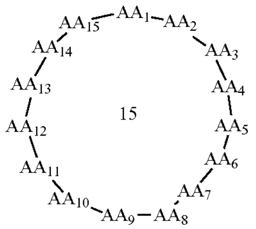

15

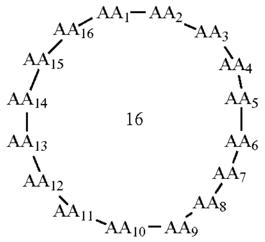

16

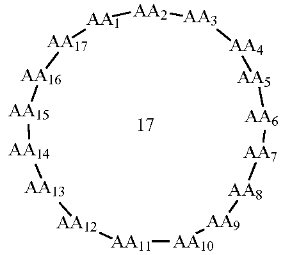

17

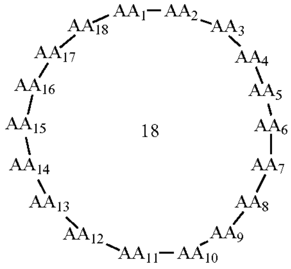

18 wherein $AA_1$, $AA_2$, $AA_3$, $AA_4$, $AA_5$, $AA_6$, $AA_7$, $AA_8$, $AA_9$, $AA_{10}$, $AA_{11}$, $AA_{12}$, $AA_{13}$, $AA_{14}$, $AA_{15}$, $AA_{16}$, $AA_{17}$, and $AA_{18}$ are amino acid residues, each of which is optionally substituted; and wherein:

any two adjacent amino acid residues are a beta-hairpin turn creating moiety of -D-Pro-L-Pro- or -L-Pro-D-Pro;

at least two amino acid residues are an arginine residue; and and at least two amino residue have a hydrophobic side chain.

In all of these structures, any two adjacent amino acid residues are the beta-hairpin turn creating moiety -D-Pro-L-Pro- or -L-Pro-D-Pro-. For example, $-AA_1-AA_2-$, $-AA_2-AA_3-$, $-AA_3-AA_4-$, $-AA_4-AA_5-$, $-AA_5-AA_6-$, $-AA_6-AA_7-$, $-AA_7-AA_8-$, $-AA_8-AA_9-$, $-AA_9-AA_{10}-$, $-AA_{10}-A_{11}-$, $-A_{11}AA_{12}-$, $-AA_{12}-AA_{13}-$, $-AA_{13}-AA_{14}-$, $-AA_{14}-AA_{15}-$, $-AA_{15}-AA_{16}-$, $-AA_{16}-AA_{17}-$, $-AA_{17}-AA_{18}-$, $-AA_{18}-AA_1-$, $-AA_{17}-AA_1-$, $-AA_{16}-AA_1-$, $-AA_{15}-AA_1-$, $-AA_{14}-AA_1-$, $-AA_{13}-AA_1-$, $-AA_{12}-AA_1-$, $-AA_{11}-AA_1-$, $-AA_{10}-AA_1-$, $-AA_9-AA_1-$, or $-AA_8-AA_1-$can be -D-Pro-L-Pro- or -L-Pro-D-Pro-.

In some embodiments, at least three amino acid residues are arginine residues. In some embodiments, at least four amino acid residues are arginine residues. In some embodiments, at least three amino acids have a hydrophobic side chain. In some embodiments, the hydrophobic side chain comprises an aromatic ring. In some embodiments, the amino acids having a hydrophobic side chain are independently phenylalanine, naphthylalanine, or tryptophan, each of which is optionally substituted. In some embodiments, the peptides disclosed herein comprise at least two arginine residues and at least three amino acids having a hydrophobic side chain.

In some embodiments, one arginine residue is within 2 amino acid residues of another arginine residue. In some embodiments, the two arginine residues are consecutive. In some embodiments, the peptides disclosed herein comprise at least three arginine residues, wherein at least two arginine residues are consecutive. In some embodiments, the peptides disclosed herein comprise at least four arginine residues, wherein at least three arginine residues are consecutive.

In some embodiments, one amino acid residue which has a hydrophobic side chain is within 2 amino acid residues of another amino acid residue which has a hydrophobic side chain. In some embodiments, two amino acids which have a hydrophobic side chain are consecutive. In some embodiments, the peptides disclosed herein comprise at least three amino acids which have a hydrophobic side chain, wherein at least two amino acids having a hydrophobic side chain are consecutive.

In some embodiments, the peptides disclosed herein comprise at least one amino acid, in addition to D-Pro when present, which is a D amino acid. In some embodiments, the peptides disclosed herein comprise at least two amino acids, in addition to the D-Pro-L-Pro motif when present, which have alternating chirality. In some embodiments, at least three consecutive amino acids have alternating chirality. In some embodiments, at least four consecutive amino acids have alternating chirality. In some embodiments, the amino acids having alternating chirality are arginine residues. In some embodiments, the peptides disclosed herein comprise a sequences selected from SEQ ID NO: 1 to SEQ ID NO:79 or SEQ ID NO: 172 to SEQ ID NO: 197.

Additionally, in any of these structures, there is a cell penetrating peptide moiety. This moiety can be at least 4 amino acids in length. In the cell penetrating moiety there are at least one, at least two, or more specifically, at least three arginine (R) residues. Further, in these moieties there are at least one, at least two, or at least three hydrophobic residues, for example, 3-benzothienyl-L-alanine, phenylalanine, naphthylalanine, tryptophan, or an analog or derivative thereof. For example, there can be 1 arginine and 5 hydrophobic residues like 3-benzothienyl-L-alanine, phenylalanine, naphthylalanine, tryptophan, or an analog or derivative thereof, 2 arginine and 4 hydrophobic residues, e.g. 3-benzothienyl-L-alanine, phenylalanine, naphthylalanine, tryptophan, or an analog or derivative thereof, 3 arginine and 3 hydrophobic residues, e.g. 3-benzothienyl-L-alanine, phenylalanine, naphthylalanine, tryptophan, or an analog or derivative thereof, 4 arginine and 2 hydrophobic residues, e.g. 3-benzothienyl-L-alanine, phenylalanine, naphthylalanine, tryptophan, or an analog or derivative thereof, or 4 arginine and 1 hydrophobic residue, e.g. 3-benzothienyl-L-alanine, phenylalanine, naphthylalanine, tryptophan, or an analog or derivative thereof. In a specific example, the cyclic compunds disclosed herein have 3 arginines and 3 hydrophobic residues, e.g. 3-benzothienyl-L-alanine, phenylalanine, naphthylalanine, tryptophan, or an analog or derivative thereof. Further the arginine residues can be clustered, e.g., an arginine is within 2 amino acids of another arginine residue. Likewise, the hydrophobic residues can be clustered, e.g., one hydrophobic residue is with 2 amino acids of another hydrophobic residue.

In some embodiments, the peptides disclosed herein further comprise a cargo moiety. In some embodiments, the cargo moiety, together with the cell penetrating peptide moiety and beta-hairpin turn creating moiety, are all part of the cyclic peptide. In some embodiments, the cargo moiety is conjugated to a side chain of an amino acid in the peptide. In some embodiments, the cargo moiety is conjugated to the side chain of a glutamine in the peptide. In some embodiments, the cargo moiety comprises a targeting moiety.

In some examples, the cell penetrating peptide moiety, beta-hairpin turn creating moiety, and cargo moiety together are all part of the cyclic compound; this is referred to herein as an "endocyclic" configuration. Thus, cargo sequences can comprise part of the cycle, in addition to the beta-hairpin turn creating moiety and the cell penetrating peptide moiety.

Alternatively, in some examples, the cell penetrating peptide moiety and beta-hairpin turn creating moiety are part of the cyclic compound and the cargo moiety is appended to the cyclic compound; this is referred to herein as an "exocyclic" configuration. That is, the cargo amino acid sequences or moiety can be attached to any of the side chain residues ($AA_1$-$AA_{18}$) or peptide nitrogens in the disclosed cyclic compounds. The cargo moiety can also be a cyclic moiety itself that is fused to the cyclic beta-hairpin shaped CPP compounds disclosed herein. These are referred to as a "bicyclic" configuration.

The amino acids in the disclosed compounds can be coupled by a peptide bond. Additionally, some or all of the amino acids in the disclosed compounds can be coupled at the side chain of an adjacent amino acid residue.

The cargo moiety can comprise any cargo of interest, for example a linker moiety, a detectable moiety, a therapeutic moiety, a targeting moiety (e.g., a sequence listed in Table 5), and the like, or any combination thereof.

The cargo moiety can be attached to the cyclic peptides at the amino group, the carboxylate group, or the side chain of any of the amino acids of the cell penetrating peptide moiety (e.g., at the amino group, the carboxylate group, or the side chain or any of $AA_1$-$AA_{18}$).

In some examples, the cargo moiety comprises a targeting moiety. The targeting moiety can comprise, for example, a sequence of amino acids that can target one or more enzyme domains. In some examples, the targeting moiety can comprise an inhibitor against a protein that can play a role in a disease, such as cancer, cystic fibrosis, diabetes, obesity, or combinations thereof. In some examples, the therapeutic moiety can comprise a targeting moiety that can act as an inhibitor against Ras (e.g., K-Ras), PTP1B, Pin1, Grb2 SH2, CAL PDZ, and the like, or combinations thereof.

Also disclosed herein are compositions that comprise the compounds described herein. Also disclosed herein are pharmaceutically-acceptable salts and prodrugs of the disclosed compounds.

Also provided herein are methods of use of the compounds or compositions described herein. Also provided herein are methods for treating a disease or pathology in a subject in need thereof comprising administering to the subject an effective amount of any of the compounds or compositions described herein.

Also provided herein are methods of treating, preventing, or ameliorating cancer in a subject. The methods include administering to a subject an effective amount of one or more of the compounds or compositions described herein, or a pharmaceutically acceptable salt thereof. The methods of treatment or prevention of cancer described herein can further include treatment with one or more additional agents (e.g., an anti-cancer agent or ionizing radiation).

Also described herein are methods of killing a tumor cell in a subject. The method includes contacting the tumor cell with an effective amount of a compound or composition as described herein, and optionally includes the step of irradiating the tumor cell with an effective amount of ionizing radiation. Additionally, methods of radiotherapy of tumors are provided herein. The methods include contacting the tumor cell with an effective amount of a compound or composition as described herein, and irradiating the tumor with an effective amount of ionizing radiation.

In some examples of the methods of treating of treating, preventing, or ameliorating cancer or a tumor in a subject, the compound or composition administered to the subject can comprise a therapeutic moiety that can comprise a targeting moiety that can act as an inhibitor against Ras (e.g., K-Ras), PTP1B, Pin1, Grb2 SH2, or combinations thereof.

The disclosed subject matter also concerns methods for treating a subject having a metabolic disorder or condition. In one embodiment, an effective amount of one or more compounds or compositions disclosed herein is administered to a subject having a metabolic disorder and who is in need of treatment thereof. In some examples, the metabolic disorder can comprise type II diabetes. In some examples of the methods of treating of treating, preventing, or ameliorating the metabolic disorder in a subject, the compound or composition administered to the subject can comprise a therapeutic moiety that can comprise a targeting moiety that can act as an inhibitor against PTP1B.

The disclosed subject matter also concerns methods for treating a subject having an immune disorder or condition. In one embodiment, an effective amount of one or more compounds or compositions disclosed herein is administered to a subject having an immune disorder and who is in need of treatment thereof. In some examples of the methods of treating of treating, preventing, or ameliorating the immune disorder in a subject, the compound or composition administered to the subject can comprise a therapeutic moiety that can comprise a targeting moiety that can act as an inhibitor against Pin1.

The disclosed subject matter also concerns methods for treating a subject having cystic fibrosis. In one embodiment, an effective amount of one or more compounds or compositions disclosed herein is administered to a subject having cystic fibrosis and who is in need of treatment thereof. In some examples of the methods of treating the cystic fibrosis in a subject, the compound or composition administered to the subject can comprise a therapeutic moiety that can comprise a targeting moiety that can act as an inhibitor against CAL PDZ.

The disclosed subject matter also concerns methods of delivering compound to a cardiomyocyte, comprising: contacting the cardiomycte with an effective amount of a one or more compounds or compositions disclosed herein.

Also described herein is a cell comprising one or more peptides disclosed herein. Additionally, provided herein are methods of making one or more peptides disclosed herein.

The details of one or more embodiments of the invention are set forth in the accompanying drawings and the description below. Other features, objects, and advantages of the invention will be apparent from the description and drawings, and from the claims.

DESCRIPTION OF FIGURES

The accompanying Figures, which are incorporated in and constitute a part of this specification, illustrate several aspects described below.

FIG. 9(*b*) shows inhibition of the binding of Grb2 SH2 domain to a fluorescently labeled peptide (FIG. 10) by BH23, as monitored by a fluorescence polarization assay.

FIG. 9(*c*) shows confocal microscopic images of HeLa cells after treatment with 5 μM BH23-FAM for 2 h (1% FBS). I, DIC; II, GFP channel; III, overlap of I and II.

FIG. 10(*b*) shows its binding to Grb2 SH2 domain as monitored by fluorescence anisotropy ($K_d$=92 nM). This ligand was used as reporter ligand in FA/FP-based competition assays to determine the binding affinities of new Grb2 SH2 domain ligands.

FIG. 11 also provides a binding curve, which shows BH24's inability to compete with the fluorescently labeled reporter ligand in FIG. 10 for binding to the Grb2 SH2 domain.

FIG. 12 also provides a graph showing BH25 competition for binding to the Grb2 SH2 domain with the fluorescently labeled reporter ligand in FIG. 10. The IC50 value (0.10 μM) may be over- or underestimated by up to 2-fold, due to the fact the peptide concentration was estimated by dissolving a known mass of peptide (after lyophilization) into a known volume of solvent.

FIG. 14(*b*) provides western blots showing the effect of peptides BH23 and BH26 on the Grb2/Ras signaling pathway. MDA-MB-468 cells were treated with the indicated concentrations of BH23 or BH26 for 2 h and stimulated with EGF (50 ng/mL) for 10 min. The cells were then lysed and the cell lysates were separated on SDS-PAGE and blotted with antibodies specific for phosphorylated and total kinases in the Ras signaling pathway.

DETAILED DESCRIPTION

Figure 1:
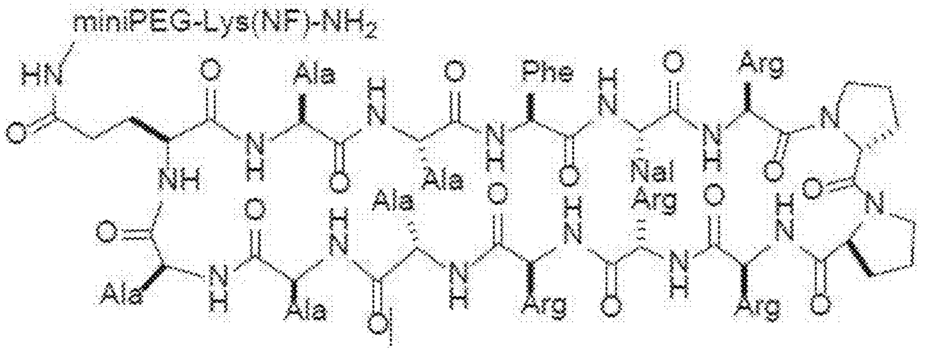
FIG. 1 is the structure of cyclic B-hairpin peptide BH1.

The compounds, compositions, and methods described herein may be understood more readily by reference to the following detailed description of specific aspects of the disclosed subject matter and the Examples and Figures included therein.

Before the present compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human. Thus, the subject can be a human or veterinary patient. The term "patient" refers to a subject under the treatment of a clinician, e.g., physician.

The term "inhibit" refers to a decrease in an activity, response, condition, disease, or other biological parameter. This can include but is not limited to the complete ablation of the activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed. For example, the terms "prevent" or "suppress" can refer to a treatment that forestalls or slows the onset of a disease or condition or reduced the severity of the disease or condition. Thus, if a treatment can treat a disease in a subject having symptoms of the disease, it can also prevent or suppress that disease in a subject who has yet to suffer some or all of the symptoms.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "anticancer" refers to the ability to treat or control cellular proliferation and/or tumor growth at any concentration.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The terms "peptide," "protein," and "polypeptide" are used interchangeably to refer to a natural or synthetic molecule comprising two or more amino acids linked by the carboxyl group of one amino acid to the alpha amino group of another.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more $—OCH_2CH_2O—$ units in the polyester, regardless of whether ethylene glycol was used to prepare the polyester. Similarly, a sebacic acid residue in a polyester refers to one or more $—CO(CH_2)_8CO—$ moieties in the polyester, regardless of whether the residue is obtained by reacting sebacic acid or an ester thereof to obtain the polyester. As another example, an amino acid residue, e.g., in a peptide, refers to one or more -AA- moieties, and such residues may be referred to herein interchangibly as an amino acid or an amino acid residue.

As described herein, compounds can contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group can have a suitable substituent at each substitutable position of the group, and when more than one position in any given structure can be substituted with more than one substituent selected from a specified group, the substituent can be either the same or different at every position. Combinations of substituents envisioned herein are preferably those that result in the formation of stable or chemically feasible compounds. In is also contemplated that, in some examples, unless expressly indicated to the contrary, individual substituents can be further optionally substituted (i.e., further substituted or unsubstituted).

As used herein, the term "substituted" is contemplated to include all permissible substituents of organic compounds. In some examples, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain examples, unless expressly indicated to the contrary, individual substituents can be further optionally substituted (i.e., further substituted or unsubstituted).

Suitable monovalent substituents on a substitutable carbon atom of an "optionally substituted" group are independently halogen; $-(CH_2)_{0-4}R^o$; $-O(CH_2)_{0-4}R^o$, $-O-(CH_2)_{0-4}C(O)OR^o$; $-(CH_2)_{0-4}CH(OR^o)_2$; $-(CH2)_{0-4}SR^o$; $-(CH_2)_{0-4}Ph$, which may be substituted with $R^o-(CH_2)_{0-4}O(CH_2)_{0-1}Ph$ which may be substituted with $R^o$; $-CH{=}CHPh$, which may be substituted with $R^o$; $-(CH_2)_{0-4}O(CH_2)_{0-1}$-pyridyl which may be substituted with $R^o$; $-NO_2$; $-CN$; $-N_3$; $-(CH_2)_{0-4}N(R^o)_2$; $-(CH_2)_{0-4}N(R^o)C(O)R^o$; $-N(R^o)C(S)R^o$; $-(CH_2)_{0-4}N(R^o)C(O)NR^o_2$; $-N(R^o)C(S)NR^o_2$; $-(CH_2)_{0-4}N(R^o)C(O)OR^o$; $-N(R^o)N(R^o)C(O)R^o$; $-N(R^o)N(R^o)C(O)NR^o_2$; $-N(R^o)N(R^o)C(O)OR^o$; $-(CH_2)_{0-4}C(O)R^o$; $-C(S)R^o$; $-(CH_2)_{0-4}C(O)OR^o$; $-(CH_2)_{0-4}C(O)SR^o$; $-(CH_2)_{0-4}C(O)OSiR^o_3$; $-(CH_2)_{0-4}OC(O)R^o$; $-OC(O)(CH_2)_{0-4}SR-$, $SC(S)SR^o$; $-(CH_2)_{0-4}SC(O)R^o$; $-(CH_2)_{0-4}C(O)NR^o_2$; $-C(S)NR^o_2$; $-C(S)SR^o$; $-SC(S)SR^o$, $-(CH_2)_{0-4}OC(O)NR^o_2$; $-C(O)N(OR^o)R^o$; $-C(O)C(O)R^o$; $-C(O)CH_2C(O)R^o$; $-C(NOR^o)R^o$; $-(CH_2)_{0-4}SSR^o$; $-(CH_2)_{0-4}S(O)_2R^o$; $-(CH_2)_{0-4}S(O)_2OR^o$; $-(CH_2)_{0-4}OS(O)_2R^o$; $-S(O)_2NR^o_2$; $-(CH_2)_{0-4}S(O)R^o$; $-N(R^o)S(O)_2NR^o_2$; $-N(R^o)S(O)_2R^o$; $-N(OR^o)R^o$; $-C(NH)NR^o_2$; $-P(O)_2R^o$; $-P(O)R^o_2$; $-OP(O)R^o_2$; $-OP(O)(OR^o)_2$; $SiR^o_3$; $-(C_{1-4}$ straight or branched alkylene$)O-N(R^o)_2$; or $-(C_{1-4}$ straight or branched) alkylene$)C(O)O-N(R^o)_2$, wherein each $R^o$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^o$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^o$ (or the ring formed by taking two independent occurrences of $R^o$ together with their intervening atoms), are independently halogen, $-(CH_2)_{0-2}R^\bullet$, -(haloR•), $-(CH_2)_{0-2}OH$, $-(CH_2)O_2OR^\bullet$, $-(CH_2)_{0-2}CH(OR^\bullet)_2$; $-O$(haloR•, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR$, $-(C_{1-4}$ straight or branched alkylene$)C(O)OR$; or $-SSR^\bullet$ wherein each R• is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R• include ═O and ═S.

Suitable divalent substituents on a saturated carbon atom of an "optionally substituted" group include the following: ═O, ═S, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, OR•, —O(haloR•), —CN, —C(O)OH, —C(O)OR•, $-NH_2$, —NHR•, $-NR^\bullet_2$, or $-NO_2$, wherein each R• is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, $-NR^\dagger_2$, —C(O)R†, —C(O)OR†, —C(O)C(O)R†, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each R† is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, $-NH_2$, —NHR•, $-NR^\bullet_2$, or $-NO_2$, wherein each R• is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

Disclosed herein are compounds (i.e., also referred to interchangibly herein as peptides) having activity as cell penetrating peptides and inhibitors of protein-protein interactions. The disclosed compounds have a beta-hairpin shaped cyclic structure and are cell-permeable, and therefore capable of targeting intracellular proteins. Moreover, a beta-hairpin shaped cyclic cell penetrating peptide can be fused with a wide variety of target-binding sequences to generate cell-permeable cyclic peptide ligands against different intracellular targets.

In some examples, the compounds are cyclic peptides comprising a cell penetrating peptide moiety, a beta-hairpin turn creating moiety, and optionally a cargo moiety. As used herein, a "cell penetrating peptide moiety" refers to an amino acid sequence which is able to traverse a cell membrane and enter the cytosol. As discussed in detail below, in various embodiments, the cell penetrating peptide moiety may comprise at least one arginine residue and at least one amino acid residue having a hydrophobic side chain. The cargo moiety can comprise one or more detectable moieties, one or more therapeutic moieties, one or more targeting moieties, or any combination thereof. In some embodiments, the beta-hairpin turn creating moiety can be -D-Pro-L-Pro- or -L-Pro-D-Pro-.

In some embodiments, the cyclic peptides described herein have a structure according to Formula I:

(I)

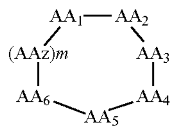

In some embodiments, $AA_1$, $AA_2$, $AA_3$, $AA_4$, $AA_5$, and $AA_6$ are each, independently, an amino acid. In some embodiments, AAz, at each instance and when present, is independently an amino acid. In some embodiments, m is an integer from 0 to 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, and 49, inclusive of all values and subranges therebetween. In particular embodiments, the m is an integer in the range of from 0-24.

In some embodiments, the cyclic peptides of Formula I comprise at least one beta-hairpin turn creating moiety, e.g., 2, 3, 4, 5, 6, 7, 8, 9, or 10 or more beta-hairpin turn creating moieties, inclusive of all ranges therein.

In some embodiments, the cyclic peptides of Formula I comprise cell penetrating peptide moiety. The cell penetrating peptide moiety can be a contiguous sequence of amino acids, or the amino acids, which comprise the cell-penetrating moiety, can be separated by a beta hairpin turn creating moiety.

Each amino acid can be a natural or non-natural amino acid. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Non-natural amino acids can also be the D-isomer of the natural amino acids. Thus, as used herein, the term "amino acid" refers to natural and non-natural amino acids, and analogs and derivatives thereof. Examples of suitable amino acids include, but are not limited to, alanine, allosoleucine, arginine, asparagine, aspartic acid, cysteine, glutamine, glutamic acid, glycine, histidine, isoleucine, leucine, lysine, methionine, napthylalanine, phenylalanine, proline, pyroglutamic acid, serine, threonine, tryptophan, tyrosine, valine, a derivative, or combinations thereof. These, and others, are listed in the Table 1 along with their abbreviations used herein.

TABLE 1

| Amino Acid Abbreviations | | |
|---|---|---|
| Amino Acid | Abbreviations* L-amino acid | Abbreviations* D-amino acid |
| Alanine | Ala (A) | ala (a) |
| Allosoleucine | AIle | aile |
| Arginine | Arg (R) | arg (r) |
| Asparagine | Asn (N) | asn (n) |
| aspartic acid | Asp (D) | asp (d) |
| Cysteine | Cys (C) | cys (c) |
| Cyclohexylalanine | Cha | cha |
| 2,3-diaminopropionic acid | Dap | dap |
| 4-fluorophenylalanine | Fpa (Σ) | fpa |
| Glutamic acid | Glu (E) | glu (e) |
| Glutamine | Gln (Q) | gln (q) |
| Glycine | Gly (G) | gly (g) |
| Histidine | His (H) | his (h) |
| Homoproline (aka pipecolic acid) | Pip (Θ) | pip (θ) |
| Isoleucine | Ile (I) | ile (i) |
| Leucine | Leu (L) | leu (l) |
| Lysine | Lys (K) | lys (k) |
| Methionine | Met (M) | met (m) |
| Napthylalanine | Nal (Φ) | nal (ϕ) |
| Norleucine | Nle (Ω) | nle |
| Phenylalanine | Phe (F) | phe (F) |
| Phenylglycine | Phg (Ψ) | Phg |
| 4-(phosphonodifluoromethyl) phenylalanine | $F_2$Pmp (Λ) | $f_2$pmp |
| Proline | Pro (P) | pro (p) |
| Sarcosine | Sar (Ξ) | sar |
| Selenocysteine | Sec (U) | sec (u) |
| Serine | Ser (S) | ser (s) |
| Threonine | Thr (T) | thr (y) |
| Tyrosine | Tyr (Y) | tyr (y) |
| Tryptophan | Trp (W) | trp (w) |
| Valine | Val (V) | val (v) |
| 2,3-diaminopropionic acid | Dap | dap |

*single letter abbreviations: when shown in capital letters herein it indicates the L-amino acid form, when shown in lower case herein it indicates the D-amino acid form The amino acids can be coupled by a peptide bond. The amino acids can be coupled to the cargo moiety, when present, at the amino group, the carboxylate group, or the side chain.

The amino acids may also be substituted with one or more substituent as described herein. The substituents can be selected to improve the activity of the cyclic peptide. For example, hydrophobic amino acid can be substituted with a halogen or a hydrophobic substituent to increase cellular uptake efficiency. In other examples, the beta-hairpin turn creating motif can be substituted with a substituent that increases the strength of the hydrogen bonding interaction that creates the beta-hairpin turn.

In some embodiments, the cyclic peptides disclosed herein comprise at least one D amino acid, e.g., in the CPP moiety sequence. In other embodiments, the peptides comprise at least two D amino acids, at least three D amino acids, or at least four D amino acids. Certain embodiments include amino acid sequences (e.g., a cell penetrating peptide moiety) wherein at least four consecutive amino acids have alternating chirality. As used herein, chirality refers to the "D" and "L" isomers of amino acids. In particular embodiments, at least four consecutive amino acids have alternating chirality and the remaining amino acids are L-amino acids. In other embodiments, the peptides of comprise a four amino acid sequence having D-L-D-L chirality. In still other embodiments, the peptides of the invention comprise a four amino acid sequence having L-D-L-D chirality.

In embodiments, peptides comprise two consecutive L-amino acids. In further embodiments, the peptides comprise two consecutive L-amino acids separating two D-amino acids. In yet further embodiments, the peptides comprise two consecutive L-amino acids separating two D-amino acids and at least four consecutive amino acids having alternating chirality, such as, but not limited to peptide sequences with D-L-L-D-L-D or L-D-L-L-D-L-D chirality. In even further embodiments, the peptides comprise two consecutive L-amino acids separating two D-amino acids and at least five consecutive amino acid having alternating chirality, such as, but not limited to peptide sequences with D-L-L-D-L-D-L or L-D-L-L-D-L-D-L chirality.

In embodiments, the peptides comprise two consecutive D-amino acids. In further embodiments, the peptides comprise two consecutive D-amino acids separating two L-amino acids. In still further embodiments, the peptides comprise two consecutive D-amino acids separating two L-amino acids and at least four consecutive amino acids having alternating chirality, such as, but not limited to peptide sequences with L-D-D-L-D-L. In even further embodiments, the peptides comprise two consecutive D-amino acids separating two L-amino acids and at least five consecutive amino acids having alternating chirality, such as, but not limited to peptide sequences with L-D-D-L-D-L-D.

In some embodiments, the amino acid sequence with alternating chirality comprises about at least about 4 amino acids, at least about 5 amino acids, at least about 6 amino acids, at least about 7 amino acids, at least about 8 amino acids or at least about 9 amino acids. In embodiments, the amino acid sequence with alternating chirality comprises of from about 4 amino acids to about 9 amino acids, or about 5 amino acids to about 6 amino acids, or about 7 amino acids to about 9 amino acids, or about 8 amino acids to about 9 amino acids, or about 4 amino acids to about 8 amino acids, or about 4 amino acids to about 7 amino acids, or about 4 amino acids to about 6 amino acids, or about 4 amino acids to about 5 amino acids.

The chirality of the amino acid residues in the cyclic peptides disclosure herein can be selected to improve cytosolic delivery efficiency. In some embodiments, the presence of one or more D-amino acids in the cyclic peptide improves the cytosolic delivery efficiency by about 1.1 fold to about 30 fold, compared to an otherwise identical sequence, e.g., about 1.2, about 1.3, about 1.4, about 1.5, about 1.6, about 1.7, about 1.8, about 1.9, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 10, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, about 20, about 20.5, about 21.0, about 21.5, about 22.0, about 22.5, about 23.0, about 23.5, about 24.0, about 24.5, about 25.0, about 25.5, about 26.0, about 26.5, about 27.0, about 27.5, about 28.0, about 28.5, about 29.0, or about 29.5 fold, inclusive of all values and subranges therebetween.

In some embodiments, an arginine residue has the same chirality the neighboring proline residue. In some embodiments, the presence of an arginine having the same chirality as the neighboring proline residue improves the cytosolic delivery efficiency by about 1.1 fold to about 30 fold, compared to an otherwise identical sequence, e.g., about 1.2, about 1.3, about 1.4, about 1.5, about 1.6, about 1.7, about 1.8, about 1.9, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 10, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, about 20, about 20.5, about 21.0, about 21.5, about 22.0, about 22.5, about 23.0, about 23.5, about 24.0, about 24.5, about 25.0, about 25.5, about 26.0, about 26.5, about 27.0, about 27.5, about 28.0, about 28.5, about 29.0, or about 29.5 fold, inclusive of all values and subranges therebetween.

In some examples, the disclosed cyclic peptides of Formula I can have any one of the following structures:

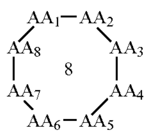
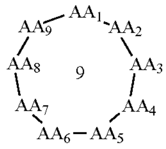
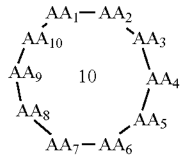
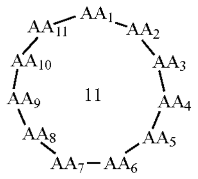
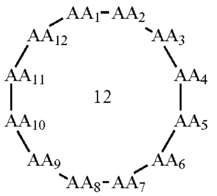
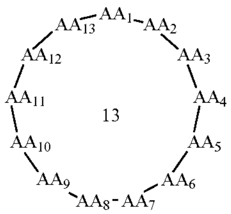
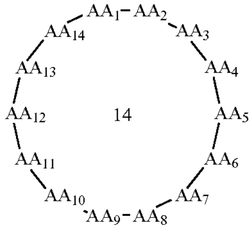
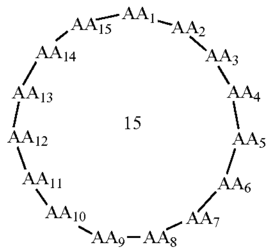
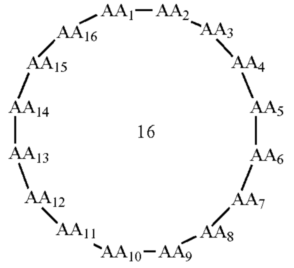

-continued

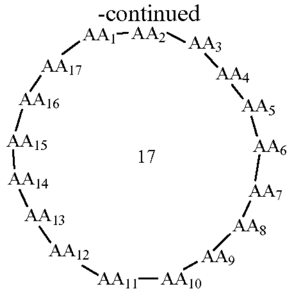

17

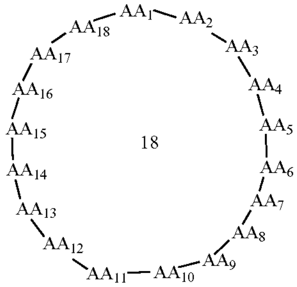

18 wherein $AA_1$, $AA_2$, $AA_3$, $AA_4$, $AA_5$, $AA_6$, $AA_7$, $AA_8$, $AA_9$, $AA_{10}$, $AA_{11}$, $AA_{12}$, $AA_{13}$, $AA_{14}$, $AA_{15}$, $AA_{16}$, $AA_{17}$, and $AA_{18}$ (i.e., $AA_1$-$AA_{18}$) are each, independently, an amino acid. These structures represent cyclic peptide having from 8 to 18 amino acid residues. In any of these structures, any two adjacent amino acid residues are the beta-hairpin turn creating moiety -D-Pro-L-Pro- or -L-Pro-D-Pro-. For example, $-AA_1-AA_2-$, $-AA_2-AA_3-$, $-AA_3-AA_4-$, $-AA_4-AA_5-$, $-AA_5-AA_6-$, $-AA_6-AA_7-$, $-AA_7-AA_8-$, $-AA_8-AA_9-$, $-AA_9-AA_{10}-$, $-AA_{10}-A_{11}-$, $-A_{11}AA_{12}-$, $-AA_{12}-AA_{13}-$, $-AA_{13}-AA_{14}-$, $-AA_{14}-AA_{15}-$, $-AA_{15}-AA_{16}-$, $-AA_{16}-AA_{17}-$, $-AA_{17}-AA_{18}-$, $-AA_{18}-AA_1-$, $-AA_{17}-AA_1-$, $-AA_{16}-AA_1-$, $-AA_{15}-AA_1-$, $-AA_{14}-AA_1-$, $-AA_{13}-AA_1-$, $-AA_{12}-AA_1-$, $-AA_{11}-AA_1-$, $-AA_{10}-AA_1-$, $-AA_9-AA_1-$, or $-AA_8-AA_1-$ can be -D-Pro-L-Pro- or -L-Pro-D-Pro-.

Additionally, in any of these structures, there is a cell penetrating peptide moiety. This moiety can be at least 4 amino acids in length, e.g., 5, 6, 7, 8, 9, or 10 amino acids in length. In the cell penetrating moiety there are at least one, at least two, or at least three arginine (R) residues. Further, in these structures there are at least one, at least two, or at least three amino acids having hydrophobic side chains, for example, any amino acid described below, including 3-benzothienyl-L-alanine, phenylalanine, naphthylalanine, tryptophan, or an analog or derivative thereof. For example, there can be 1 arginine and 5 amino acids having hydrophobic side chains, e.g., 3-benzothienyl-L-alanine, phenylalanine, naphthylalanine, tryptophan, or an analog or derivative thereof; 2 arginine and 4 amino acids having hydrophobic side chains, e.g., 3-benzothienyl-L-alanine, phenylalanine, naphthylalanine, tryptophan, or an analog or derivative thereof; 3 arginine and 3 amino acids having hydrophobic side chains, e.g., 3-benzothienyl-L-alanine, phenylalanine, naphthylalanine, tryptophan, or an analog or derivative thereof; 4 arginine and 2 amino acids having hydrophobic side chains, e.g., 3-benzothienyl-L-alanine, phenylalanine, naphthylalanine, tryptophan, or an analog or derivative thereof; or 4 arginine and 1 amino acids having hydrophobic side chains, e.g., 3-benzothienyl-L-alanine, phenylalanine, naphthylalanine, tryptophan, or an analog or derivative thereof. In a specific example, the cyclic compunds disclosed herein have 3 arginines and 3 amino acids having hydrophobic side chains, e.g., 3-benzothienyl-L-alanine, phenylalanine, naphthylalanine, tryptophan, or an analog or derivative thereof. Further the arginine residues can be clustered, e.g., an arginine is within 2 amino acids of another arginine residue, or two or more arginines adjacent to each other. Likewise, the amino acids having hydrophobic side chains can be clustered, e.g., one amino acid having a hydrophobic side chains is with 2 amino acids of another amino acid having a hydrophobic side chain, or two or more amino acids having ydrophobic side chain are consecutive amino acids.

The amino acids in the disclosed compounds can be coupled by a peptide bond. Additionally, some or all of the amino acids in the disclosed compounds can be coupled at the side chain of an adjacent amino acid residue.

Cell Penetrating Peptide Moiety

The cell penetrating peptide moiety comprises at least 4 amino acids, or at least 6 amino acids, more specifically from 4 to 10, from 4 to 8, from 4 to 6, from 6 to 16, from 6 to 15, from 6 to 14, from 6 to 13, from 6 to 13, from 6 to 12, from 6 to 11, from 6 to 10, from 6 to 9, from 6 to 8, from 6 to 7, from 7 to 16, from 7 to 15, from 7 to 14, from 7 to 13, from 7 to 13, from 7 to 12, from 7 to 11, from 7 to 10, from 7 to 9, from 7 to 8, from 8 to 16, from 8 to 15, from 8 to 14, from 8 to 13, from 8 to 13, from 8 to 12, from 8 to 11, from 8 to 10, from 8 to 9, from 9 to 16, from 9 to 15, from 9 to 14, from 9 to 13, from 9 to 13, from 9 to 12, from 9 to 11, from 9 to 10, from 10 to 16, from 10 to 15, from 10 to 14, from 10 to 13, from 10 to 13, from 10 to 12, from 10 to 11, from 11 to 16, from 11 to 15, from 11 to 14, from 11 to 13, from 11 to 13, from 11 to 12, from 12 to 16, from 12 to 15, from 12 to 14, from 12 to 13, from 12 to 13, from 13 to 16, from 13 to 15, from 13 to 14, from 14 to 16, from 14 to 15, or from 15 to 16 amino acids. It is also contemplated that some amino acids in the cell penetrating peptide moiety can also be part of the cargo moiety. For example, a peptide penetrating moiety FNalRR can be formed when from FNal and an cargo moiety with two Args. In this case, the two Arg residues perform dual functions. Thus, in some cases the sequence of the cargo moiety is taken into account when referring to the peptide penetrating moiety.

In some examples, at least one, at least, two, at least three amino acids, or more, have hydrophobic side chains. In some embodiments, the amino acids having hydrophiblic side chains are independently selected from glycine, alanine, valine, leucine, isoleucine, methionine, phenylalanine, tryptophan, proline, naphthylalanine, phenylglycine, homophenylalanine, tyrosine, cyclohexylalanine, 3-benzothienyl-L-alanine, piperidine-2-carboxylate, or norleucine, each of which is optionally substituted with one or more substituents. In particular embodiments, each amino acid having a hydrophobic side chain is independently an amino acid having an aromatic side chain. In some embodiments, the amino acid having an aromatic side chain is 3-benzothienyl-L-alanine, naphthylalanine, phenylglycine, homophenylalanine, phenylalanine, tryptophan, or tyrosine, each of which is optionally substituted with one or more substituents. Thus, in some embodiments, tor example, the amino acids having hydrophobic side chains are phenylalanine, naphthylalanine, tryptophan, or an analog or derivative thereof napthylalanine or tryptophan, or analogues or derivatives thereof. In other examples, at least one amino acid comprises phenylalanine, phenylglycine, or histidine, or analogues or derivatives thereof. In some examples, at least one amino acid comprises glutamine or an analogue or derivative thereof.

In some examples, the cell penetrating peptide (CPP) moiety can be or comprise any of the sequences listed in Table 2. In some examples, the cell penetrating peptide can be or comprise the reverse of any of the sequences listed in Table 2.

TABLE 2

| CPP moiety sequences | | |
|---|---|---|
| SEQ ID NO | CPP sequence | #R residues |
| 1 | FΦRRR | 3 |
| 2 | FΦRRRC | 3 |
| 3 | FΦRRRU | 3 |
| 4 | RRRΦF | 3 |
| 5 | RRRRΦF | 4 |
| 6 | FΦRRRR | 4 |
| 7 | FϕrRrR | 3 |
| 8 | FϕRrR | 3 |
| 9 | FΦRRRR | 4 |
| 10 | fΦRrRr | 4 |
| 11 | RRFRΦR | 4 |
| 12 | FRRRRΦ | 4 |
| 13 | rRFRΦR | 4 |
| 14 | RRΦFRR | 4 |
| 15 | CRRRRFW | 4 |
| 16 | FfΦRrRr | 4 |
| 17 | FFΦRRRR | 4 |
| 18 | RFRFRΦR | 4 |
| 19 | URRRRFW | 4 |
| 20 | CRRRRFW | 4 |
| 21 | FΦRRRRQK | 4 |
| 22 | FΦRRRRQC | 4 |
| 23 | fΦRrRrR | 5 |
| 24 | FΦRRRRR | 5 |
| 25 | RRRRΦFDΩC | 4 |
| 26 | FΦRRR | 3 |
| 27 | FWRRR | 3 |
| 28 | RRRΦF | 3 |
| 29 | RRRWF | 3 |
| 30 | FΦRRRR | 4 |
| 31 | FFRRR | 3 |
| 32 | FFrRr | 3 |
| 33 | FFRrR | 3 |
| 34 | FRFRR | 3 |
| 35 | FRRFR | 3 |
| 36 | FRRRF | 3 |
| 37 | GΦRRR | 3 |
| 38 | FFFRA | 1 |
| 39 | FFFRR | 2 |
| 40 | FFRRRR | 4 |
| 41 | FRRFRR | 4 |
| 42 | FRRRFR | 5 |
| 43 | RFFRRR | 4 |
| 44 | RFRRFR | 4 |
| 45 | FRFRRR | 4 |
| 46 | FFFRRR | 3 |
| 47 | FFRRRF | 3 |
| 48 | FRFFRR | 3 |
| 49 | RRFFFR | 3 |
| 50 | FFRFRR | 3 |
| 51 | FFRRFR | 3 |
| 52 | FRRFFR | 3 |
| 53 | FRRFRF | 3 |
| 54 | FRFRFR | 3 |
| 55 | RFFRFR | 3 |
| 56 | GΦRRRR | 4 |
| 57 | FFFRRRR | 4 |
| 58 | RFFRRRR | 5 |
| 59 | RRFFRRR | 5 |
| 60 | RFFFRRR | 4 |
| 61 | RRFFFRR | 4 |
| 62 | FFRRFRR | 4 |
| 63 | FFRRRRF | 4 |
| 64 | FRRFFRR | 4 |
| 65 | FFFRRRRR | 5 |
| 66 | FFFRRRRRR | 6 |
| 67 | FΦRrRr | 4 |
| 68 | XXRRRR | 4 |
| 69 | FfFRrR | 3 |

TABLE 2-continued

| CPP moiety sequences | | |
|---|---|---|
| SEQ ID NO | CPP sequence | #R residues |
| 70 | fFfrRr | 2 |
| 71 | fFfRrR | 3 |
| 72 | FfFrRr | 3 |
| 73 | fFφrRr | 3 |
| 74 | fΦfrRr | 3 |
| 75 | φFfrRr | 3 |
| 76 | FΦrRr | 3 |
| 77 | fΦrRr | 3 |
| 78 | Ac-Lys-fFRrRrD | 4 |
| 79 | Ac-Dap-fFRrRrD | 4 |
| 172 | Pip-Nal-Arg-Glu-arg-arg-glu | 3 |
| 173 | Pip-Nal-Arg-arg-arg-glu | 3 |
| 174 | Pip-Nal-Nal-Arg-arg-arg-glu | 3 |
| 175 | Pip-Nal-Nal-Arg-arg-arg-Glu | 3 |
| 178 | Pip-Nal-Phe-Arg-arg-arg-glu | 3 |
| 179 | Pip-Nal-Phe-Arg-arg-arg-Glu | 3 |
| 180 | Pip-Nal-phe-Arg-arg-arg-glu | 3 |
| 181 | Pip-Nal-phe-Arg-arg-arg-Glu | 3 |
| 182 | Pip-Nal-nal-Arg-arg-arg-Glu | 3 |
| 183 | Pip-Nal-nal-Arg-arg-arg-glu | 3 |
| 184 | [P-Cha-r-Cha-r-Cha-r-Cha-r-G][d] | 4 |
| 185 | Tm(SvP-$F_2$Pmp-H)-Dap-(FΦRRRR-Dap))[f] | 4 |
| 186 | [Tm(a-Sar-D-pThr-Pip-ΦRAa)-Dap-(FΦRRRR-Dap))[f] | 5 |
| 187 | [CRRSRRGCGRRSRRCG][g] | 8 |
| 188 | [K(Dod)RRRR] | 4 |
| 189 | LKKLCKLLKKLCKLAG<br>LKKLCKLLKKLCKLAG | 0 |
| 190 | RRRR-[KRRRE][c] | 7 |
| 191 | RRR-[KRRRRE][c] | 7 |
| 192 | RR-[KRRRRRE][c] | 7 |
| 193 | R[KRRRRRRE][c] | 7 |
| 194 | [CRCRCRCR] | 4 |
| 195 | [Pra-LRKRLRKFRN-AzK][h] | |
| 196 | T-Dap-[Dap-Dap-f-L-Dap-Dap-T] | |
| 197 | T-Arg-[Dap-Agp-f-L-Agp-Agp-T] | |

Φ = L-naphthylalanine;
ϕ = D-naphthylalanine;
Ω = L-norleucine;
r = D-arginine;
F = L-phenylalanine;
f = D-phenylalanine;
q = D-glutamine;
X = L-4-fluorophenylalanine;
Dap = L-2,3-diaminopropionic acid; Sar, sarcosine; $F_2$Pmp, L-difluorophosphonomethyl phenylalanine; Dod, dodecanoyl; Pra, L-propargylglycine; Azk, L-6-Azido-2-amino-hexanoic; Agp, L-2-amino-3-guanidinylpropionic acid;
[b]Cyclization between Pim and Nlys;
[c]Cyclization between Lys and Glu;
[d]Macrocyclization by multicomponent reaction with aziridine aldehyde and isocyanide;
[e]Cyclization between the main-chain of Gln residue;
[f]N-terminal amine and side chains of two Dap residues bicyclized with Tm;
[g]Three Cys side chains bicyclized with tris(bromomethyl)benzene;
[h]Cyclization by the click reaction between Pra and Azk.

In some examples, the cell penetrating peptide moiety can by any of SEQ ID NO:1 to SEQ ID NO:79 or SEQ ID NO: 172 to SEQ ID NO: 197. In some examples, the cell penetrating peptide moiety can be a variant of any of SEQ ID NO:1 to SEQ ID NO:79 or SEQ ID NO: 172 to SEQ ID NO: 197. Peptide variants are well understood to those of skill in the art and can involve amino acid sequence modifications. For example, amino acid sequence modifications typically fall into one or more of three classes: substitutional, insertional, or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of 1 to 3 residues. Deletions are characterized by the removal of one or more amino acid residues from the peptide sequence. Typically, no more than from 1 to 3 residues are deleted at any one site within the peptide. Amino acid substitutions are typically of single residues, but can occur at a number of different locations at once; insertions usually will be on the order of about from 1 to 3 amino acid residues; and deletions will range about from 1 to 3 residues. Deletions or insertions preferably are made in adjacent pairs, i.e. a deletion of 2 residues or insertion of 2 residues. Substitutions, deletions, insertions or any combination thereof can be combined to arrive at a final construct. Substitutional variants are those in which at least one residue has been removed and a different residue inserted in its place. Such substitutions generally are made in accordance with the following Table 3 and are referred to as conservative substitutions.

TABLE 3

Amino Acid Substitutions
Exemplary Conservative Substitutions

| | |
|---|---|
| Ala replaced by ser | Leu replaced by ile or val |
| Arg replaced by lys or gln | Lys replaced by arg or gln |
| Asn replaced by gln or his | Met replaced by leu or ile |
| Asp replaced by glu | Phe replaced by met, leu, tyr, or fpa |
| Cys replaced by ser | Ser replaced by thr |
| Gln replaced by asn or lys | Thr replaced by ser |
| Glu replaced by asp | Trp replaced by tyr |
| Gly replaced by pro | Tyr replaced by trp or phe |
| His replaced by asn or gln | Val replaced by ile or leu |
| Ile replaced by leu or val | Nal replaced by Trp or Phe |

Substantial changes in function are made by selecting substitutions that are less conservative than those in Table 3, i.e., selecting residues that differ more significantly in their effect on maintaining (a) the structure of the peptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, argininyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the peptides provided herein.

It is understood that one way to define the variants of the disclosed cell penetrating peptide moieties is through defining the variants in terms of homology/identity to specific known sequences. For example, SEQ ID NO: 1 to SEQ ID NO: 79 or SEQ ID NO: 172 to SEQ ID NO: 197 each sets forth a particular sequence. Specifically disclosed are variants of these peptide that have at least, 85%, 90%, 95%, or 97% homology to SEQ ID NO:1 to SEQ ID NO:79 or SEQ ID NO: 172 to SEQ ID NO: 197. Those of skill in the art readily understand how to determine the homology of two proteins. For example, the homology can be calculated after aligning the two sequences so that the homology is at its highest level.

In addition to variants of SEQ ID NO: 1 to SEQ ID NO: 79 or SEQ ID NO: 172 to SEQ ID NO: 197 are derivatives of these peptides which also function in the disclosed methods and compositions. Derivatives are formed by replacing one or more residues with a modified residue, where the side chain of the residue has been modified. In other embodiments, the cell penetrating peptide moiety can be any sequence disclosed in U.S. Patent App. Pub. 2017/0190743, filed May 21, 2015, U.S. App. No. 62/507,483, filed on May 17, 2017, or the PCT application claiming priority thereto, filed Nov. 22, 2017, entitled "Cell Penetrating Cyclopeptides," the entire contents of each of which are herein incorporated by reference in its entirety for all purposes.

In any of these moieties, there are at least one, at least two, or more specifically, at least three adjacent arginine (R) residues. Further, in these structures there are at least one, at least two, or at least three hydrophobic residues, for example, 3-benzothienyl-L-alanine, phenylalanine, naphthylalanine, tryptophan, or an analog or derivative thereof. For example, there can be 1 arginine and 5 hydrophobic residues like 3-benzothienyl-L-alanine, phenylalanine, naphthylalanine, tryptophan, or an analog or derivative thereof, 2 arginine and 4 hydrophobic residues like phenylalanine, naphthylalanine, tryptophan, or an analog or derivative thereof, 3 arginine and 3 hydrophobic residues like 3-benzothienyl-L-alanine, phenylalanine, naphthylalanine, tryptophan, or an analog or derivative thereof, 4 arginine and 2 hydrophobic residues like 3-benzothienyl-L-alanine, phenylalanine, naphthylalanine, tryptophan, or an analog or derivative thereof, or 4 arginine and 1 hydrophobic residue like 3-benzothienyl-L-alanine, phenylalanine, naphthylalanine, tryptophan, or an analog or derivative thereof. In a specific example, the cyclic compunds disclosed herein have 3 arginines and 3 hydrophobic residues like 3-benzothienyl-L-alanine, phenylalanine, naphthylalanine, tryptophan, or an analog or derivative thereof. Further the arginine residues can be clustered, e.g., an arginine is within 2 amino acids of another arginine residue. Likewise, the hydrophobic residues can be clustered, e.g., one hydrophobic residue is with 2 amino acids of another hydrophobic residue.

In certain examples, when there are three adjacent arginine (-Arg-Arg-Arg-) residues, they can be $-AA_1-AA_2-AA_3-$, $-AA_4-AA_5-AA_6-$, $-AA_7-AA_8-AA_9-$, $-AA_{10}-AA_{11}-AA_{12}-$, $-AA_{13}-AA_{14}-AA_{15}-$, $-AA_{16}-AA_{17}-AA_{18}-$, $-AA_2-AA_3-AA_4-$, $-AA_5-AA_6-AA_7-$, $-AA_8-AA_9-AA_{10}-$, $-AA_{11}-AA_{12}-AA_{13}-$, $-AA_{14}-AA_{15}-AA_{16}-$, $-AA_{17}-AA_{18}-AA_1-$, $-AA_3-AA_4-AA_5-$, $-AA_6-AA_7-AA_8-$, $-AA_9-AA_{10}-AA_{11}-$, $-AA_{12}-AA_{13}-AA_{14}-$, $-AA_{15}-AA_{16}-AA_{17}-$, $-AA_{18}-AA_1-AA_2-$, $-AA_7-AA_8-AA_1-$, $-AA_8-AA_9-AA_1-$, $-AA_9-AA_{10}-AA_1-$, $-AA_{10}-AA_{11}-AA_1-$, $-AA_{11}-AA_{12}-AA_1-$, $-AA_{12}-AA_{13}-AA_1-$, $-AA_{13}-AA_{14}-AA_1-$, $-AA_{14}-AA_{15}-AA_1-$, $-AA_{15}-AA_{16}-AA_1-$, $-AA_{16}-AA_{17}-AA_1-$, $-AA_{17}-AA_{18}-AA_1-$, $-AA_8-AA_1-AA_2-$, $-AA_9-AA_1-AA_2-$, $-AA_{10}-AA_1-AA_2-$, $-AA_{11}-AA_1-AA_2-$, $-AA_{12}-AA_1-AA_2-$, $-AA_{13}-AA_1-AA_2-$, $-AA_{14}-AA_1-AA_2-$, $-AA_{15}-AA_1-AA_2-$, $-AA_{16}-AA_1-AA_2-$, or $-AA_{17}-AA_1-AA_2-$.

Beta-Hairpin Turn Creating Moiety

The beta-hairpin turn creating moiety can be any suitable combination of amino acids which form a beta-hairpin turn. The beta-hairpin turn can result from intramolecular hydrogen bonding interactions, intramolecular disulfide bonds, intramolecular hydrophobic interactions, intramolecular pi-stacking (π-π) interactions, or the peptide can be modified by incorporating a covalent bond to conjugate opposing amino acids thereby forming a beta-hairpin turn motif.

For example, a beta-hairpin turn can be created by incorporating amino acids having side chains, which can participate in hydrogen bonding interactions at appropriate positions in the peptide (e.g., a side chain with hydrogen bond donors that are adjacent to side chains with hydrogen bond acceptors when the peptide is in the beta-hairpin turn motif). Similarly, cysteine residues (or analogs or derivatives thereof, or other non-natural amino acids having a thiol group) can be incorporated into the present peptides at appropriate positions which allow the thiol groups to form a disulfide bond, thereby forming a beta-hairpin turn. One example of a sequence containing two cysteine residues that forms a beta-hairpin turn via a disulfide bond is Ac-CTWEGNKLTC (SEQ ID NO:155), described in Skelton, et al., *β-hairpin polypeptides by design and selection*. Spectroscopy 17 (2003) 213-230, which is herein incorporated by reference in its entirety.

In other embodiments, the beta-hairpin turn can be created by incorporating an achiral α-aminoisobutyric acid (Aib) in combination with either a D-α-amino acid (D-pro, D-ala, D-val) or an achiral α-amino acid (e.g., Gly) into the peptides of the disclosure.

In other embodiments, amino acid residues have aromatic side chains can be incorporated into the present peptides at appropriate positions which allow the aromatic side chains to participate in pi-stacking interactions, thereby forming a beta-hairpin turn. In one such example, the peptide can contain multiple tryptophan residues (tryptophan zipper), as described in Cochran, et al., *Tryptophan zippers: Stable, monomeric β-hairpins*. Proceedings of the National Academy of Sciences. 98 (10): 5578-5583 (2001-05-08), which is herein incorporated by reference in its entirety.

In other embodiments, the present peptides may include any of the sequences which create beta-hairpin turns as described in Khakshoor O, Nowick J S. Artificial beta-sheets: chemical models of beta-sheets. Curr Opin Chem Biol. 2008 December; 12(6):722-9. doi: 10.1016, which is herein incorporated by reference in its entirety.

In still other embodiments, the beta-hairpin turn creating motif may be created by incorporating an azobenzene moiety into the present peptides. The azobenzene moiety may be incorporated into the peptide by conjugating 3-(3-aminomethyl)phenylazo]phenylacetic acid between to two amino acid residues to form, e.g.,

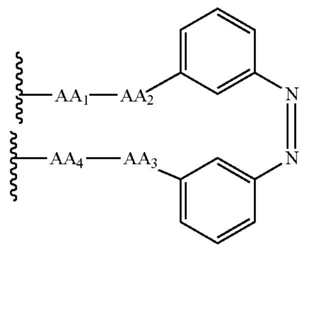

Non-limiting examples of azobenzene, beta-hairpin turn peptides are disclosed in Dong et al., pi A Photocontrolled *β-Hairpin Peptide*. Chemistry—A European Journal. 12 (4): 1114-1120 (2006-01-23), which is herein incorporated by reference in its entirety.

In particular embodiments, the beta-hairpin turn creating moiety can be -D-Pro-L-Pro- or -L-Pro-D-Pro-.

In some embodiments, the cyclic peptides disclosed herein comprise at least one beta-hairpin turn creating moiety, or at least two beta-hairpin turn creating moieties.

The beta-hairturn creating moiety can be located at any suitable location on the cyclic peptides disclosed herein. In some embodiments, the disclosed cell penetrating peptide moiety can be adjacent to the beta-hairpin turn creating moiety (e.g., -D-Pro-L-Pro- or -L-Pro-D-Pro-) or separated from the beta-hairpin turn creating moiety by up to 4 amino acid residues. In other embodiments, the beta-hairpin turn creating moiety can be located between two amino acids in the cell penetrating peptide moiety, e.g., the cell penetrating peptide moieties disclosed in the Table 2. For example, in some embodiments, the beta-hairpin turn creating moiety may be located between an arginine residue and an amino acid residue having a hydrophobic side chain. Non-limiting examples of this motif include: FΦ-D-Pro-L-Pro-RRR (SEQ ID NO: 198); fFφ-D-Pro-L-Pro-rRr (SEQ ID NO: 199); fΦf-D-Pro-L-Pro-rRr (SEQ ID NO: 200); Fϕ-D-Pro-L-Pro-rRrR (SEQ ID NO: 201); Fϕ-D-Pro-L-Pro-rRrR (SEQ ID NO: 202); fΦ-D-Pro-L-Pro-RrRr (SEQ ID NO: 203); FΦ-L-Pro-D-Pro-RRR (SEQ ID NO: 204); fFφ-L-Pro-D-Pro-rRr (SEQ ID NO: 205); fΦf-L-Pro-D-Pro-rRr (SEQ ID NO: 206); Fϕ-L-Pro-D-Pro-rRrR (SEQ ID NO: 207); Fϕ-L-Pro-D-Pro-rRrR (SEQ ID NO: 208); and fΦ-L-Pro-D-Pro-RrRr (SEQ ID NO: 209). As another example, in various embodiments, the beta-hairpin turn creating moiety may be located between arginine arginine residues. Non-limiting examples of this motif include: FΦR-D-Pro-L-Pro-RR (SEQ ID NO: 210); fFrφ-D-Pro-L-Pro-Rr (SEQ ID NO: 211); fΦfr-D-Pro-L-Pro-Rr (SEQ ID NO: 212); Fϕr-D-Pro-L-Pro-RrR (SEQ ID NO: 213); FϕrR-D-Pro-L-Pro-rR (SEQ ID NO: 214); fφR-D-Pro-L-Pro-rRr (SEQ ID NO: 215); FΦR-L-Pro-D-Pro-RR (SEQ ID NO: 216); fFφr-L-Pro-D-Pro-Rr (SEQ ID NO: 217); fΦf-L-Pro-D-Pro-rRr (SEQ ID NO: 218); Fϕr-L-Pro-D-Pro-RrR (SEQ ID NO: 219); Fϕr-L-Pro-D-Pro-RrR (SEQ ID NO: 220); and fΦR-L-Pro-D-Pro-rRr (SEQ ID NO: 221).

In other embodiments, the beta-hairpin turn creating moiety may be located between two arginine residues. In still other embodiments, beta-hairpin turn creating moiety may be located between two amino acid residues which have a hydrophobic side chain.

Cargo Moiety

In some examples, the cell penetrating peptide moiety, beta-hairpin turn creating moiety, and cargo moiety together are all part of the cyclic ring; this is referred to herein as an "endocyclic" configuration. Thus, besides the beta-hairpin turn creating moiety, and the arginine and hydrophobic residues which make up the cell penetrating peptide moiety, any 3-46 amino acids (e.g., 3-26, or 3-13 amino acids) in the disclosed cyclic compounds can be cargo amino acid sequences.

Alternatively, in some examples, the cell penetrating peptide moiety and beta-hairpin turn creating moiety are part of the cyclic compound and the cargo moiety is appended (conjugated) to the cyclic ring; this is referred to herein as an "exocyclic" configuration. That is, the cargo amino acid sequences or moiety can be attached to any of the side chain residues (e.g., Formula I or $AA_1$-$AA_{18}$) or peptide nitrogens in the disclosed cyclic compounds. The cargo moiety can also be a cyclic moiety itself that is fused to the cyclic beta-hairpin shaped CPP compounds disclosed herein. These are referred to as a "bicyclic" configuration.

When the moiety is part of the cyclic ring (with the cell penetrating moiety and the beta-hairpin turn creating moiety), the amino acid residues may be selected to interact with a biological target of interest. These amino acid residues may be a sequence that is known to bind to the target, or the residues can be designed to the target of interest.

When the cargo moiety is attached to the side chain of an amino acid in the cyclic peptides disclosed herein, the cyclic peptides described herein include an amino acid having a side chain with a suitable functional group to form a covalent bond (conjugation) with the cargo, or a side chain which may be modified to provide a suitable functional group (e.g., via conjugation of a linker) that forms a covalent bond with the cargo. In some embodiments, the amino acid on the cyclic peptide which has a side chain suitable conjugation of the cargo is a glutamic acid residue, an aspartic acid residue, a lysine residue, or an 2,3-diaminopropionic acid residue. In such embodiments, the cargo may be directly conjugated to the side chain of the amino acid (e.g., by forming amide bond with a glutamic acid residue or a 2,3-diaminopropionic acid residue) or the cargo may be conjugated to the amino acid side chain through a linker (e.g., PEG).

The cargo moiety can comprise any cargo of interest, for example a linker moiety, a detectable moiety, a therapeutic moiety, a targeting moiety, and the like, or any combination thereof. In some examples, the cargo moiety can comprise one or more additional amino acids (e.g., K, UK, TRV); a linker (e.g., bifunctional linker LC-SMCC); coenzyme A; phosphocoumaryl amino propionic acid (pCAP); 8-amino-3,6-dioxaoctanoic acid (miniPEG); L-2,3-diaminopropionic acid (Dap or J); L-β-naphthylalanine; L-pipecolic acid (Pip); sarcosine; trimesic acid; 7-amino-4-methylcourmarin (Amc); fluorescein isothiocyanate (FITC); L-2-naphthylalanine; norleucine; 2-aminobutyric acid; Rhodamine B (Rho); Dexamethasone (DEX); or combinations thereof.

In some examples the cargo moiety can comprise any of those listed in Table 4, or derivatives or combinations thereof. That is, the cargo moiety can by any of SEQ ID NO:80 to SEQ ID NO:88. In some examples, the cargo moiety can be a variant of any of SEQ ID NO: 80 to SEQ ID NO:88. The cargo moiety and cell penetrating peptide moiety can overlap, that is residues that form the cell penetrating peptide moiety can also be part of the sequence that forms the cargo moiety, and vice a versa.

TABLE 4

Example cargo moieties

| SEQ ID NO | Abbreviation | Sequence* |
|---|---|---|
| 80 | $R_5$ | RRRRR |
| 81 | $A_5$ | AAAAA |
| 82 | $F_4$ | FFFF |
| 83 | PCP | DE(pCAP)LI |
| 84 | $A_7$ | AAAAAAA |
| 85 | | RARAR |
| 86 | | DADAD |

TABLE 4-continued

Example cargo moieties

| SEQ ID NO | Abbreviation | Sequence* |
|---|---|---|
| 87 | | DΩUD |
| 88 | | UTRV |

*pCAP, phosphocoumaryl amino propionic acid; Ω = norleucine; U = 2-aminobutyric acid.

Detectable Moiety

The disclosed compounds can also comprise a detectable moiety. In some examples, the cargo moiety comprises the dectectable moiety. The detectable moiety can comprise any detectable label. Examples of suitable detectable labels include, but are not limited to, a UV-Vis label, a near-infrared label, a luminescent group, a phosphorescent group, a magnetic spin resonance label, a photosensitizer, a photocleavable moiety, a chelating center, a heavy atom, a radioactive isotope, a isotope detectable spin resonance label, a paramagnetic moiety, a chromophore, or any combination thereof. In some embodiments, the label is detectable without the addition of further reagents.

In some embodiments, the detectable moiety is a biocompatible detectable moiety, such that the compounds can be suitable for use in a variety of biological applications. "Biocompatible" and "biologically compatible", as used herein, generally refer to compounds that are, along with any metabolites or degradation products thereof, generally nontoxic to cells and tissues, and which do not cause any significant adverse effects to cells and tissues when cells and tissues are incubated (e.g., cultured) in their presence.

The detectable moiety can contain a luminophore such as a fluorescent label or near-infrared label. Examples of suitable luminophores include, but are not limited to, metal porphyrins; benzoporphyrins; azabenzoporphyrine; napthoporphyrin; phthalocyanine; polycyclic aromatic hydrocarbons such as perylene, perylene diimine, pyrenes; azo dyes; xanthene dyes; boron dipyoromethene, aza-boron dipyoromethene, cyanine dyes, metal-ligand complex such as bipyridine, bipyridyls, phenanthroline, coumarin, and acetylacetonates of ruthenium and iridium; acridine, oxazine derivatives such as benzophenoxazine; aza-annulene, squaraine; 8-hydroxyquinoline, polymethines, luminescent producing nanoparticle, such as quantum dots, nanocrystals; carbostyril; terbium complex; inorganic phosphor; ionophore such as crown ethers affiliated or derivatized dyes; or combinations thereof. Specific examples of suitable luminophores include, but are not limited to, Pd (II) octaethylporphyrin; Pt (II)-octaethylporphyrin; Pd (II) tetraphenylporphyrin; Pt (II) tetraphenylporphyrin; Pd (II) meso-tetraphenylporphyrin tetrabenzoporphine; Pt (II) meso-tetrapheny metrylbenzoporphyrin; Pd (II) octaethylporphyrin ketone; Pt (II) octaethylporphyrin ketone; Pd (II) meso-tetra(pentafluorophenyl)porphyrin; Pt (II) meso-tetra(pentafluorophenyl)porphyrin; Ru (II) tris(4, 7-diphenyl-1,10-phenanthroline) (Ru (dpp)$_3$); Ru (II) tris(1, 10-phenanthroline) (Ru(phen)$_3$), tris(2,2'-bipyridine) rutheniurn (II) chloride hexahydrate (Ru(bpy)$_3$); erythrosine B; fluorescein; fluorescein isothiocyanate (FITC); eosin; iridium (III) ((N-methyl-benzimidazol-2-yl)-7-(diethylamino)-coumarin)); indium (III) ((benzothiazol-2-yl)-7-(diethylamino)-coumarin))-2-(acetylacetonate); Lumogen dyes; Macroflex fluorescent red; Macrolex fluorescent yellow; Texas Red; rhodamine B; rhodamine 6G; sulfur rhodamine; m-cresol; thymol blue; xylenol blue; cresol red;

chlorophenol blue; bromocresol green; bromcresol red; bromothymol blue; Cy2; a Cy3; a Cy5; a Cy5.5; Cy7; 4-nitirophenol; alizarin; phenolphthalein; o-cresolphthalein; chlorophenol red; calmagite; bromo-xylenol; phenol red; neutral red; nitrazine; 3,4,5,6-tetrabromphenolphtalein; congo red; fluorescein; eosin; 2',7'-dichlorofluorescein; 5(6)-carboxyfluorecsein; carboxynaphthofluorescein; 8-hydroxypyrene-1,3,6-trisulfonic acid; semi-naphthorhodafluor; semi-naphthofluorescein; tris (4,7-diphenyl-1,10-phenanthroline) ruthenium (II) dichloride; (4,7-diphenyl-1,10-phenanthroline) ruthenium (II) tetraphenylboron; platinum (II) octaethylporphyin; dialkylcarbocyanine; dioctadecylcycloxacarbocyanine; fluorenylmethyloxycarbonyl chloride; 7-amino-4-methylcourmarin (Amc); green fluorescent protein (GFP); and derivatives or combinations thereof.

In some examples, the detectable moiety can comprise Rhodamine B (Rho), fluorescein isothiocyanate (FITC), 7-amino-4-methylcourmarin (Amc), green fluorescent protein (GFP), or derivatives or combinations thereof.

The detectible moiety can be attached to the cell penetrating peptide moiety at the amino group, the carboxylate group, or the side chain of any of the amino acids of the cell penetrating peptide moiety (e.g., at the amino group, the carboxylate group, or the side chain or any of $AA_1$-$AA_{18}$).

Therapeutic Moiety

The disclosed compounds can also comprise a therapeutic moiety. In some examples, the cargo moiety comprises a therapeutic moiety. The detectable moiety can be linked to a therapeutic moiety or the detectable moiety can also serve as the therapeutic moiety. Therapeutic moiety refers to a group that when administered to a subject will reduce one or more symptoms of a disease or disorder.

The therapeutic moiety can comprise a wide variety of drugs, including antagonists, for example enzyme inhibitors, and agonists, for example a transcription factor which results in an increase in the expression of a desirable gene product (although as will be appreciated by those in the art, antagonistic transcription factors can also be used), are all included. In addition, therapeutic moiety includes those agents capable of direct toxicity and/or capable of inducing toxicity towards healthy and/or unhealthy cells in the body. Also, the therapeutic moiety can be capable of inducing and/or priming the immune system against potential pathogens.

The therapeutic moiety can, for example, comprise an anticancer agent, antiviral agent, antimicrobial agent, anti-inflammatory agent, immunosuppressive agent, anesthetics, or any combination thereof.

The therapeutic moiety can comprise an anticancer agent. Example anticancer agents include 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, -Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR. The therapeutic moiety can also comprise a biopharmaceutical such as, for example, an antibody.

In some examples, the therapeutic moiety can comprise an antiviral agent, such as ganciclovir, azidothymidine (AZT), lamivudine (3TC), etc.

In some examples, the therapeutic moiety can comprise an antibacterial agent, such as acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; Lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin; oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillin G benzathine; penicillin G potassium; penicillin G procaine; penicillin G sodium; penicillin V; penicillin V benzathine; penicillin V hydrabamine; penicillin V potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin B sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; or zorbamycin.

In some examples, the therapeutic moiety can comprise an anti-inflammatory agent.

In some examples, the therapeutic moiety can comprise dexamethasone (Dex).

In other examples, the therapeutic moiety comprises a therapeutic protein. For example, some people have defects in certain enzymes (e.g., lysosomal storage disease). It is disclosed herein to deliver such enzymes/proteins to human cells by linking to the enzyme/protein to one of the disclosed cell penetrating peptides. The disclosed cell penetrating peptides have been tested with proteins (e.g., GFP, PTP1B, actin, calmodulin, troponin C) and shown to work.

Targeting Moieties

The disclosed compounds can also comprise a targeting moiety. In some examples, the cargo moiety comprises a targeting moiety. The targeting moiety can comprise, for example, a sequence of amino acids that can target one or more enzyme domains. In some examples, the targeting moiety can comprise an inhibitor against an enzyme that can play a role in a disease, such as cancer, cystic fibrosis, diabetes, obesity, or combinations thereof. For example, the targeting moiety can comprise any of the sequences listed in Table 5.

TABLE 5

| Example targeting moieties | | |
|---|---|---|
| SEQ ID NO | Abbreviation * | Sequence |
| 89 | PΘGΛYR | Pro-Pip-Gly-$F_2$Pmp-Tyr-Arg |
| 90 | SΘIΛΛR | Ser-Pip-Ile-$F_2$Pmp-$F_2$Pmp-Arg |
| 91 | IHIΛIR | Ile-His-Ile-$F_2$Pmp-Ile-Arg |
| 92 | AaIΛΘR | Ala-(D-Ala)-Ile-$F_2$Pmp-Pip-Arg |
| 93 | ΣSΘΛvR | Fpa-Ser-Pip-$F_2$Pmp-(D-Val)-Arg |
| 94 | ΘnPΛAR | Pip-(D-Asn)-Pro-$F_2$Pmp-Ala-Arg |
| 95 | TΨAΛGR | Tyr-Phg-Ala-$F_2$Pmp-Gly-Arg |
| 96 | AHIΛaR | Ala-His-Ile-$F_2$Pmp-(D-Ala)-Arg |
| 97 | GnGΛpR | Gly-(D-Asn)-Gly-$F_2$Pmp-(D-Pro)-Arg |
| 98 | fQΘΛIR | (D-Phe)-Gln-Pip-$F_2$Pmp-Ile-Arg |
| 99 | SPGΛHR | Ser-Pro-Gly-$F_2$Pmp-His-Arg |
| 100 | ΘYIΛHR | Pip-Tyr-Ile-$F_2$Pmp-His-Arg |
| 101 | SvPΛHR | Ser-(D-Val)-Pro-$F_2$Pmp-His-Arg |
| 102 | AIPΛnR | Ala-Ile-Pro-$F_2$Pmp-(D-Asn)-Arg |
| 103 | ΣSIΛQF | Fpa-Ser-Ile-$F_2$Pmp-Gln-Phe |
| 104 | AaΨΛfR | Ala-(D-Ala)-Phg-$F_2$Pmp-(D-Phe)-Arg |
| 105 | ntΨΛΨR | (D-Asn)-(D-Thr)-Phg-$F_2$Pmp-Phg-Arg |
| 106 | IPΨΛΩR | Ile-Pro-Phg-$F_2$Pmp-Nle-Arg |
| 107 | QΘΣΛΘR | Gln-Pip-Fpa-$F_2$Pmp-Pip-Arg |
| 108 | nAΣΛGR | (D-Asn)-Ala-Fpa-$F_2$Pmp-Gly-Arg |
| 109 | ntYΛAR | (D-Asn)-(D-Thr)-Tyr-$F_2$Pmp-Ala-Arg |
| 110 | eAΨΛvR | (D-Glu)-Ala-Phg-$F_2$Pmp-(D-Val)-Arg |
| 111 | IvΨΛAR | Ile-(D-Val)-Phg-$F_2$Pmp-Ala-Arg |
| 112 | YtΨΛAR | Tyr-(D-Thr)-Phg-$F_2$Pmp-Ala-Arg |
| 113 | nΘΨΛIR | (D-Asn)-Pip-Phg-$F_2$Pmp-Ile-Arg |
| 114 | ΘnWΛHR | Pip-(D-Asn)-Trp-$F_2$Pmp-His-Arg |
| 115 | YΘvΛIR | Tyr-Pip-(D-Val)-$F_2$Pmp-Ile-Arg |
| 116 | nSAΛGR | (D-Asn)-Ser-(D-Ala)-$F_2$Pmp-Gly-Arg |
| 117 | tnvΛaR | (D-Thr)-(D-Asn)-(D-Val)-$F_2$Pmp-(D-Ala)-Arg |
| 118 | ntvΛtR | (D-Asn)-(D-Thr)-(D-Val)-$F_2$Pmp-(D-Thr)-Arg |
| 119 | SItΛYR | Ser-Ile-(D-Thr)-$F_2$Pmp-Tyr-Arg |
| 120 | nΣnΛlR | (D-Asn)-Fpa-(D-Asn)-$F_2$Pmp-(D-Leu)-Arg |
| 121 | YnnΛΩR | Tyr-(D-Asn)-(D-Asn)-$F_2$Pmp-Nle-Arg |
| 122 | nYnΛGR | (D-Asn)-Tyr-(D-Asn)-$F_2$Pmp-Gly-Arg |
| 123 | AWnΛAR | Ala-Trp-(D-Asn)-$F_2$Pmp-Ala-Arg |
| 124 | vtHΛYR | (D-Val)-(D-Thr)-His-$F_2$Pmp-Tyr-Arg |
| 125 | PΨHAΘR | Pro-Phg-His-$F_2$Pmp-Pip-Arg |
| 126 | nΨHΛGR | (D-Asn)-Phg-His-$F_2$Pmp-Gly-Arg |

TABLE 5-continued

Example targeting moieties

| SEQ ID NO | Abbreviation * | Sequence |
|---|---|---|
| 127 | PAHΛGR | Pro-Ala-His-$F_2$Pmp-Gly-Arg |
| 128 | AYHΛIR | Ala-Tyr-His-$F_2$Pmp-Ile-Arg |
| 129 | nΘeΛYR | (D-Asn)-Pip-(D-Glu)-$F_2$Pmp-Tyr-Arg |
| 130 | vSSΛtR | (D-Val)-Ser-Ser-$F_2$Pmp-(D-Thr)-Arg |
| 133 | aΞt'θΦ'YQK | ((D-Ala)-Sar-(D-pThr)-Pp-Nal-Tyr-Gln)-Lys |
| 134 | Tm(aΞt'θΦ'RA)Dap | Tm((D-Ala)-Sar-(D-pThr)-Pp-Nal-Arg-Ala)-Dap |
| 135 | Tm(aΞt'θΦ'RAa)Dap | Tm((D-Ala)-Sar-(D-pThr)-Pp-Nal-Arg-Ala-(D-Ala))-Dap |
| 136 | Tm(aΞtθΦ'RAa)Dap | Tm((D-Ala)-Sar-(D-Thr)-Pp-Nal-Arg-Ala-(D-Ala))-Dap |
| 137 | Tm(aΞtθΦ'RAa)Dap | Tm((D-Ala)-Sar-(D-Thr)-(D-Ala)-Nal-Arg-Ala-(D-Ala))-Dap |

*Fpa, Σ = L-4-fluorophenylalanine; Pip, Θ = L-homoproline; Nle, Ω = L-norleucine; Phg, Ψ = L-phenylglycine; $F_2$Pmp, Λ = L-4-(phosphonodifluoromethyl)phenylalanine; Dap = L-2,3-diaminopropionic acid; Nal, Φ' = L-β-naphthylalanine; Pp, ϑ = L-pipecolic acid; Sar, Ξ = sarcosine; Tm = trimesic acid.

In some examples, the targeting moiety can by any of SEQ ID NO:89 to SEQ ID NO: 130 and SEQ ID NO:133 to SEQ ID NO:137. In some examples, the targeting moiety can be a variant of any of SEQ ID NO: 89 to SEQ ID NO: 130 and SEQ ID NO: 133 to SEQ ID NO: 137.

The targeting moiety and cell penetrating peptide moiety can overlap, that is residues that form the cell penetrating peptide moiety can also be part of the sequence that forms the targeting moiety, and vice a versa.

The therapeutic moiety can be attached to the cell penetrating peptide moiety at the amino group, the carboxylate group, or the side chain of any of the amino acids of the cell penetrating peptide moiety (e.g., at the amino group, the carboxylate group, or the side chain or any of $AA^1$-$AA^{18}$). In some examples, the therapeutic moiety can be attached to the detectable moiety.

In some examples, the therapeutic moiety can comprise a targeting moiety that can act as an inhibitor against Ras (e.g., K-Ras), PTP1B, Pin1, Grb2 SH2, CAL PDZ, and the like, or combinations thereof.

Ras is a protein that in humans is encoded by the RAS gene. The normal Ras protein performs an essential function in normal tissue signaling, and the mutation of a Ras gene is implicated in the development of many cancers. Ras can act as a molecular on/off switch, once it is turned on Ras recruits and activates proteins necessary for the propagation of growth factor and other receptors' signal. Mutated forms of Ras have been implicated in various cancers, including lung cancer, colon cancer, pancreatic cancer, and various leukemias.

Protein-tyrosine phosphatase 1B (PTP1B) is a prototypical member of the PTP superfamily and plays numerous roles during eukaryotic cell signaling. PTP1B is a negative regulator of the insulin signaling pathway, and is considered a promising potential therapeutic target, in particular for the treatment of type II diabetes. PIP1B has also been implicated in the development of breast cancer.

Pin1 is an enzyme that binds to a subset of proteins and plays a role as a post phosphorylation control in regulating protein function. Pin1 activity can regulate the outcome of proline-directed kinase signaling and consequently can regulate cell proliferation and cell survival. Deregulation of Pin1 can play a role in various diseases. The up-regulation of Pin1 may be implicated in certain cancers, and the down-regulation of Pin1 may be implicated in Alzheimer's disease. Inhibitors of Pin1 can have therapeutic implications for cancer and immune disorders.

Grb2 is an adaptor protein involved in signal transduction and cell communication. The Grb2 protein contains one SH2 domain, which can bind tyrosine phosphorylated sequences. Grb2 is widely expressed and is essential for multiple cellular functions. Inhibition of Grb2 function can impair developmental processes and can block transformation and proliferation of various cell types.

It was recently reported that the activity of cystic fibrosis membrane conductance regulator (CFTR), a chloride ion channel protein mutated in cystic fibrosis (CF) patients, is negatively regulated by CFTR-associated ligand (CAL) through its PDZ domain (CAL-PDZ) (Wolde, M et al. *J. Biol. Chem.* 2007, 282, 8099). Inhibition of the CFTR/CAL-PDZ interaction was shown to improve the activity of ΑPhe508-CFTR, the most common form of CFTR mutation (Cheng, S H et al. *Cell* 1990, 63, 827; Kerem, B S et al. *Science* 1989, 245, 1073), by reducing its proteasome-mediated degradation (Cushing, P R et al. *Angew. Chem. Int. Ed.* 2010, 49, 9907). Thus, disclosed herein is a method for treating a subject having cystic fibrosis by administering an effective amount of a compound or composition disclosed herein. The compound or composition administered to the subject can comprise a therapeutic moiety that can comprise a targeting moiety that can act as an inhibitor against CAL PDZ. Also, the decompositions or compositions disclosed herein can be administered with a molecule that corrects the CFTR function.

In some examples the targeting moiety can comprise E-T-G-E-F-L (SEQ ID NO: 138) or LDPETGE (SEQ ID NO:139).

Methods of Making

The compounds described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, WI), Acros Organics (Morris Plains, NJ), Fisher Scientific (Pittsburgh, PA), Sigma (St. Louis, MO), Pfizer (New York, NY), GlaxoSmithKline (Raleigh, NC), Merck (Whitehouse Station, NJ), Johnson & Johnson (New Brunswick, NJ), Aventis (Bridgewater, NJ), AstraZeneca (Wilmington, DE), Novartis (Basel, Switzerland), Wyeth (Madison, NJ), Bristol-Myers-Squibb (New York, NY), Roche (Basel, Switzerland), Lilly (Indianapolis, IN), Abbott (Abbott Park, IL), Schering Plough (Kenilworth, NJ), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^{1}H$ or $^{13}C$) infrared spectroscopy, spectrophotometry (e.g., UV-visible), or mass spectrometry, or by chromatography such as high performance liquid chromatography (HPLC) or thin layer chromatography.

The disclosed compounds can be prepared by solid phase peptide synthesis wherein the amino acid α-N-terminal is protected by an acid or base protecting group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is particularly preferred for the synthesis of the disclosed compounds. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxy-carbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for asparticacid and glutamic acid, benzyl and t-butyl and for cysteine, triphenylmethyl (trityl). In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. Solid supports for synthesis of α-C-terminal carboxy peptides is 4-hydroxymethylphenoxymethyl-copoly (styrene-1% divinylbenzene) or 4-(2',4'-dimethoxyphenyl-Fmoc-aminomethyl) phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazolidinyl)phosphine chloride (BOPCl), mediated coupling for from about 1 to about 24 hours at a temperature of between 10° C. and 50° C. in a solvent such as dichloromethane or DMF. When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal amino acid as described above. One method for coupling to the deprotected 4 (2',4'-dimethoxyphenyl-Fmoc-aminomethyl) phenoxy-acetamidoethyl resin is O-benzotriazol-1-yl-N,N,N',N'-tetramethyluroniumhexafluorophosphate (HBTU, 1 equiv.) and 1-hydroxybenzotriazole (HOBT, 1 equiv.) in DMF. The coupling of successive protected amino acids can be carried out in an automatic polypeptide synthesizer. In one example, the α-N-terminal in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent can be O-benzotriazol-1-yl-N,N,N',N'-tetramethyluroniumhexafluorophosphate (HBTU, 1 equiv.) and 1-hydroxybenzotriazole (HOBT, 1 equiv.). At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thianisole, water, ethanedithiol and trifluoroacetic acid. In cases wherein the α-C-terminal of the polypeptide is an alkylamide, the resin is cleaved by aminolysis with an alkylamine. Alternatively, the peptide can be removed by transesterification, e.g. with methanol, followed by aminolysis or by direct transamidation. The protected peptide can be purified at this point or taken to the next step directly. The removal of the side chain protecting groups can be accomplished using the cleavage cocktail described above. The fully deprotected peptide can be purified by a sequence of chromatographic steps employing any or all of the following types: ion exchange on a weakly basic resin (acetate form); hydrophobic adsorption chromatography on underivitized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

Methods of Use

Also provided herein are methods of use of the compounds or compositions described herein. Also provided herein are methods for treating a disease or pathology in a subject in need thereof comprising administering to the subject an effective amount of any of the compounds or compositions described herein.

Also provided herein are methods of treating, preventing, or ameliorating cancer in a subject. The methods include administering to a subject an effective amount of one or more of the compounds or compositions described herein, or a pharmaceutically acceptable salt thereof. The compounds and compositions described herein or pharmaceutically acceptable salts thereof are useful for treating cancer in humans, e.g., pediatric and geriatric populations, and in animals, e.g., veterinary applications. The disclosed methods can optionally include identifying a patient who is or can be in need of treatment of a cancer. Examples of cancer types treatable by the compounds and compositions described herein include bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. Further examples include cancer and/or tumors of the anus, bile duct, bone, bone marrow, bowel (including colon and rectum), eye, gall bladder, kidney, mouth, larynx, esophagus, stomach, testis, cervix, mesothelioma, neuroendocrine, penis, skin, spinal cord, thyroid, vagina, vulva, uterus, liver, muscle, blood cells (including lymphocytes and other immune system cells). Further examples of cancers treatable by the compounds and compositions described herein include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

The methods of treatment or prevention of cancer described herein can further include treatment with one or more additional agents (e.g., an anti-cancer agent or ionizing radiation). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents.

For example, the compounds or compositions or pharmaceutically acceptable salts thereof as described herein can be combined into a pharmaceutical composition with an additional anti-cancer agent, such as 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, -Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR. The additional anti-cancer agent can also include biopharmaceuticals such as, for example, antibodies.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease.

Also described herein are methods of killing a tumor cell in a subject. The method includes contacting the tumor cell with an effective amount of a compound or composition as described herein, and optionally includes the step of irradiating the tumor cell with an effective amount of ionizing radiation. Additionally, methods of radiotherapy of tumors are provided herein. The methods include contacting the tumor cell with an effective amount of a compound or composition as described herein, and irradiating the tumor with an effective amount of ionizing radiation. As used herein, the term ionizing radiation refers to radiation comprising particles or photons that have sufficient energy or can produce sufficient energy via nuclear interactions to produce ionization. An example of ionizing radiation is x-radiation. An effective amount of ionizing radiation refers to a dose of ionizing radiation that produces an increase in cell damage or death when administered in combination with the compounds described herein. The ionizing radiation can be delivered according to methods as known in the art, including administering radiolabeled antibodies and radioisotopes.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection. Prophylactic administration can be used, for example, in the chemopreventative treatment of subjects presenting precancerous lesions, those diagnosed with early stage malignancies, and for subgroups with susceptibilities (e.g., family, racial, and/or occupational) to particular cancers. Therapeutic treatment involves administering to a subject a therapeutically effective amount of the compounds and compositions or pharmaceutically acceptable salts thereof as described herein after cancer is diagnosed.

In some examples of the methods of treating of treating, preventing, or ameliorating cancer or a tumor in a subject, the compound or composition administered to the subject can comprise a therapeutic moiety that can comprise a targeting moiety that can act as an inhibitor against Ras (e.g., K-Ras), PTP1B, Pin1, Grb2 SH2, or combinations thereof.

The disclosed subject matter also concerns methods for treating a subject having a metabolic disorder or condition. In one embodiment, an effective amount of one or more compounds or compositions disclosed herein is administered to a subject having a metabolic disorder and who is in need of treatment thereof. In some examples, the metabolic disorder can comprise type II diabetes. In some examples of the methods of treating of treating, preventing, or ameliorating the metabolic disorder in a subject, the compound or composition administered to the subject can comprise a therapeutic moiety that can comprise a targeting moiety that can act as an inhibitor against PTP1B. In one particular example of this method the subject is obese and the method comprises treating the subject for obesity by administering a composition as disclosed herein.

The disclosed subject matter also concerns methods for treating a subject having an immune disorder or condition. In one embodiment, an effective amount of one or more compounds or compositions disclosed herein is administered to a subject having an immune disorder and who is in need of treatment thereof. In some examples of the methods of treating of treating, preventing, or ameliorating the immune disorder in a subject, the compound or composition administered to the subject can comprise a therapeutic moiety that can comprise a targeting moiety that can act as an inhibitor against Pin1.

The disclosed subject matter also concerns methods for treating a subject having cystic fibrosis. In one embodiment, an effective amount of one or more compounds or compositions disclosed herein is administered to a subject having cystic fibrosis and who is in need of treatment thereof. In some examples of the methods of treating the cystic fibrosis in a subject, the compound or composition administered to the subject can comprise a therapeutic moiety that can comprise a targeting moiety that can act as an inhibitor against CAL PDZ.

Compositions, Formulations and Methods of Administration

Also disclosed herein are compositions comprising the compounds described herein.

Also disclosed herein are pharmaceutically-acceptable salts and prodrugs of the disclosed compounds. Pharmaceutically-acceptable salts include salts of the disclosed compounds that are prepared with acids or bases, depending on the particular substituents found on the compounds. Under conditions where the compounds disclosed herein are sufficiently basic or acidic to form stable nontoxic acid or base salts, administration of the compounds as salts can be appropriate. Examples of pharmaceutically-acceptable base addition salts include sodium, potassium, calcium, ammonium, or magnesium salt. Examples of physiologically-acceptable acid addition salts include hydrochloric, hydrobromic, nitric, phosphoric, carbonic, sulfuric, and organic acids like acetic, propionic, benzoic, succinic, fumaric, mandelic, oxalic, citric, tartaric, malonic, ascorbic, alpha-ketoglutaric, alpha-glycophosphoric, maleic, tosyl acid, methanesulfonic, and the like. Thus, disclosed herein are the hydrochloride, nitrate, phosphate, carbonate, bicarbonate, sulfate, acetate, propionate, benzoate, succinate, fumarate, mandelate, oxalate, citrate, tartarate, malonate, ascorbate, alpha-ketoglutarate, alpha-glycophosphate, maleate, tosylate, and mesylate salts. Pharmaceutically acceptable salts of a compound can be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The disclosed compositions are bioavailable and can be delivered orally. Oral compositions can be tablets, troches, pills, capsules, and the like, and can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are kits that comprise a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

A number of embodiments of the invention have been described. Nevertheless, it will be understood that various modifications may be made without departing from the spirit and scope of the invention. Accordingly, other embodiments are within the scope of the following claims.

EXAMPLES

The following examples are set forth to illustrate the methods and results according to the disclosed subject matter. These examples are not intended to be inclusive of all aspects of the subject matter disclosed herein, but rather to illustrate representative methods and results. These examples are not intended to exclude equivalents and variations which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions.

Reagents for peptide synthesis were purchased from Advanced ChemTech (Louisville, KY), NovaBiochem (La Jolla, CA), or Anaspec (San Jose, CA). 2,2'-Dipyridyl disulfide, Lissamine rhodamine B sulfonyl chloride, fluorescein isothiocyanate (FITC), dexamethasone (Dex), coenzyme A trilithium salt, FITC-labeled dextran (dextran$^{FITC}$) and human serum were purchased from Sigma-Aldrich (St. Louis, MO). Cell culture media, fetal bovine serum (FBS), penicillin-streptomycin, 0.25% trypsin-EDTA, Hoescht 33342, Alexa488-labeled dextran (dextran$^{Alexa488}$), Dulbecco's phosphate-buffered saline (DPBS) (2.67 mM potassium chloride, 1.47 mM potassium phosphate monobasic, 137 mM sodium chloride, 8.06 mM sodium phosphate dibasic), and Lipofectamine 2000 were purchased from Invitrogen (Carlsbad, CA). PD-10 desalting columns were purchased from GE-Healthcare (Piscataway, NJ). Nuclear staining dye DRAQ5™ was purchased from Thermo Scientific (Rockford, IL), while cell proliferation kit (MTT) was purchased from Roche (Indianapolis, IN). Anti-phosphotyrosine (pY) antibody (clone 4G10) was purchased from Millipore (Temecula, CA).

Rink resin LS (100-200 mesh, 0.2 mmol/g) was purchased from Advanced ChemTech. LC-SMCC (succinimidyl-4-[N-maleimidomethyl] cyclohexane-1-carboxy-[6-amidocaproate]) was purchased from Thermo Scientific (Rockford, IL), while 1-palmitoyl-2-oleoyl-sn-glycero-3-phosphocholine (POPC), 1-palmitoyl-2-oleoyl-sn-glycero-3-phospho(1'-rac-glycerol) (sodium salt) (POPG), 1-palmitoyl-2-oleoyl-sn-glycero-3-phophoethanolamine (POPE), sphingomyelin (Brain, Porcine), and cholesterol were purchased from Avanti Polar Lipids (Alabaster, AL). Heparan sulfate (HO-03103, Lot #HO-10697) was obtained from Celcus Laboratories (Cincinnati, OH).

Peptides were synthesized on Rink Resin LS (0.2 mmol/g) using standard Fmoc chemistry. The typical coupling reaction contained 5 equiv of Fmoc-amino acid, 5 equiv of 2-(7-aza-1H-benzotriazole-1-yl)-1,1,3,3-tetramethyluronium hexafluorophosphate (HATU) and 10 equiv of diisopropylethylamine (DIPEA) and was allowed to proceed with mixing for 75 min. After the addition of the last (N-terminal) residue, the allyl group on the C-terminal Glu residue was removed by treatment with $Pd(PPh_3)_4$ and phenylsilane (0.1 and 10 equiv, respectively) in anhydrous DCM (3×15 min). The N-terminal Fmoc group was removed by treatment with 20% piperidine in DMF and the peptide was cyclized by treatment with benzotriazole-1-yl-oxy-tris-pyrrolidino-phosphonium hexafluorophosphate (PyBOP)/HOBt/DIPEA (5, 5, and 10 equiv) in DMF for 3 h. The peptides were deprotected and released from the resin by treatment with 82.5:5:5:5:2.5 (v/v) TFA/thioanisole/water/phenol/ethanedithiol for 2 h. The peptides were triturated with cold ethyl ether (3×) and purified by reversed-phase HPLC on a $C_{18}$ column. The authenticity of each peptide was confirmed by MALDI-TOF mass spectrometry.

Peptide labeling with FITC was performed by dissolving the purified peptide (~1 mg) in 300 μL of 1:1:1 (vol/vol) DMSO/DMF/150 mM sodium bicarbonate (pH 8.5) and mixing with 10 μL of FITC in DMSO (100 mg/mL). After 20 min at room temperature, the reaction mixture was subjected to reversed-phase HPLC on a C18 column to isolate the FITC-labeled peptide. To generate rhodamine- and Dex-labeled peptides (FIG. 2), an $N^{\varepsilon}$-4-methoxytrityl-L-lysine was added to the C-terminus. After the solid phase peptide synthesis, the lysine side chain was selectively deprotected using 1% (v/v) trifluoroacetic acid in $CH_2Cl_2$. The resin was incubated with Lissamine rhodamine B sulfonyl chloride/DIPEA (5 equiv each) in DMF overnight. The peptides were fully deprotected, triturated with diethyl ether, and purified by HPLC. The Dex-labeled peptide was produced by incubating the resin with dexamethasone-21-thiopropionic acid/HBTU/DIPEA (5, 5, and 10 equiv) in DMF for 3 h (Appelbaum, J S et al. *Chem. Biol.,* 2012, 19, 819-830). The peptide was then deprotected, triturated, and purified by HPLC. Bicyclic peptides, phosphocoumaryl aminopropionic acid (pCAP), and pCAP-containing peptides (PCPs) were synthesized as previously described (Lian, W et al. *J. Am. Chem. Soc.,* 2013, 135, 11990-11995;

Mitra, S and Barrios, A M. *Bioorg. Med. Chem. Lett.,* 2005, 15, 5124-5145; Stanford, S M et al. *Proc. Natl. Acad. Sci. U.S.A.,* 2012, 109, 13972-13977). The authenticity of each peptide was confirmed by MALDI-TOF mass spectrometry.

Example 1

Four 14-aa cyclic peptides (Table 6, BH1-4), which contained the -D-Pro-L-Pro- motif for induction of the beta-hairpin structure, were prepared. In these peptides different combinations of six arginine and hydrophobic residues surrounding the D-Pro-L-Pro motif for potential cellular uptake, and a pentaalanine sequence as a mock cargo, were used (FIG. 1). All of the peptides also contained a Gln residue for cyclization and attachment to the solid support. The peptides were labeled with a naphthofluorescein (NF) at the side chain of a miniPEG-Lys moiety added to the Gln side chain. An NF-labeled cyclic CPP cyclo (FΦRRRRQ) (CPP1) (SEQ ID NO: 131) was used as a benchmark to assess the cellular entry efficiency of the beta-hairpin peptides.

HeLa cells were treated with 5 μM peptide for 2 h, and their cell uptake efficiencies were determined by flow cytometry analysis. The mean fluorescence intensity (MFI) values derived from cytometry analyses reflect the amounts of peptides inside the cytosol and nucleus, whereas any NF-labeled peptide entrapped inside the acidic endosomes are invisible under the experimental conditions (Id.; Qian, Z et al. *Chem. Commun.* 2015, 51, 2162-2165) cellular uptake activity. The cellular entry efficiency was improved by inverting the stereochemistry of different residues in BH4 (i.e., replacement of L- with D-amino acids), producing diastereomers BH5-8 (Table 6). Remarkably, replacement of L-Arg-5 (which is immediately N-terminal to D-Pro) with a D-arginine (r) improved the cytosolic entry efficiency by 6-fold (Table 6, compares peptides BH4 and BH6). Inversion of configuration of Arg-9 or Nal-4 also substantially improved cellular entry (5- and 3-fold higher activities for BH7 and BH8, respectively). On the other hand, substitution of D-Arg for Arg-8 had only minor effect (Table 6, BH5). These results once again demonstrate that a proper spatial arrangement of the arginine and hydrophobic side chains is important for high-affinity binding to the plasma and endosomal membranes of mammalian cells and consequently the cytosolic entry efficiency.

To evaluate the cargo capacity of these beta-hairpin CPPs, the pentaalanine cargo motif of BH6 was replaced with positively-charged (RARQRA; SEQ ID NO:153), negatively-charged (DADQDA; SEQ ID NO:154), and neutral but longer peptide cargos (SASAQSAS; SEQ ID NO:156) to give peptides BH9-11 (Table 6). All three peptides entered cells efficiently, although the cyclic peptide containing the negatively charged cargo (BH10) had the lowest delivery efficiency (as expected).

Example 2

Cell-permeable, biologically active cyclic β-hairpin peptide inhibitors against the Keap1-Nrf2 interaction were

TABLE 6

Sequences and cellular uptake efficiencies of β-hairpin peptidomimetics.

| SEQ ID No.[a] | Peptide ID | Sequence[b] | Cellular Uptake (MFINF, %) |
|---|---|---|---|
| 140 | BH1 | cyclo(A-A-F-Φ-R-p-P-R-R-R-A-A-A-Q)-miniPEG-K(NF) | 66 ± 12 |
| 141 | BH2 | cyclo(A-A-F-R-R-p-P-R-R-Φ-A-A-A-Q)-miniPEG-K(NF) | 24 ± 1 |
| 142 | BH3 | cyclo(A-A-F-Φ-F-p-P-R-R-R-A-A-A-Q)-miniPEG-K(NF) | 30 ± 6 |
| 143 | BH4 | cyclo(A-A-F-Φ-R-p-P-R-R-F-A-A-A-Q)-miniPEG-K(NF) | 73 ± 6 |
| 144 | BH5 | cyclo(A-A-F-Φ-R-p-P-r-R-F-A-A-A-Q)-miniPEG-K(NF) | 102 ± 45 |
| 145 | BH6 | cyclo(A-A-F-Φ-r-p-P-R-R-F-A-A-A-Q)-miniPEG-K(NF) | 431 ± 169 |
| 146 | BH7 | cyclo(A-A-F-Φ-R-p-P-R-r-F-A-A-A-Q)-miniPEG-K(NF) | 363 ± 213 |
| 147 | BH8 | cyclo(A-A-F-φ-R-p-P-R-R-F-A-A-A-Q)-miniPEG-K(NF) | 235 |
| 148 | BH9 | cyclo(R-A-F-Φ-r-p-P-R-R-F-R-A-R-Q)-miniPEG-K(NF) | 104 ± 27 |
| 149 | BH10 | cyclo(D-A-F-Φ-r-p-P-R-R-F-D-A-D-Q)-miniPEG-K(NF) | 44 ± 19 |
| 150 | BH11 | cyclo(S-A-S-F-Φ-r-p-P-R-R-F-S-A-S-A-Q)-miniPEG-K(NF) | 245 ± 16 |
| 151 | BH12 | cyclo(A-E-T-G-E-F-L-F-Φ-r-p-P-R-R-F-L-Q)-miniPEG-K(NF) | 575 ± 239 |
| 152 | CPP1 | cyclo(F-Φ-R-R-R-R-Q)-miniPEG-K(NF) | 100 |

[a]underlined portion only.
[b]Φ = L-2-naphthylalanine, φ = D-2-naphthylalanine; f = D-phenylalanine; r = D-arginine; p = D-proline; miniPEG = 8-amino-3,6-dioxaoctanoic acid; NF = naphthofluorescein.

Peptides BH1-4 entered HeLa cells with efficiencies 30-70% of that of CPP1. Peptide BH4, which contained three hydrophobic residues and three arginines, was taken up most efficiently by HeLa cells and selected for further optimization. It was previously found that the stereochemical configuration of CPP residues can greatly affect the designed. The Keap1-Nrf2-ARE signaling pathway is an essential response mechanism to endogenous and exogenous stresses caused by reactive oxygen species (ROS) and electrophiles (Taguchi, K et al. *Genes Cells* 2011, 16, 123-140; Kansanen, E et al. *Redox Biol.* 2013, 1, 45-49). Under basal conditions, Kelch-like ECH-associated protein-1 (Keap1) negatively regulates the transcriptional activity of nuclear factor erythroid 2-related factor 2 (Nrf2) through an ubiquitin-mediated proteasomal degradation mechanism (Huang, H C et al. *Proc. Natl. Acad. Sci. U.S.A.* 2000, 97, 12475-1248; Ishii, T et al. *J. Biol. Chem.* 2000, 275, 16023-16029). Under oxidative stress conditions, some of the Cys residues on the Keap1 surface become covalently modified, causing the dissociation of the Keap1-Nrf2 interaction. The dissociated Nrf2 translocates into the nucleus, binds to the antioxidant response element (ARE), and up-regulates the expression of anti-oxidative stress response genes (Zhang, D D et al. Mol. Cell. Biol. 2003, 23, 8137-8151). Inhibition of the Keap1-Nrf2 interaction therefore provides a potential therapeutic strategy to protect against oxidative and/or electrophilic stresses, which are implicated in cancer, neurological disease, and autoimmune diseases (Lewis, K N et al. Integr. *Comp. Biol.* 2010, 50, 829-843; Rajendran, P et al. *Clin. Chim. Acta.* 2014, 436, 332-347).

Nrf2 interacts with the two Kelch domains of a Keap1 homodimer through two short peptide motifs, a low-affinity DLG motif ($K_D$~1000 nM) and a high-affinity ETGE motif (SEQ ID NO:158) ($K_D$~5 nM) Tong K I et al. *Mol. Cell. Biol.* 2006, 26, 2887-2900; Tong, K I et al. *Mol. Cell. Biol.* 2007, 27, 7511-7521). Previous studies identified an ETGE-containing 16-mer peptide (AFFAQLQLDEETGEFL or Nrf2-16mer (SEQ ID NO:157); Table 7) as a potent Keap1 ligand ($K_D$~20 nM), which physically blocks the Nrf2-Keap1 interaction. When bound to Keap1, Nrf2-16mer adopts a β-hairpin structure, which is stabilized by hydrogen bonds between Asp and Thr side chains and the peptide backbone. Unfortunately, this high-affinity peptidyl inhibitor is impermeable to cell membrane and has no biological activity in cellular assays.

Figure 2:
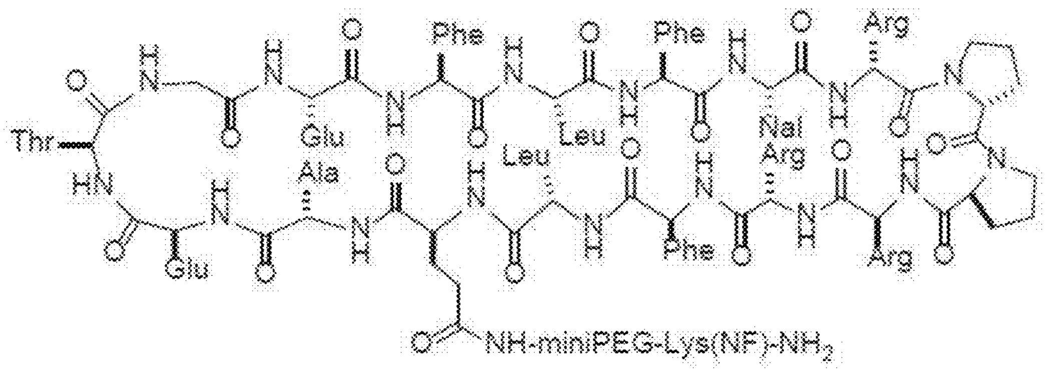
FIG. 2 is the structure of cyclic B-hairpin peptide BH12.

To generate a cell-permeable Keap1-Nrf2 inhibitor, the mock cargo motif of BH6 (pentaalanine) was replaced with the ETGE motif ((SEQ ID NO:158) from Nrf2, $^{76}$LDEETGEFL$^{84}$ (SEQ ID NO:159). The Glu-78 was also replaced with alanine, which was previously shown to enhance the binding affinity to Keap1 (Hancock R et al. *Free Radic. Biol. Med.* 2012, 52, 444-451). Removal of the negative charge is also expected to improve the cellular entry efficiency. To facilitate the quantitation of cellular entry, Asp-77 was replaced with a Glu and attached a miniPEG-Lys(NF) moiety to its side chain, giving peptide BH12 (FIG. 2). Flow cytometry analysis indicated that BH12 retained the cellular entry ability of the parent peptide. In fact, it entered the cytosol of HeLa cells at 5.8-fold higher efficiency than CPP1 (Table 6).

Example 3

To generate cyclic β-hairpin peptides that are both cell-permeable and retain high-affinity binding to Keap1, the structure of BH12 was modified by making various truncations of the cargo motif as well as replacing the Asp residue with Asn, which was expected to increase the cellular uptake (Table 7, BH13-19). The binding affinity of the peptides to Keap1 was determined by using a fluorescence anisotropy-based competition assay, during which increasing concentrations of β-hairpin peptides were added to a reaction containing a fluorescently labeled Nrf2 peptide and Keap1 (Inoyama, D et al. *J. Biomol. Screen.* 2011, 17, 435-447). The percentage of inhibition was calculated from the fluorescence anisotropy decrease by using equation $$\%\ \text{Inhibition} = (FA_{max} - FA_{obs})/(FA_{max} - FA_{min}) \times 100\%$$

and plotted against the inhibitor concentration. The $IC_{50}$ values (inhibitor concentration at which binding by the fluorescent Nrf2 probe was decreased by 50%) were determined by fitting the data to equation $$FA = FA_{min} + (FA_{max} + FA_{min})/\left(1 + 10^{(x - logIC50)}\right)$$

where x is the logarithm of the inhibitor concentration, while $FA_{max}$, $FA_{min}$, and $FA_{obs}$ are the anisotropy values of Keap1 and probe only (no competitor), the unbound probe only, and the experimental samples, respectively.

TABLE 7

Sequences and $IC_{50}$ Values for Inhibition of the Keap1-Nrf2 Interaction.

| SEQ ID NO.[a] | Peptide ID | Sequence[b] | $IC_{50}$ (nM) |
|---|---|---|---|
| 160 | Nrf2-16mer | H-A-F-F-A-Q-L-Q-L-D-E-E-T-G-E-F-L-OH | 163 ± 11 |
| 161 | BH13 | cyclo(F-F-Φ-r-p-P-R-R-F-Q-L-D-P-E-T-G-E) | 153 ± 6 |
| 162 | BH14 | cyclo(F-F-Φ-r-p-P-R-R-F-Q-L-N-A-E-T-G-E) | 1400 ± 130 |
| 163 | BH15 | cyclo(F-F-Φ-r-p-P-R-R-F-L-D-P-E-T-G-E) | 164 ± 7 |
| 164 | BH16 | cyclo(F-F-Φ-r-p-P-R-R-F-L-N-A-E-T-G-E) | 1470 ± 130 |
| 165 | BH17 | cyclo(F-Φ-r-p-P-R-R-F-L-D-P-E-T-G-E) | 163 ± 9 |
| 166 | BH18 | cyclo(F-Φ-r-p-P-R-R-F-L-N-A-E-T-G-E) | 1400 ± 150 |
| 167 | BH19 | cyclo(F-Φ-r-p-P-R-R-F-N-A-E-T-G-E) | 5540 ± 760 |

[a]underlined portion only.
[b]Φ = L-2-naphthylalanine; p = D-proline.

60

Figure 3:
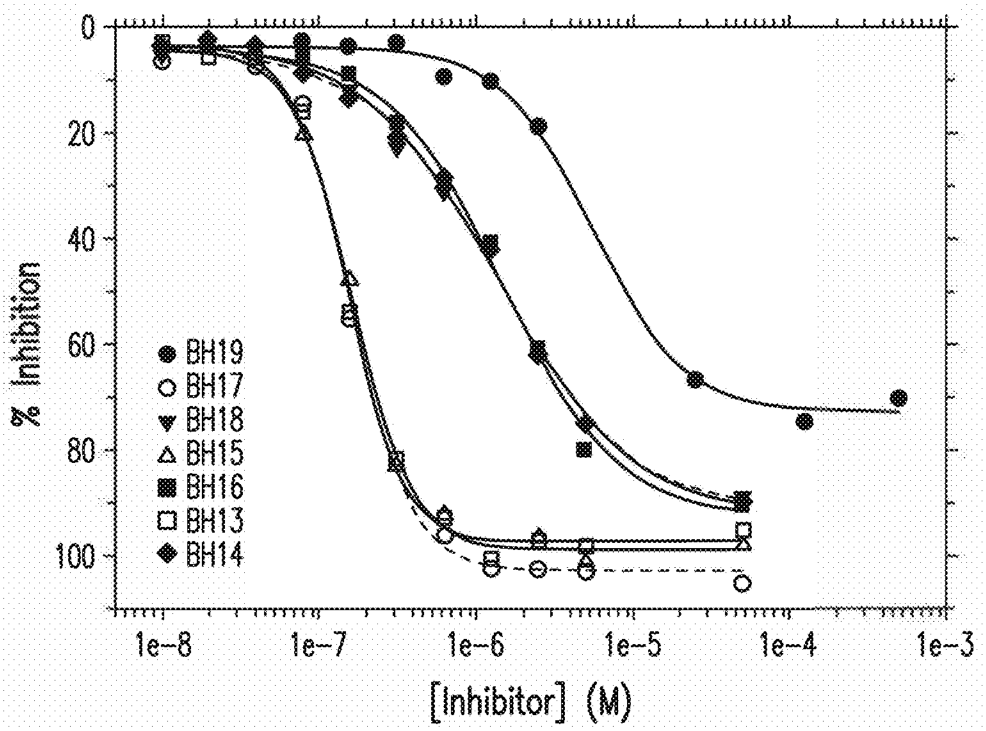
FIG. 3 is a graph of inhibition of the Keap1-Nrf2 peptide interaction by different cyclic β-hairpin peptides as determined by the FA-based competition assay.

Peptides BH13, BH15, and BH17, which contain 9-aa, 8-aa, and 7-aa cargo sequences, respectively, all inhibited the Keap1-Nrf2 interaction with similar potencies to the linear Nrf2-16mer peptide ($IC_{50}$~160 nM) (FIG. 3) (Lo, S C et al. *EMBO J.* 2006, 25, 3605-3617). Replacement of the Asp-Pro motif with Asn-A1a with the intention of improving the cellular uptake, however, significantly decreased the affinity of the peptides for Keap1 (by ~10-fold) (Table 7, compare BH13 vs BH14, BH15 vs BH16, or BH17 vs BH18). Further truncation of the cargo sequence to 6-aa also greatly reduced the inhibition potency (by 34-fold) (Table 7, BH19). These data indicate that effective binding to Keap1 requires a minimal cargo sequence of LDPETGE (SEQ ID NO:139).

Example 4

Figure 4:
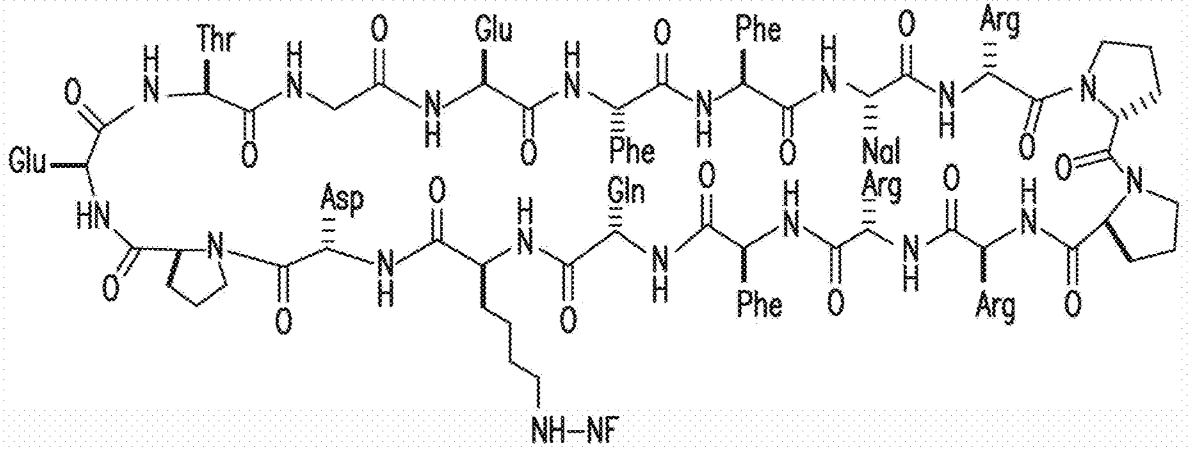
FIG. 4 is the structure of cyclic B-hairpin peptide BH20.
Figure 5:
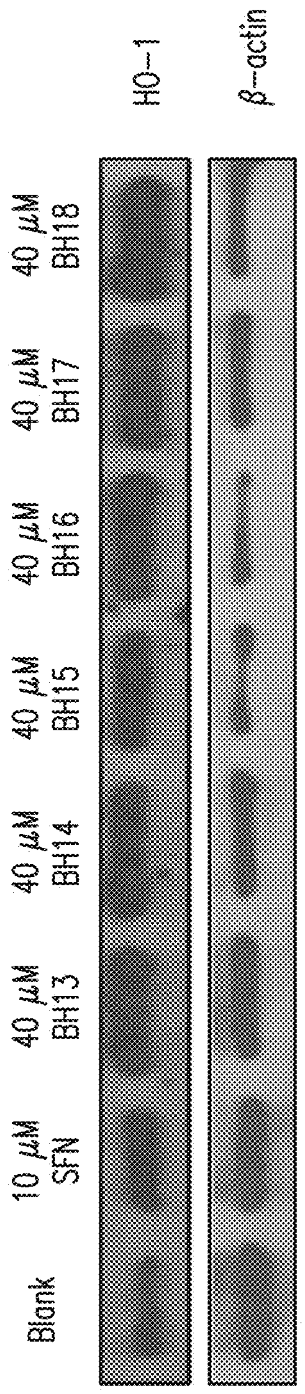
FIG. 5 is an image from a Western blot analysis of HO-1 protein levels in HEK293 cells untreated or after treatment with SFN (10 μM) or a cyclic β-hairpin peptide (40 μM).

To test whether the above Keap1-Nrf2 inhibitor peptides are cell-permeable, cyclic peptides BH13 and BH17 had the Leu residue in the cargo sequence replaced with a Lys residue, and the peptides were labeled with NF at the Lys side chain (FIG. 4 and Table 8, BH20 and BH21). Flow cytometry analysis showed that both BH20 and BH21 entered the cytosol of HeLa cells, but less efficiently than BH6 and BH12, indicating that the presence of negatively charged residues near the CPP motif (e.g., Asp) decreases the cellular entry efficiency of the cyclic β-hairpin peptides. To test the importance of the β-hairpin structure to cellular uptake, the -D-Pro-L-Pro- motif of peptide BH20 was replaced with -L-Pro-D-Pro-, which was previously reported to disrupt the β-turn structure (Table 8, peptide BH22). BH22 is indeed ~2-fold less efficient for cellular entry than BH20.

TABLE 8

Cellular Uptake Efficiency of Various Keap1-Nrf2 Inhibitors.

| SEQ ID. NO.[a] | Peptide ID | Sequence | Cellular Uptake (MFI$^{NF}$, %) |
|---|---|---|---|
| 168 | BH20 | cyclo[F-F-Φ-r-p-P-R-R-F-Q-K(NF)-D-P-E-T-G-E] | 122.4 |
| 169 | BH21 | cyclo[F-Φ-r-p-P-R-R-F-K(NF)-D-P-E-T-G-E] | 44.6 |
| 170 | BH22 | cyclo[F-F-Φ-r-P-p-R-R-F-Q-K(NF)-D-P-E-T-G-E] | 56.9 |
| 171 | CPP1 | cyclo(F-Φ-R-R-R-R-Q)-miniPEG-K(NF) | 100 |

[a]underlined portion only.
[b]Φ = L-2-naphthylalanine; p = D-proline; Rho = tetramethylrhodamine.

Figure 6:
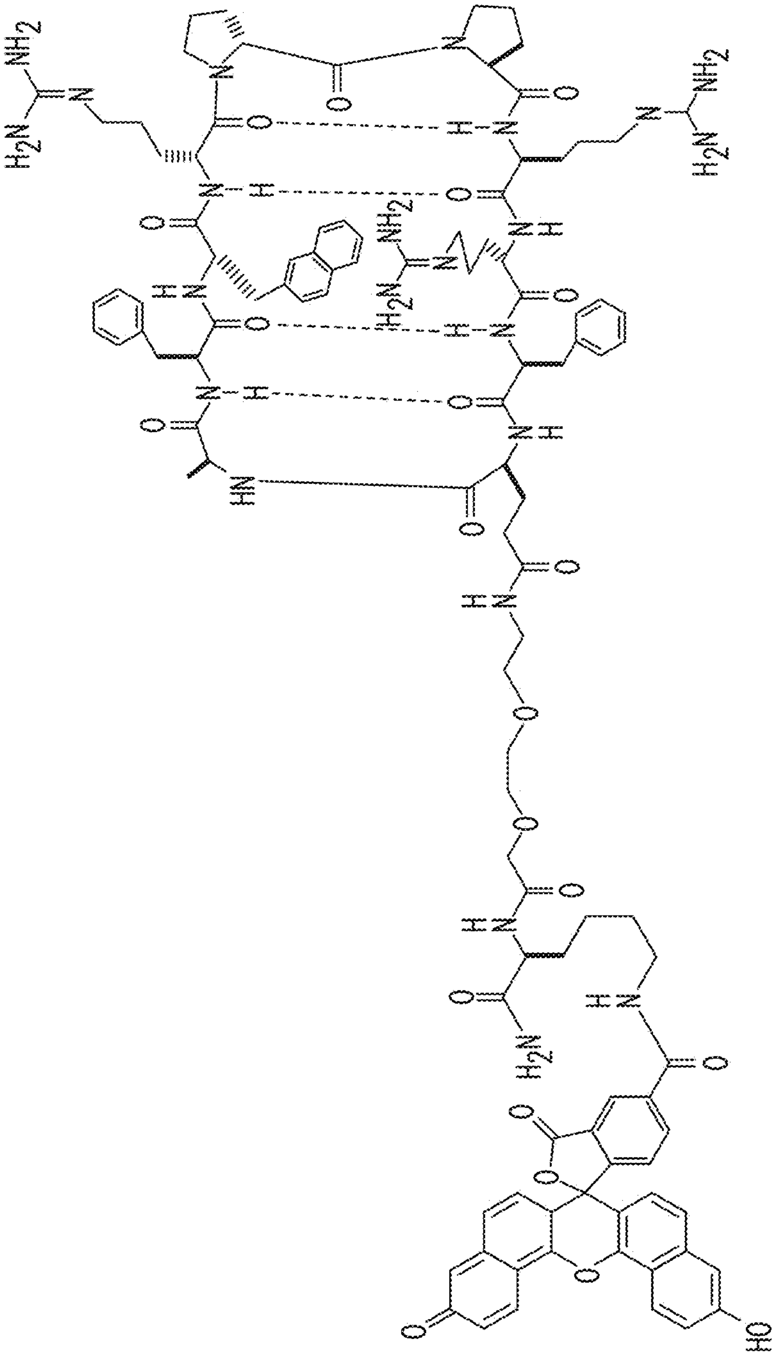
FIG. 6 is the structure of a beta-hairpin transporter, BHT1, labeled with a miniPEG linker and naphthofluorescein (NF).

The cellular activity of Keap1-Nrf2 inhibitors BH13-18 was assessed by examining their effects on the expression levels of HO-1 protein, by anti-HO1 immunoblot analysis. HO-1 is an antioxidant enzyme under the transcriptional control of Nrf2 binding to the ARE, and disruption of the Keap1-Nrf2 interaction is expected to increase the protein level of HO-1. Treatment of HEK293 cells with 40 μM peptides BH13-18 for 16 h significantly increased the HO-1 protein expression relative to the untreated control (FIG. 6). Sulforaphane (SFN), a small-molecule inhibitor of Keap1 used as a positive control in the experiment, also increased the HO-1 level at 10 μM concentration.

Example 5

The cellular activity of Keap1-Nrf2 Inhibitor BH15 was characterized, and it was observed that BH15 is biologically active in cell-based assays. Varying doses of BH15 were provided to HEK293 cells in culture. After a period of time, the cells were lysed, and cytosolic fractions were separated from nuclear fractions.

Figure 7:
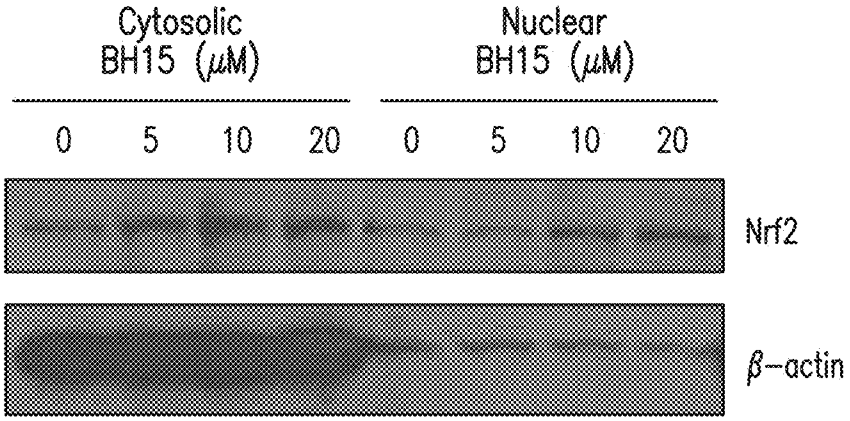
FIG. 7 shows western blots which demonstrate the effect of peptide BH15 on the protein level of Nrf2 in the cytoplasm and nucleus of HEK293 cells. β-actin is used as loading control.
Figure 8:
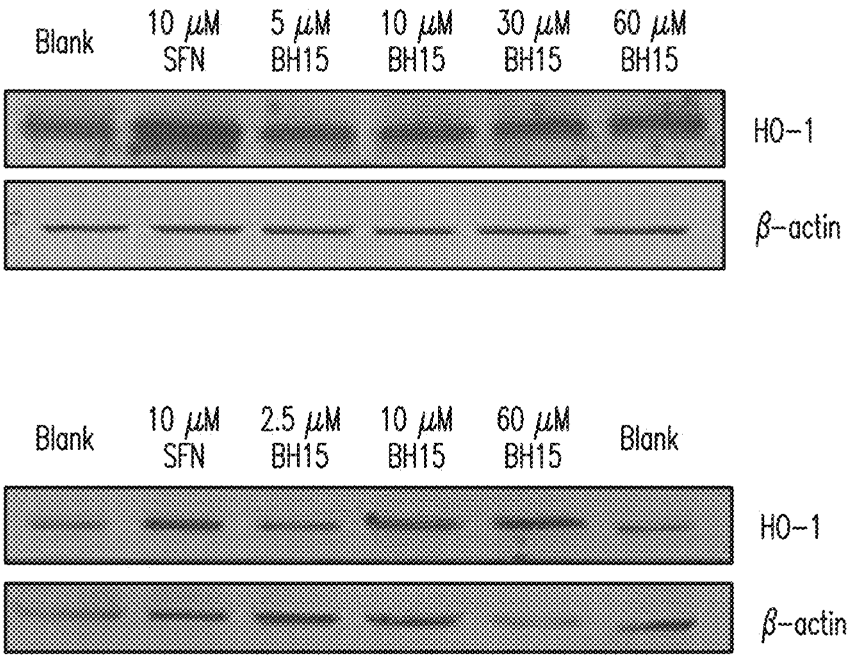
FIG. 8 is a western blot showing the effect of peptide BH15 on the protein level of HO-1, a protein downstream of the Keap1-Nrf2-ARE pathway. SFN, a small-molecule positive control; blank, no inhibitor.

BH15 enters human cells, binds and inhibits the function of Keap1 (which promotes the ubiquitination and degradation of Nrf2), resulting in increased intracellular levels of Nrf2, a transcription factor. As expected, BH15 dose-dependently increased the Nrf2 levels in both fractions (FIG. 7). This in turn results in the increased levels of HO-1, a protein whose expression is controlled by Nrf2. BH15 dose-dependently increased the HO-1 level (FIG. 8). These results demonstrate the validity of designing cell-permeable β-hairpin shaped cyclic peptides.

Example 6

To demonstrate the generality of the β-hairpin inhibitor design strategy, a cyclic peptidyl inhibitor against the Grb2 SH2 domain was designed as a potential anticancer agent. Grb2 is an adaptor protein that mediates many cellular signal transduction pathways. Grb2 contains an SH2 domain and two SH3 domains. Its SH2 domain interacts with specific phosphotyrosine (pY)-containing sequences in cell surface receptors such as the epidermal growth factor receptor (EGFR) and recruits guanosine nucleotide exchange factors (e.g., SOS) to the cell surface, thereby activating the Ras protein and downstream signaling pathways. Inhibitors against the Grb2 SH2 domain provide potential anticancer agents. The Grb2 SH2 domain recognizes peptides of the consensus pY—X—N—X, where X is generally a hydrophobic residue such as valine (SEQ ID NO:222). Moreover, X-ray crystal structure of Grb2 SH2 domain bound to pYXNX motifs (SEQ ID NO:222) revealed that the bound peptide is in a β-turn conformation. (M. S. Kimber, et al. (2000) *Mol. Cell,* 5, 1043-1049.)

Figure 9A:
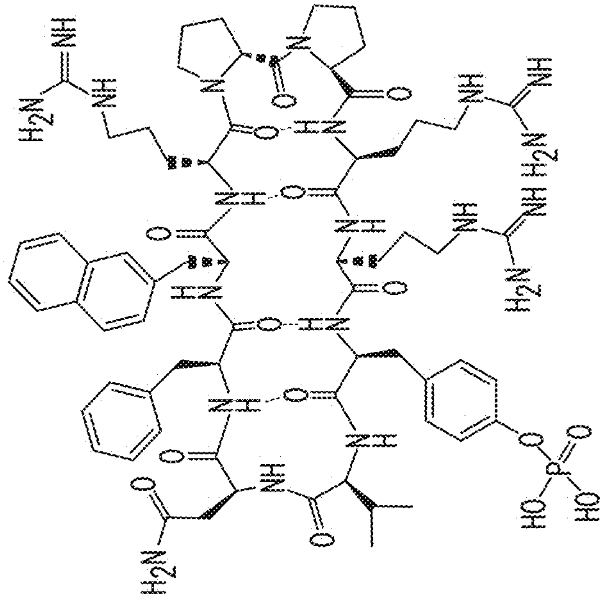
FIG. 9(*a*) is the structure of beta-hairpin Grb2 SH2 inhibitor BH23.

A cycloundecapeptide, cyclo(pY-V-N-F-Φ-r-p-P-R-R; SEQ ID NO:223), which is a fusion of the Grb2 SH2 ligand (pYVNF; SEQ ID NO:224) and BHT1 (FrΦPRR; SEQ ID NO: 225), was designed. In this design, residue Phe serves the dual purposes of cell entry and Grb2 binding (BH23 in FIG. 9*a*). It was envisioned that the D-Pro-L-Pro motif would constrain the cyclic peptide into a β-hairpin structure, while the pYVNF (SEQ ID NO:224) would assume a β-hairpin conformation on the other end for optimal binding to the Grb2 SH2 domain.

Figure 9B:
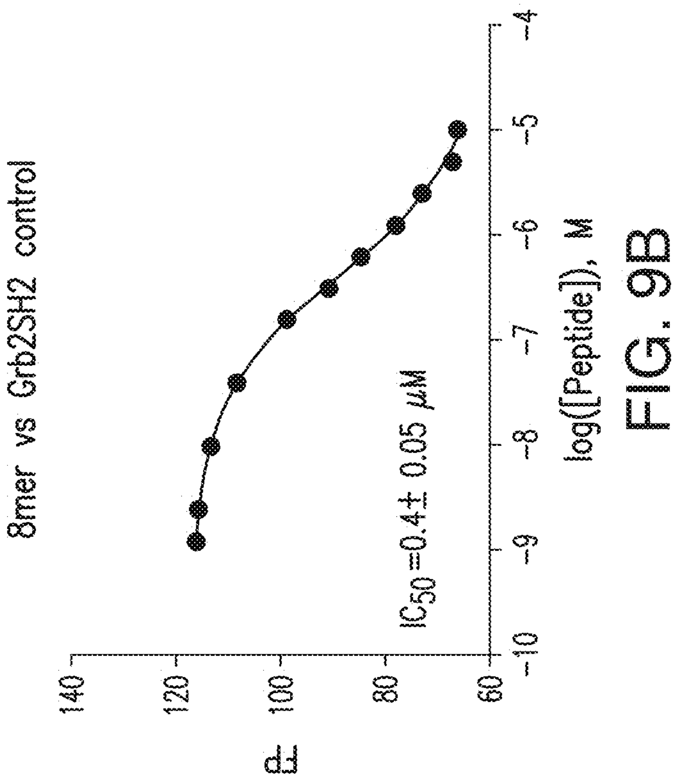
Figure 9C:
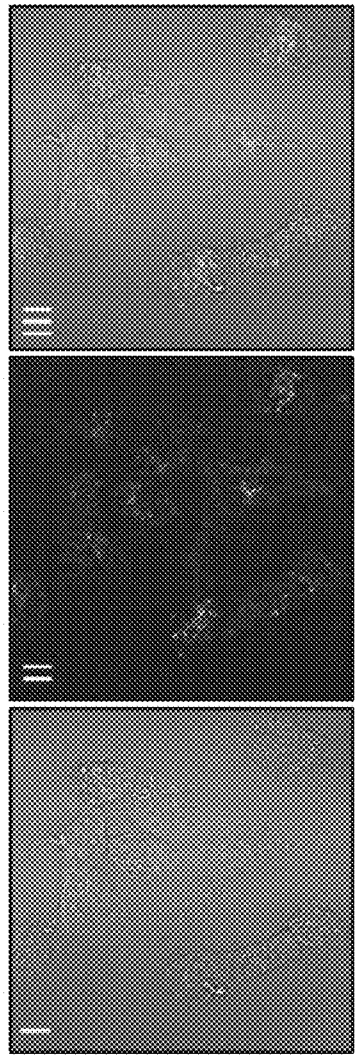
Figure 10A:
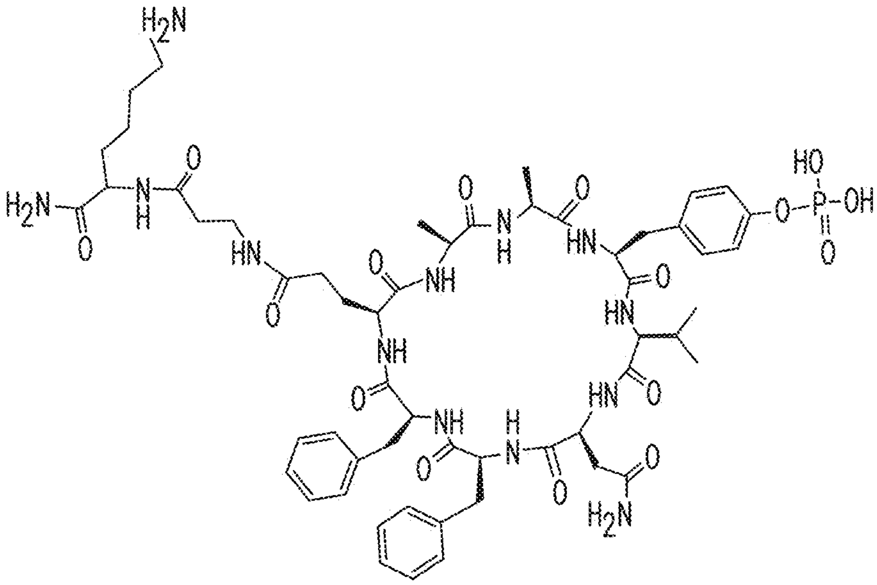
FIG. 10(*a*) is the structure of a Grb2 SH2 ligand.
Figure 10B:
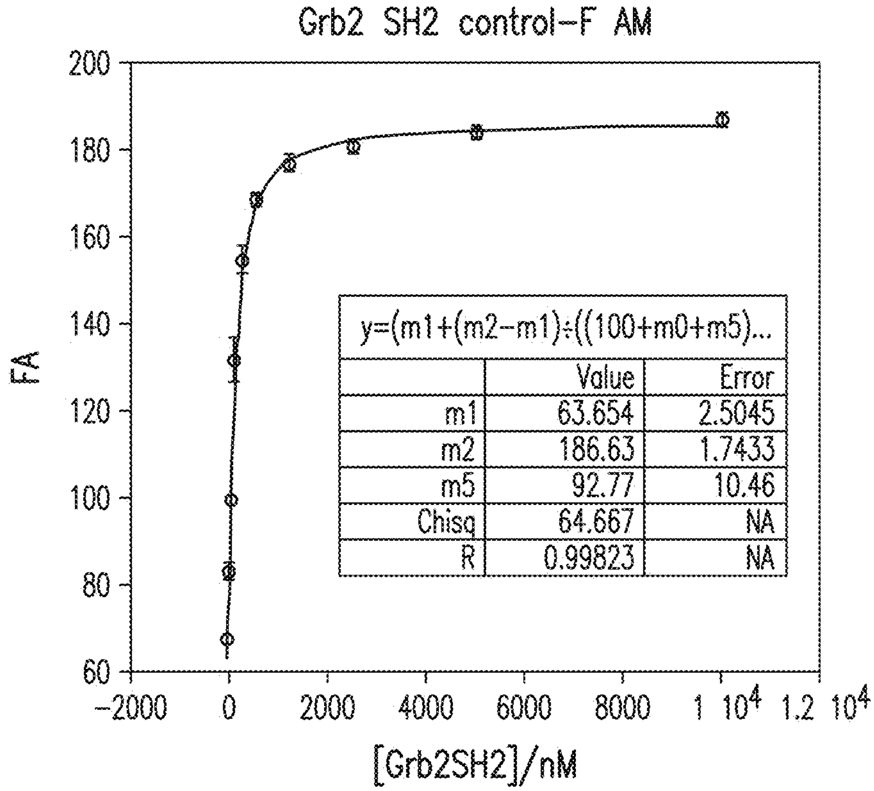
Figure 11:
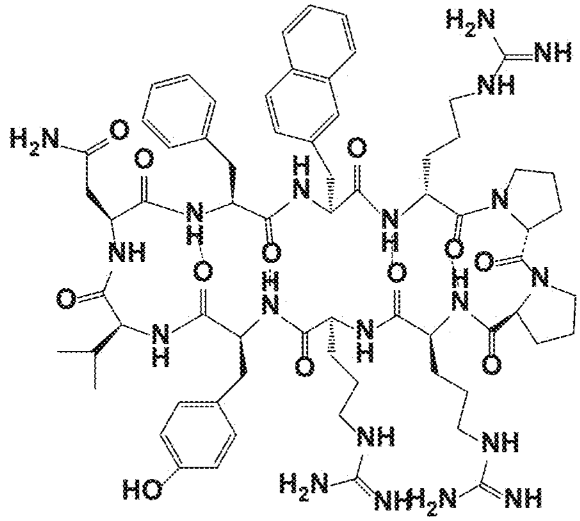
FIG. 11 is the structure of negative control peptide BH24 (pY to Y).
Figure 11:
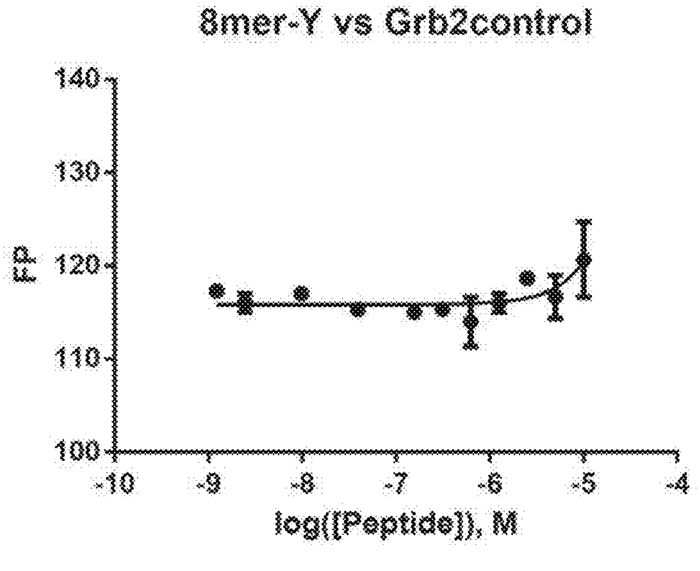
Figure 12:
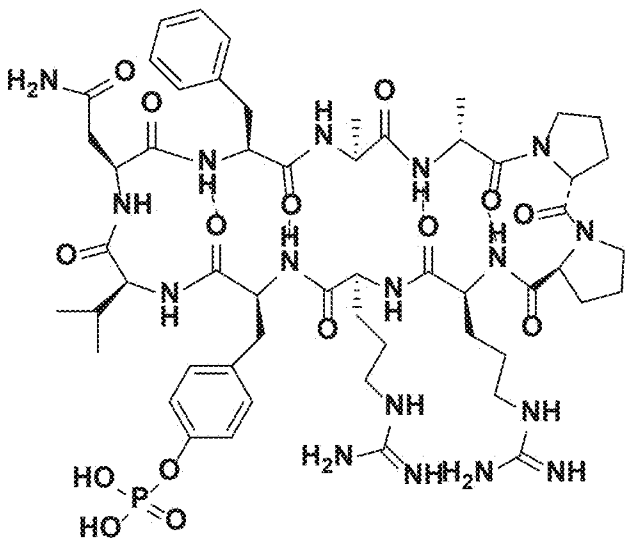
FIG. 12 is the structure of negative control peptide BH25.
Figure 12:
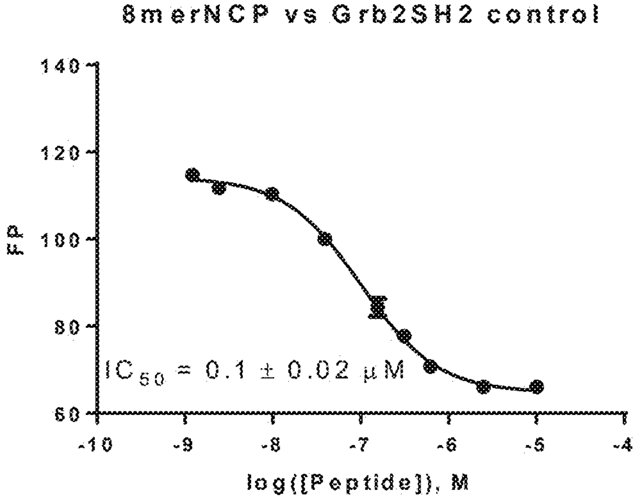

To determine the binding affinity of BH23 for the Grb2 SH2 domain, a previously reported fluorescein (FAM)-labeled cyclic peptidyl ligand of Grb2 SH2 domain, cyclo (AApYVNFFQ)-β-Ala-K(FAM) (SEQ ID NO:226), was synthesized, and its binding affinity for the SH2 domain was measured ($K_D$=92 nM; FIG. 10). The binding affinity of BH23 (unlabeled) for the Grb2 SH2 domain was then determined by examining its ability to compete with the FAM-labeled ligand for binding to the Grb2 SH2 domain by fluorescence polarization (FP). An IC50 value of 0.40 μM was obtained (FIG. 9*b*). Next, BH23 was labeled with NF at the Asn side chain through a miniPEG-Lys linker and its cytosolic entry efficiency was quantitated by treating HeLa cells with 5 μM of the labeled peptide for 2 h before flow cytometry analysis. BH23 showed a cytosolic uptake efficiency that was 4.9-fold higher than CPP9 (100%) in the presence of 10% FBS (Table 9). BH23 was also similarly labeled at the Asn side chain with FAM and its entry into HeLa cells was examined by live-cell confocal microscopy. FAM-labeled BH23 produced predominantly punctate fluorescence, suggesting that it entered the cells by endocytic mechanisms and has relatively poor endosomal escape efficiency, presumably due to the presence of the negatively charged pY immediately next to the CPP sequence (FIG. 9*c*). Two control peptides (BH24 and BH25) were also prepared for cellular assays. BH24 and BH25 are structurally similar to BH23, except that BH24 contained a Tyr instead of the pY residue (FIG. 11), whereas in BH25 the two hydrophobic residues critical for cellular uptake (Nal-arg) were replaced with Ala-ala (FIG. 12). As expected, BH24 showed no detectable binding to the Grb2 SH2 domain (IC50>10 μM; FIG. 11), while BH25 potently bound to the SH2 domain (IC50=0.10 μM; FIG. 12) but had poor cellular uptake.

TABLE 9

Binding affinity of BH23 and control peptides to the Grb2 SH2 domain and their cytosolic entry efficiency.

| Peptide ID | Sequence[a] | IC50 Value (μM)[a] | Cellular Uptake (MFI[NF], %)[b] |
|---|---|---|---|
| CPP9 | cyclo(f-Φ-R-r-R-r-Q)-miniPEG-K(NF) (SEQ ID NO: 227) | — | 100 |
| BH23 | cyclo[F-Φ-r-p-P-R-R-pY-V-N)-[miniPEG-K(NF)](SEQ ID NO: 228) | 0.40 ± 0.05 | 490 ± 185 |
| BH24 | cyclo[F-Φ-r-p-P-R-R-Y-V-N) (SEQ ID NO: 229) | >10 | |
| BH25 | cyclo[F-A-a-p-P-R-R-pY-V-N) (SEQ ID NO: 230) | 0.10 ± 0.02 | |

[a]The IC50 values were determined with unlabeled BH23-25 by a FP-based competition assay.

[b]Hela cells were treated with 5 μM NF-labeled peptide for 2 h in DMEM medium containing 10% FBS and 1% ABS.

Figure 13:
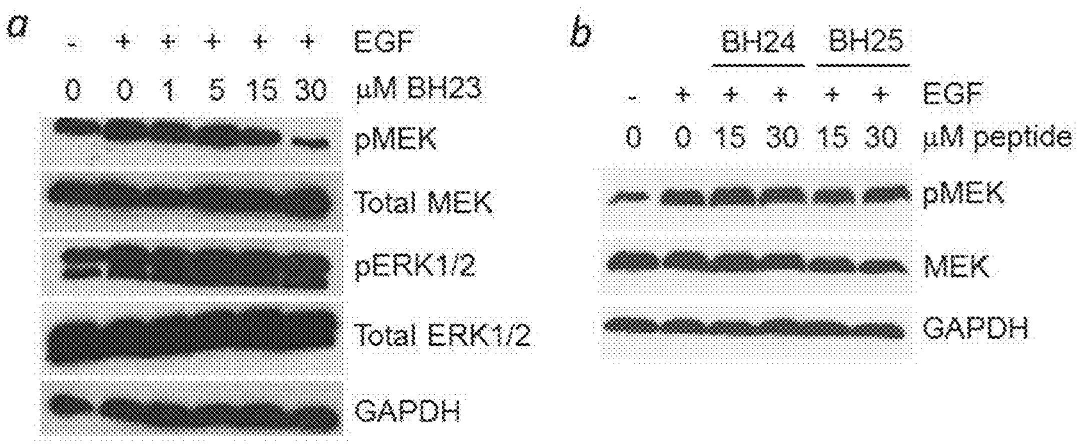
FIG. 13 provides western blots depicting the effect of peptides BH23, BH24, and BH25 on the Grb2/Ras signaling pathway. MDA-MB-468 cells were treated with the indicated concentrations of peptide BH23 (a) or control peptides BH24 and BH25 (b) for 2 h and stimulated with EGF (50 ng/mL) for 10 min. The cells were then lysed and the cell lysates were separated on SDS-PAGE and blotted with antibodies specific for phosphorylated and total kinases in the Ras signaling pathway. Glyceraldehyde 3-phosphate dehydrogenase (GAPDH) was used as the loading control. BH23, but not BH24 or BH25, dose-dependently reduced the levels of phosphor-MEK but not the total protein level of MEK. Inhibition of ERK1/2 phosphorylation was less dramatic, as expected from its further downstream position on the Grb2/Ras signaling pathway.

Φ, L-2-naphthylalanine; p, D-proline; pY, phosphotyrosine; r, D-arginine; NF, naphthofluorescein BH23 and BH24 were tested for their ability to inhibit the Grb2/Ras signaling pathways, by monitoring the phosphorylation of MEK and ERK1/2 kinases downstream of Ras. As shown in FIG. 13, BH23 dose-dependently decreased the phosphorylation of MEK but not the total intracellular level of MEK in MDA-MB-468 breast cancer cells. BH23 also decreased the phosphorylation of ERK1/2, but the effect was less dramatic. In contrast, BH24 or BH25 did not decrease the phosphorylation of MEK.

Example 7

Figure 14A:
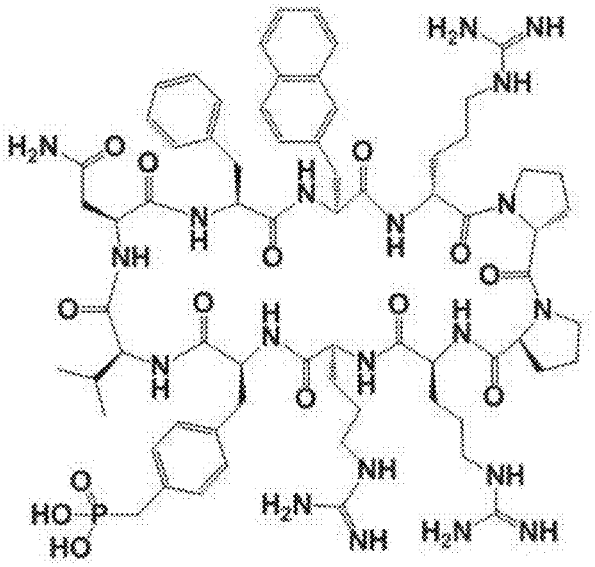
FIG. 14(*a*) is the structure of BH26.
Figure 14B:
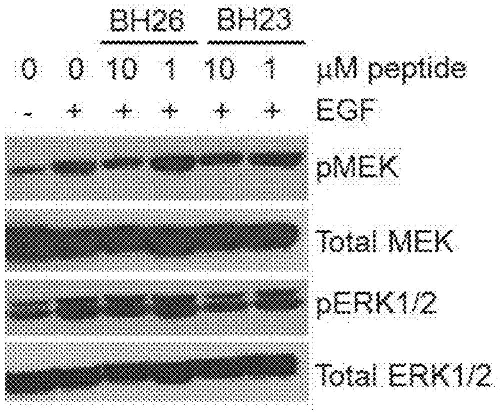

A limitation of BH23 and other pY-containing peptides is that their pY moiety may be dephosphorylated by alkaline phosphatases in serum and protein tyrosine phosphatases inside the cell. To increase the metabolic stability of BH23, the pY residue was replaced with a non-hydrolyzable analog, phosphonomethylphenylalanine (Pmp), to produce peptide BH26 (FIG. 14*a*). BH26 is ~3-fold less potent than BH23 for binding to Grb2 SH2 domain (IC50=1.37±0.5 μM). When tested against MDA-MB-468 cells, BH26 also dose-dependently inhibited the phosphorylation of MEK and ERK1/2, but appeared to be somewhat less potent than BH23 (FIG. 14*b*).

Example 8

A cycloundecapeptide, cyclo(F-Φ-r-p-P-R-R-F-A-A) (SEQ ID NO: 231), was prepared by using the CPP sequence derived from peptide BH6 (FIG. 6). According to the design rules of Robinson and co-workers (Robinson, J A *Acc. Chem. Res.* 2008, 41, 1278-1288), the cycloundecapeptide should form a stable β-hairpin structure through the formation of four intramolecular H-bonds. To generate a site for cargo attachment, the two Ala residues at one end of the hairpin were replaced with a Glu to give peptides BHT1 and BHT2. The structure of BHT1 is shown in FIG. 6 (BHT=β-hairpin transporter).

BHT1 and BHT2 were labeled with naphthofluorescein (NF) and their cytosolic uptake into HeLa cells was determined by flow cytometry (Table 10). BHT1 is a very active CPP, as expected from the earlier data on BH6, with a cytosolic delivery efficiency that is 88% relative to that of CPP9, which is defined as 100%. Surprisingly, BHT2 is much less active (15% efficiency relative to CPP9), despite having the same CPP structure as BHT1.

TABLE 10

Comparison of Cellular Uptake Efficiency of β-hairpin transporters BHT1 and BHT2 and CPP9 into HeLa cells.[a]

| Peptide ID | Sequence | Cellular Uptake ($MFI^{NF}$, %) |
|---|---|---|
| BHT1 | cyclo(AFΦrpPRRFQ)-miniPEG-K(NF) (SEQ ID NO: 232) | 88 ± 11 |
| BHT2 | cyclo(FΦrpPRRFAQ)-miniPEG-K(NF) (SEQ ID NO: 233) | 15 ± 2 |
| CPP9 | cyclo(f-Φ-R-r-R-r-Q)-miniPEG-K(NF) (SEQ ID NO: 227) | 100 |

[a]HeLa cells were treated with 5 μM peptide for 2 h in DMEM medium containing 10% FBS and 1% ABS. Φ, L-2-naphthylalanine, ϕ, D-2-naphthylalanine, r, D-arginine, p, D-proline; miniPEG, 8-amino-3,6-dioxaoctanoic acid; NF, naphthofluorescein.

These data highlight the importance of a proper site for cargo attachment. Presumably, the cargo moiety attached to BHT2 interferes with the interaction between BHT2 and the membrane phospholipids.

Example 9

Additional cell penetrating compounds were prepared and tested for cytosolic delivery. In these compounds there was no beta-hairpin turn creating moiety. These compounds are shown in Table 11.

TABLE 11

Sequences and Cytosolic Delivery Efficiencies of CPPs

| SEQ ID NO.[a] | Sequence[b] | Cellular Uptake ($MFI^{NF}$, %)[c] |
|---|---|---|
| 131 | cyclo(FΦRRRRQ) | 100 ± 6 |
| 234 | cyclo(FFRRRQ) | 65 |
| 235 | cyclo(FFrRrQ) | 122 |
| 236 | cyclo(FFRrRQ) | 40 |
| 237 | cyclo(FRFRRQ) | 15 ± 3 |
| 238 | cyclo(FRRFRQ) | 38 ± 10 |
| 239 | cyclo(FRRRFQ) | 25 ± 4 |
| 240 | cyclo(GΦRRRQ) | 49 ± 5 |
| 241 | cyclo(FFFRAQ) | 52 ± 2 |
| 242 | cyclo(FFFRRQ) | 125 ± 25 |
| 243 | cyclo(FFRRRRQ) | 89 ± 27 |
| 244 | cyclo(FRRFRRQ) | 31 ± 3 |
| 245 | cyclo(FRRRFRQ) | 20 ± 3 |
| 246 | cyclo(RFFRRRQ) | 63 ± 19 |
| 247 | cyclo(RFRRFRQ) | 94 ± 9 |
| 248 | cyclo(FRFRRRQ) | 132 ± 57 |
| 249 | cyclo(FFFRRRQ) | 231 ± 43 |
| 250 | cyclo(FFRRRFQ) | 158 ± 21 |
| 251 | cyclo(FRFFRRQ) | 142 ± 25 |
| 252 | cyclo(RRFFFRQ) | 172 ± 24 |
| 253 | cyclo(FFRFRRQ) | 106 ± 22 |
| 254 | cyclo(FFRRFRQ) | 86 ± 12 |
| 255 | cyclo(FRRFFRQ) | 109 ± 11 |
| 256 | cyclo(FRRFRFQ) | 101 ± 16 |
| 257 | cyclo(FRFRFRQ) | 105 ± 14 |
| 258 | cyclo(RFFRFRQ) | 96 ± 31 |
| 259 | cyclo(GΦRRRRQ) | 55 ± 5 |
| 260 | cyclo(FFFRRRRQ) | 122 ± 20 |
| 261 | cyclo(RFFRRRRQ) | 104 ± 5 |
| 262 | cyclo(RRFFRRRQ) | 115 ± 20 |
| 263 | cyclo(RFFFRRRQ) | 167 ± 10 |
| 264 | cyclo(RRFFFRRQ) | 112 ± 20 |
| 265 | cyclo(FFRRFRRQ) | 46 ± 2 |
| 266 | cyclo(FFRRRRFQ) | 162 ±16 |
| 267 | cyclo(FRRFFRRQ) | 127 ± 22 |
| 268 | cyclo(FFFRRRRRQ) | 145 ± 27 |
| 269 | cyclo(FFFRRRRRRQ) | 141 ± 10 |
| 270 | cyclo(FΦRrRrQ) | 212 ± 42 |
| 271 | cyclo(XXRRRRQ) | 165 ± 22 |

TABLE 11-continued

Sequences and Cytosolic Delivery Efficiencies of CPPs

| SEQ ID NO.[a] | Sequence[b] | Cellular Uptake ($MFI^{NF}$, %)[c] |
|---|---|---|
| 272 | cyclo(FfFRrRQ) | 230 ± 18 |
| 273 | cyclo(fFfrRrQ) | 463 ± 94 |
| 274 | cyclo(fFfRrRQ) | 359 ± 66 |
| 275 | cyclo(FfFrRrQ) | 236 ± 26 |
| 276 | cyclo(fFφrRrQ) | 250 ± 37 |
| 277 | cyclo(FΦfrRrQ) | 267 ± 62 |
| 278 | cyclo(φFfrRrQ) | 50 ± 9 |
| 279 | cyclo(FΦrRrQ) | 76 |
| 280 | cyclo(fΦrRrQ) | 214 |
| 281 | Ac-(Lys-fFRrRrD) | 129 ± 9 |
| 282 | Ac-(Dap-fFRrRrD) | 126 ± 33 |
| 283 | CWWRRRRC<br>S—S | 51 |
| 284 | CWWWRRRRC<br>S—S | 67 |
| 285 | CFWRRRRC<br>S—S | 49 |
| 286 | CWWWRRRC<br>S—S | 135 |

[a]underlined portion only.
[b]Φ = L-2-naphthylalanine;
φ = D-2-naphthylalanine;
f = D-phenylalanine;
r = D-arginine;
X = L-4-fluorophenylalanine;
Dap = L-2,3-diaminopropionic acid.
[c]All values are relative to that of CPP 1 (100%) and represent the mean S.D. of three independent experiments.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

SEQUENCE LISTING

```
Sequence total quantity: 286
SEQ ID NO: 1            moltype = AA  length = 5
FEATURE                 Location/Qualifiers
MOD_RES                 2
                        note = L-2-naphthylalanine
source                  1..5
                        mol_type = protein
                        organism = synthetic construct
SEQUENCE: 1
FXRRR                                                                5

SEQ ID NO: 2            moltype = AA  length = 6
FEATURE                 Location/Qualifiers
MOD_RES                 2
                        note = L-2-naphthylalanine
source                  1..6
                        mol_type = protein
                        organism = synthetic construct
SEQUENCE: 2
FXRRRC                                                               6

SEQ ID NO: 3            moltype = AA  length = 6
FEATURE                 Location/Qualifiers
MOD_RES                 2
                        note = L-2-naphthylalanine
source                  1..6
                        mol_type = protein
                        organism = synthetic construct
SEQUENCE: 3
FXRRRU                                                               6

SEQ ID NO: 4            moltype = AA  length = 5
FEATURE                 Location/Qualifiers
MOD_RES                 4
                        note = L-2-naphthylalanine
source                  1..5
                        mol_type = protein
                        organism = synthetic construct
SEQUENCE: 4
RRRXF                                                                5

SEQ ID NO: 5            moltype = AA  length = 6
FEATURE                 Location/Qualifiers
MOD_RES                 5
                        note = L-2-naphthylalanine
source                  1..6
                        mol_type = protein
                        organism = synthetic construct
SEQUENCE: 5
RRRRXF                                                               6

SEQ ID NO: 6            moltype = AA  length = 6
FEATURE                 Location/Qualifiers
MOD_RES                 2
                        note = L-2-naphthylalanine
source                  1..6
                        mol_type = protein
                        organism = synthetic construct
SEQUENCE: 6
FXRRRR                                                               6

SEQ ID NO: 7            moltype = AA  length = 6
FEATURE                 Location/Qualifiers
MOD_RES                 2
                        note = D-2-naphthylalanine
MOD_RES                 3
                        note = D-amino acid
MOD_RES                 5
                        note = D-amino acid
source                  1..6
                        mol_type = protein
                        organism = synthetic construct
SEQUENCE: 7
FXRRRR                                                               6

SEQ ID NO: 8            moltype = AA  length = 6
FEATURE                 Location/Qualifiers
MOD_RES                 2
```

-continued

```
                    note = D-2-naphthylalanine
MOD_RES             3
                    note = D-amino acid
MOD_RES             5
                    note = D-amino acid
source              1..6
                    mol_type = protein
                    organism = synthetic construct
SEQUENCE: 8
FXRRRR                                                    6

SEQ ID NO: 9        moltype = AA  length = 6
FEATURE             Location/Qualifiers
MOD_RES             2
                    note = L-2-naphthylalanine
source              1..6
                    mol_type = protein
                    organism = synthetic construct
SEQUENCE: 9
FXRRRR                                                    6

SEQ ID NO: 10       moltype = AA  length = 6
FEATURE             Location/Qualifiers
MOD_RES             1
                    note = D-amino acid
MOD_RES             2
                    note = L-2-naphthylalanine
MOD_RES             4
                    note = D-amino acid
MOD_RES             6
                    note = D-amino acid
source              1..6
                    mol_type = protein
                    organism = synthetic construct
SEQUENCE: 10
FXRRRR                                                    6

SEQ ID NO: 11       moltype = AA  length = 6
FEATURE             Location/Qualifiers
MOD_RES             5
                    note = L-2-naphthylalanine
source              1..6
                    mol_type = protein
                    organism = synthetic construct
SEQUENCE: 11
RRFRXR                                                    6

SEQ ID NO: 12       moltype = AA  length = 6
FEATURE             Location/Qualifiers
MOD_RES             6
                    note = L-2-naphthylalanine
source              1..6
                    mol_type = protein
                    organism = synthetic construct
SEQUENCE: 12
FRRRRX                                                    6

SEQ ID NO: 13       moltype = AA  length = 6
FEATURE             Location/Qualifiers
MOD_RES             1
                    note = D-amino acid
MOD_RES             5
                    note = L-2-naphthylalanine
source              1..6
                    mol_type = protein
                    organism = synthetic construct
SEQUENCE: 13
RRFRXR                                                    6

SEQ ID NO: 14       moltype = AA  length = 6
FEATURE             Location/Qualifiers
MOD_RES             3
                    note = L-2-naphthylalanine
source              1..6
                    mol_type = protein
                    organism = synthetic construct
SEQUENCE: 14
RRXFRR                                                    6
```

-continued

```
SEQ ID NO: 15           moltype = AA  length = 7
FEATURE                 Location/Qualifiers
source                  1..7
                        mol_type = protein
                        organism = synthetic construct
SEQUENCE: 15
CRRRRFW                                                                      7

SEQ ID NO: 16           moltype = AA  length = 7
FEATURE                 Location/Qualifiers
MOD_RES                 2
                        note = D-amino acid
MOD_RES                 3
                        note = L-2-naphthylalanine
MOD_RES                 5
                        note = D-amino acid
MOD_RES                 7
                        note = D-amino acid
source                  1..7
                        mol_type = protein
                        organism = synthetic construct
SEQUENCE: 16
FFXRRRR                                                                      7

SEQ ID NO: 17           moltype = AA  length = 7
FEATURE                 Location/Qualifiers
MOD_RES                 3
                        note = L-2-naphthylalanine
source                  1..7
                        mol_type = protein
                        organism = synthetic construct
SEQUENCE: 17
FFXRRRR                                                                      7

SEQ ID NO: 18           moltype = AA  length = 7
FEATURE                 Location/Qualifiers
REGION                  1..7
                        note = Synthetic Construct
MOD_RES                 6
                        note = L-2-naphthylalanine
source                  1..7
                        mol_type = protein
                        organism = synthetic construct
SEQUENCE: 18
RFRFRXR                                                                      7

SEQ ID NO: 19           moltype = AA  length = 7
FEATURE                 Location/Qualifiers
source                  1..7
                        mol_type = protein
                        organism = synthetic construct
SEQUENCE: 19
URRRRFW                                                                      7

SEQ ID NO: 20           moltype = AA  length = 7
FEATURE                 Location/Qualifiers
source                  1..7
                        mol_type = protein
                        organism = synthetic construct
SEQUENCE: 20
CRRRRFW                                                                      7

SEQ ID NO: 21           moltype = AA  length = 8
FEATURE                 Location/Qualifiers
MOD_RES                 2
                        note = L-2-naphthylalanine
source                  1..8
                        mol_type = protein
                        organism = synthetic construct
SEQUENCE: 21
FXRRRRQK                                                                     8

SEQ ID NO: 22           moltype = AA  length = 8
FEATURE                 Location/Qualifiers
MOD_RES                 2
                        note = L-2-naphthylalanine
source                  1..8
                        mol_type = protein
                        organism = synthetic construct
```

-continued

```
SEQUENCE: 22
FXRRRRQC                                                 8

SEQ ID NO: 23           moltype = AA  length = 7
FEATURE                 Location/Qualifiers
MOD_RES                 1
                        note = D-amino acid
MOD_RES                 2
                        note = L-2-naphthylalanine
MOD_RES                 4
                        note = D-amino acid
MOD_RES                 6
                        note = D-amino acid
source                  1..7
                        mol_type = protein
                        organism = synthetic construct
SEQUENCE: 23
FXRRRRR                                                  7

SEQ ID NO: 24           moltype = AA  length = 7
FEATURE                 Location/Qualifiers
MOD_RES                 2
                        note = L-2-naphthylalanine
source                  1..7
                        mol_type = protein
                        organism = synthetic construct
SEQUENCE: 24
FXRRRRR                                                  7

SEQ ID NO: 25           moltype = AA  length = 9
FEATURE                 Location/Qualifiers
MOD_RES                 5
                        note = L-2-naphthylalanine
MOD_RES                 8
                        note = Nle
source                  1..9
                        mol_type = protein
                        organism = synthetic construct
SEQUENCE: 25
RRRRXFDXC                                                9

SEQ ID NO: 26           moltype = AA  length = 5
FEATURE                 Location/Qualifiers
MOD_RES                 2
                        note = L-2-naphthylalanine
source                  1..5
                        mol_type = protein
                        organism = synthetic construct
SEQUENCE: 26
FXRRR                                                    5

SEQ ID NO: 27           moltype = AA  length = 5
FEATURE                 Location/Qualifiers
source                  1..5
                        mol_type = protein
                        organism = synthetic construct
SEQUENCE: 27
FWRRR                                                    5

SEQ ID NO: 28           moltype = AA  length = 5
FEATURE                 Location/Qualifiers
MOD_RES                 4
                        note = L-2-naphthylalanine
source                  1..5
                        mol_type = protein
                        organism = synthetic construct
SEQUENCE: 28
RRRXF                                                    5

SEQ ID NO: 29           moltype = AA  length = 5
FEATURE                 Location/Qualifiers
source                  1..5
                        mol_type = protein
                        organism = synthetic construct
SEQUENCE: 29
RRRWF                                                    5

SEQ ID NO: 30           moltype = AA  length = 6
FEATURE                 Location/Qualifiers
```

-continued

```
MOD_RES                 2
                        note = L-2-naphthylalanine
source                  1..6
                        mol_type = protein
                        organism = synthetic construct
SEQUENCE: 30
FXRRRR                                                      6

SEQ ID NO: 31           moltype = AA  length = 5
FEATURE                 Location/Qualifiers
source                  1..5
                        mol_type = protein
                        organism = synthetic construct
SEQUENCE: 31
FFRRR                                                       5

SEQ ID NO: 32           moltype = AA  length = 5
FEATURE                 Location/Qualifiers
MOD_RES                 3
                        note = D-amino acid
MOD_RES                 5
                        note = D-amino acid
source                  1..5
                        mol_type = protein
                        organism = synthetic construct
SEQUENCE: 32
FFRRR                                                       5

SEQ ID NO: 33           moltype = AA  length = 5
FEATURE                 Location/Qualifiers
MOD_RES                 4
                        note = D-amino acid
source                  1..5
                        mol_type = protein
                        organism = synthetic construct
SEQUENCE: 33
FFRRR                                                       5

SEQ ID NO: 34           moltype = AA  length = 5
FEATURE                 Location/Qualifiers
source                  1..5
                        mol_type = protein
                        organism = synthetic construct
SEQUENCE: 34
FRFRR                                                       5

SEQ ID NO: 35           moltype = AA  length = 5
FEATURE                 Location/Qualifiers
source                  1..5
                        mol_type = protein
                        organism = synthetic construct
SEQUENCE: 35
FRRFR                                                       5

SEQ ID NO: 36           moltype = AA  length = 5
FEATURE                 Location/Qualifiers
source                  1..5
                        mol_type = protein
                        organism = synthetic construct
SEQUENCE: 36
FRRRF                                                       5

SEQ ID NO: 37           moltype = AA  length = 5
FEATURE                 Location/Qualifiers
MOD_RES                 2
                        note = L-2-naphthylalanine
source                  1..5
                        mol_type = protein
                        organism = synthetic construct
SEQUENCE: 37
GXRRR                                                       5

SEQ ID NO: 38           moltype = AA  length = 5
FEATURE                 Location/Qualifiers
source                  1..5
                        mol_type = protein
                        organism = synthetic construct
SEQUENCE: 38
FFFRA                                                       5
```

-continued

```
SEQ ID NO: 39          moltype = AA  length = 5
FEATURE                Location/Qualifiers
source                 1..5
                       mol_type = protein
                       organism = synthetic construct
SEQUENCE: 39
FFFRR                                                          5

SEQ ID NO: 40          moltype = AA  length = 6
FEATURE                Location/Qualifiers
source                 1..6
                       mol_type = protein
                       organism = synthetic construct
SEQUENCE: 40
FFRRRR                                                         6

SEQ ID NO: 41          moltype = AA  length = 6
FEATURE                Location/Qualifiers
source                 1..6
                       mol_type = protein
                       organism = synthetic construct
SEQUENCE: 41
FRRFRR                                                         6

SEQ ID NO: 42          moltype = AA  length = 6
FEATURE                Location/Qualifiers
source                 1..6
                       mol_type = protein
                       organism = synthetic construct
SEQUENCE: 42
FRRRFR                                                         6

SEQ ID NO: 43          moltype = AA  length = 6
FEATURE                Location/Qualifiers
source                 1..6
                       mol_type = protein
                       organism = synthetic construct
SEQUENCE: 43
RFFRRR                                                         6

SEQ ID NO: 44          moltype = AA  length = 6
FEATURE                Location/Qualifiers
source                 1..6
                       mol_type = protein
                       organism = synthetic construct
SEQUENCE: 44
RFRRFR                                                         6

SEQ ID NO: 45          moltype = AA  length = 6
FEATURE                Location/Qualifiers
source                 1..6
                       mol_type = protein
                       organism = synthetic construct
SEQUENCE: 45
FRFRRR                                                         6

SEQ ID NO: 46          moltype = AA  length = 6
FEATURE                Location/Qualifiers
source                 1..6
                       mol_type = protein
                       organism = synthetic construct
SEQUENCE: 46
FFFRRR                                                         6

SEQ ID NO: 47          moltype = AA  length = 6
FEATURE                Location/Qualifiers
source                 1..6
                       mol_type = protein
                       organism = synthetic construct
SEQUENCE: 47
FFRRRF                                                         6

SEQ ID NO: 48          moltype = AA  length = 6
FEATURE                Location/Qualifiers
source                 1..6
                       mol_type = protein
                       organism = synthetic construct
SEQUENCE: 48
```

-continued

```
FRFFRR                                                                  6

SEQ ID NO: 49            moltype = AA  length = 6
FEATURE                  Location/Qualifiers
source                   1..6
                         mol_type = protein
                         organism = synthetic construct
SEQUENCE: 49
RRFFFR                                                                  6

SEQ ID NO: 50            moltype = AA  length = 6
FEATURE                  Location/Qualifiers
source                   1..6
                         mol_type = protein
                         organism = synthetic construct
SEQUENCE: 50
FFRFRR                                                                  6

SEQ ID NO: 51            moltype = AA  length = 6
FEATURE                  Location/Qualifiers
source                   1..6
                         mol_type = protein
                         organism = synthetic construct
SEQUENCE: 51
FFRRFR                                                                  6

SEQ ID NO: 52            moltype = AA  length = 6
FEATURE                  Location/Qualifiers
source                   1..6
                         mol_type = protein
                         organism = synthetic construct
SEQUENCE: 52
FRRFFR                                                                  6

SEQ ID NO: 53            moltype = AA  length = 6
FEATURE                  Location/Qualifiers
source                   1..6
                         mol_type = protein
                         organism = synthetic construct
SEQUENCE: 53
FRRFRF                                                                  6

SEQ ID NO: 54            moltype = AA  length = 6
FEATURE                  Location/Qualifiers
source                   1..6
                         mol_type = protein
                         organism = synthetic construct
SEQUENCE: 54
FRFRFR                                                                  6

SEQ ID NO: 55            moltype = AA  length = 6
FEATURE                  Location/Qualifiers
source                   1..6
                         mol_type = protein
                         organism = synthetic construct
SEQUENCE: 55
RFFRFR                                                                  6

SEQ ID NO: 56            moltype = AA  length = 6
FEATURE                  Location/Qualifiers
MOD_RES                  2
                         note = L-2-naphthylalanine
source                   1..6
                         mol_type = protein
                         organism = synthetic construct
SEQUENCE: 56
GXRRRR                                                                  6

SEQ ID NO: 57            moltype = AA  length = 7
FEATURE                  Location/Qualifiers
source                   1..7
                         mol_type = protein
                         organism = synthetic construct
SEQUENCE: 57
FFFRRRR                                                                 7

SEQ ID NO: 58            moltype = AA  length = 7
FEATURE                  Location/Qualifiers
source                   1..7
```

```
                        mol_type = protein
                        organism = synthetic construct
SEQUENCE: 58
RFFRRRR                                                         7

SEQ ID NO: 59           moltype = AA  length = 7
FEATURE                 Location/Qualifiers
source                  1..7
                        mol_type = protein
                        organism = synthetic construct
SEQUENCE: 59
RRFFRRR                                                         7

SEQ ID NO: 60           moltype = AA  length = 7
FEATURE                 Location/Qualifiers
source                  1..7
                        mol_type = protein
                        organism = synthetic construct
SEQUENCE: 60
RFFFRRR                                                         7

SEQ ID NO: 61           moltype = AA  length = 7
FEATURE                 Location/Qualifiers
source                  1..7
                        mol_type = protein
                        organism = synthetic construct
SEQUENCE: 61
RRFFFRR                                                         7

SEQ ID NO: 62           moltype = AA  length = 7
FEATURE                 Location/Qualifiers
source                  1..7
                        mol_type = protein
                        organism = synthetic construct
SEQUENCE: 62
FFRRFRR                                                         7

SEQ ID NO: 63           moltype = AA  length = 7
FEATURE                 Location/Qualifiers
source                  1..7
                        mol_type = protein
                        organism = synthetic construct
SEQUENCE: 63
FFRRRRF                                                         7

SEQ ID NO: 64           moltype = AA  length = 7
FEATURE                 Location/Qualifiers
source                  1..7
                        mol_type = protein
                        organism = synthetic construct
SEQUENCE: 64
FRRFFRR                                                         7

SEQ ID NO: 65           moltype = AA  length = 8
FEATURE                 Location/Qualifiers
source                  1..8
                        mol_type = protein
                        organism = synthetic construct
SEQUENCE: 65
FFFRRRRR                                                        8

SEQ ID NO: 66           moltype = AA  length = 9
FEATURE                 Location/Qualifiers
source                  1..9
                        mol_type = protein
                        organism = synthetic construct
SEQUENCE: 66
FFFRRRRRR                                                       9

SEQ ID NO: 67           moltype = AA  length = 6
FEATURE                 Location/Qualifiers
MOD_RES                 2
                        note = L-2-naphthylalanine
MOD_RES                 4
                        note = D-amino acid
MOD_RES                 6
                        note = D-amino acid
source                  1..6
                        mol_type = protein
```

-continued

```
                        organism = synthetic construct
SEQUENCE: 67
FXRRRR                                                                      6

SEQ ID NO: 68           moltype = AA  length = 6
FEATURE                 Location/Qualifiers
MOD_RES                 1..2
                        note = L-4-fluorophenylalanine
source                  1..6
                        mol_type = protein
                        organism = synthetic construct
SEQUENCE: 68
XXRRRR                                                                      6

SEQ ID NO: 69           moltype = AA  length = 6
FEATURE                 Location/Qualifiers
MOD_RES                 2
                        note = D-amino acid
MOD_RES                 5
                        note = D-amino acid
source                  1..6
                        mol_type = protein
                        organism = synthetic construct
SEQUENCE: 69
FFFRRR                                                                      6

SEQ ID NO: 70           moltype = AA  length = 6
FEATURE                 Location/Qualifiers
MOD_RES                 1
                        note = D-amino acid
MOD_RES                 3..4
                        note = D-amino acid
MOD_RES                 6
                        note = D-amino acid
source                  1..6
                        mol_type = protein
                        organism = synthetic construct
SEQUENCE: 70
FFFRRR                                                                      6

SEQ ID NO: 71           moltype = AA  length = 6
FEATURE                 Location/Qualifiers
MOD_RES                 1
                        note = D-amino acid
MOD_RES                 3
                        note = D-amino acid
MOD_RES                 5
                        note = D-amino acid
source                  1..6
                        mol_type = protein
                        organism = synthetic construct
SEQUENCE: 71
FFFRRR                                                                      6

SEQ ID NO: 72           moltype = AA  length = 6
FEATURE                 Location/Qualifiers
MOD_RES                 2
                        note = D-amino acid
MOD_RES                 4
                        note = D-amino acid
MOD_RES                 6
                        note = D-amino acid
source                  1..6
                        mol_type = protein
                        organism = synthetic construct
SEQUENCE: 72
FFFRRR                                                                      6

SEQ ID NO: 73           moltype = AA  length = 6
FEATURE                 Location/Qualifiers
MOD_RES                 1
                        note = D-amino acid
MOD_RES                 3
                        note = D-2-naphthylalanine
MOD_RES                 4
                        note = D-amino acid
MOD_RES                 6
                        note = D-amino acid
source                  1..6
```

-continued

```
                        mol_type = protein
                        organism = synthetic construct
SEQUENCE: 73
FFXRRR                                                          6

SEQ ID NO: 74           moltype = AA  length = 6
FEATURE                 Location/Qualifiers
MOD_RES                 1
                        note = D-amino acid
MOD_RES                 2
                        note = L-2-naphthylalanine
MOD_RES                 3..4
                        note = D-amino acid
MOD_RES                 6
                        note = D-amino acid
source                  1..6
                        mol_type = protein
                        organism = synthetic construct
SEQUENCE: 74
FXFRRR                                                          6

SEQ ID NO: 75           moltype = AA  length = 6
FEATURE                 Location/Qualifiers
MOD_RES                 1
                        note = D-2-naphthylalanine
MOD_RES                 3..4
                        note = D-amino acid
MOD_RES                 6
                        note = D-amino acid
source                  1..6
                        mol_type = protein
                        organism = synthetic construct
SEQUENCE: 75
XFFRRR                                                          6

SEQ ID NO: 76           moltype = AA  length = 5
FEATURE                 Location/Qualifiers
MOD_RES                 2
                        note = L-2-naphthylalanine
MOD_RES                 3
                        note = D-amino acid
MOD_RES                 5
                        note = D-amino acid
source                  1..5
                        mol_type = protein
                        organism = synthetic construct
SEQUENCE: 76
FXRRR                                                           5

SEQ ID NO: 77           moltype = AA  length = 5
FEATURE                 Location/Qualifiers
MOD_RES                 1
                        note = D-amino acid
MOD_RES                 2
                        note = L-2-naphthylalanine
MOD_RES                 3
                        note = D-amino acid
MOD_RES                 5
                        note = D-amino acid
source                  1..5
                        mol_type = protein
                        organism = synthetic construct
SEQUENCE: 77
FXRRR                                                           5

SEQ ID NO: 78           moltype = AA  length = 8
FEATURE                 Location/Qualifiers
MOD_RES                 1
                        note = N-terminal acetylation
MOD_RES                 2
                        note = D-amino acid
MOD_RES                 5
                        note = D-amino acid
MOD_RES                 7
                        note = D-amino acid
source                  1..8
                        mol_type = protein
                        organism = synthetic construct
SEQUENCE: 78
```

```
KFFRRRRD                                                           8

SEQ ID NO: 79          moltype = AA  length = 8
FEATURE                Location/Qualifiers
MOD_RES                1
                       note = N-terminal acetylation
MOD_RES                1
                       note = Dpr
MOD_RES                2
                       note = D-amino acid
MOD_RES                5
                       note = D-amino acid
MOD_RES                7
                       note = D-amino acid
source                 1..8
                       mol_type = protein
                       organism = synthetic construct
SEQUENCE: 79
XFFRRRRD                                                           8

SEQ ID NO: 80          moltype = AA  length = 5
FEATURE                Location/Qualifiers
source                 1..5
                       mol_type = protein
                       organism = synthetic construct
SEQUENCE: 80
RRRRR                                                              5

SEQ ID NO: 81          moltype = AA  length = 5
FEATURE                Location/Qualifiers
source                 1..5
                       mol_type = protein
                       organism = synthetic construct
SEQUENCE: 81
AAAAA                                                              5

SEQ ID NO: 82          moltype = AA  length = 4
FEATURE                Location/Qualifiers
source                 1..4
                       mol_type = protein
                       organism = synthetic construct
SEQUENCE: 82
FFFF                                                               4

SEQ ID NO: 83          moltype = AA  length = 5
FEATURE                Location/Qualifiers
MOD_RES                3
                       note = phosphocoumaryl amino propionic acid
source                 1..5
                       mol_type = protein
                       organism = synthetic construct
SEQUENCE: 83
DEXLI                                                              5

SEQ ID NO: 84          moltype = AA  length = 7
FEATURE                Location/Qualifiers
source                 1..7
                       mol_type = protein
                       organism = synthetic construct
SEQUENCE: 84
AAAAAAA                                                            7

SEQ ID NO: 85          moltype = AA  length = 5
FEATURE                Location/Qualifiers
source                 1..5
                       mol_type = protein
                       organism = synthetic construct
SEQUENCE: 85
RARAR                                                              5

SEQ ID NO: 86          moltype = AA  length = 5
FEATURE                Location/Qualifiers
source                 1..5
                       mol_type = protein
                       organism = synthetic construct
SEQUENCE: 86
DADAD                                                              5

SEQ ID NO: 87          moltype =   length =
```

-continued

```
SEQUENCE: 87
000

SEQ ID NO: 88           moltype =   length =
SEQUENCE: 88
000

SEQ ID NO: 89           moltype = AA  length = 6
FEATURE                 Location/Qualifiers
MOD_RES                 2
                        note = L-homoproline
MOD_RES                 4
                        note = L-4-(phosphonodifluoromethyl)phenylalanine
source                  1..6
                        mol_type = protein
                        organism = synthetic construct
SEQUENCE: 89
PXGXYR                                                                      6

SEQ ID NO: 90           moltype =   length =
SEQUENCE: 90
000

SEQ ID NO: 91           moltype = AA  length = 6
FEATURE                 Location/Qualifiers
MOD_RES                 4
                        note = L-4-(phosphonodifluoromethyl)phenylalanine
source                  1..6
                        mol_type = protein
                        organism = synthetic construct
SEQUENCE: 91
IHIXIR                                                                      6

SEQ ID NO: 92           moltype = AA  length = 6
FEATURE                 Location/Qualifiers
MOD_RES                 2
                        note = D-amino acid
MOD_RES                 4
                        note = L-4-(phosphonodifluoromethyl)phenylalanine
MOD_RES                 5
                        note = L-homoproline
source                  1..6
                        mol_type = protein
                        organism = synthetic construct
SEQUENCE: 92
AAIXXR                                                                      6

SEQ ID NO: 93           moltype =   length =
SEQUENCE: 93
000

SEQ ID NO: 94           moltype = AA  length = 6
FEATURE                 Location/Qualifiers
MOD_RES                 1
                        note = L-homoproline
MOD_RES                 2
                        note = D-amino acid
MOD_RES                 4
                        note = L-4-(phosphonodifluoromethyl)phenylalanine
source                  1..6
                        mol_type = protein
                        organism = synthetic construct
SEQUENCE: 94
XNPXAR                                                                      6

SEQ ID NO: 95           moltype = AA  length = 6
FEATURE                 Location/Qualifiers
MOD_RES                 2
                        note = L-phenylglycine
MOD_RES                 4
                        note = L-4-(phosphonodifluoromethyl)phenylalanine
source                  1..6
                        mol_type = protein
                        organism = synthetic construct
SEQUENCE: 95
TXAXGR                                                                      6

SEQ ID NO: 96           moltype = AA  length = 6
FEATURE                 Location/Qualifiers
```

```
MOD_RES                 4
                        note = L-4-(phosphonodifluoromethyl)phenylalanine
MOD_RES                 5
                        note = D-amino acid
source                  1..6
                        mol_type = protein
                        organism = synthetic construct
SEQUENCE: 96
AHIXAR                                                                      6

SEQ ID NO: 97           moltype = AA  length = 6
FEATURE                 Location/Qualifiers
MOD_RES                 2
                        note = D-amino acid
MOD_RES                 4
                        note = L-4-(phosphonodifluoromethyl)phenylalanine
MOD_RES                 5
                        note = D-amino acid
source                  1..6
                        mol_type = protein
                        organism = synthetic construct
SEQUENCE: 97
GNGXPR                                                                      6

SEQ ID NO: 98           moltype = AA  length = 6
FEATURE                 Location/Qualifiers
MOD_RES                 1
                        note = D-amino acid
MOD_RES                 3
                        note = L-homoproline
MOD_RES                 4
                        note = L-4-(phosphonodifluoromethyl)phenylalanine
source                  1..6
                        mol_type = protein
                        organism = synthetic construct
SEQUENCE: 98
FQXXIR                                                                      6

SEQ ID NO: 99           moltype = AA  length = 6
FEATURE                 Location/Qualifiers
MOD_RES                 4
                        note = L-4-(phosphonodifluoromethyl)phenylalanine
source                  1..6
                        mol_type = protein
                        organism = synthetic construct
SEQUENCE: 99
SPGXHR                                                                      6

SEQ ID NO: 100          moltype = AA  length = 6
FEATURE                 Location/Qualifiers
MOD_RES                 1
                        note = L-homoproline
MOD_RES                 4
                        note = L-4-(phosphonodifluoromethyl)phenylalanine
source                  1..6
                        mol_type = protein
                        organism = synthetic construct
SEQUENCE: 100
XYIXHR                                                                      6

SEQ ID NO: 101          moltype = AA  length = 6
FEATURE                 Location/Qualifiers
MOD_RES                 2
                        note = D-amino acid
MOD_RES                 4
                        note = L-4-(phosphonodifluoromethyl)phenylalanine
source                  1..6
                        mol_type = protein
                        organism = synthetic construct
SEQUENCE: 101
SVPXHR                                                                      6

SEQ ID NO: 102          moltype = AA  length = 6
FEATURE                 Location/Qualifiers
MOD_RES                 4
                        note = L-4-(phosphonodifluoromethyl)phenylalanine
MOD_RES                 5
                        note = D-amino acid
source                  1..6
```

-continued

```
                        mol_type = protein
                        organism = synthetic construct
SEQUENCE: 102
AIPXNR                                                                      6

SEQ ID NO: 103          moltype = AA  length = 6
FEATURE                 Location/Qualifiers
MOD_RES                 1
                        note = L-4-fluorophenylalanine
MOD_RES                 4
                        note = L-4-(phosphonodifluoromethyl)phenylalanine
source                  1..6
                        mol_type = protein
                        organism = synthetic construct
SEQUENCE: 103
XSIXQF                                                                      6

SEQ ID NO: 104          moltype = AA  length = 6
FEATURE                 Location/Qualifiers
MOD_RES                 2
                        note = D-amino acid
MOD_RES                 3
                        note = L-phenylglycine
MOD_RES                 4
                        note = L-4-(phosphonodifluoromethyl)phenylalanine
MOD_RES                 5
                        note = D-amino acid
source                  1..6
                        mol_type = protein
                        organism = synthetic construct
SEQUENCE: 104
AAXXFR                                                                      6

SEQ ID NO: 105          moltype =   length =
SEQUENCE: 105
000

SEQ ID NO: 106          moltype =   length =
SEQUENCE: 106
000

SEQ ID NO: 107          moltype =   length =
SEQUENCE: 107
000

SEQ ID NO: 108          moltype = AA  length = 6
FEATURE                 Location/Qualifiers
MOD_RES                 1
                        note = D-amino acid
MOD_RES                 3
                        note = L-4-fluorophenylalanine
MOD_RES                 4
                        note = L-4-(phosphonodifluoromethyl)phenylalanine
source                  1..6
                        mol_type = protein
                        organism = synthetic construct
SEQUENCE: 108
NAXXGR                                                                      6

SEQ ID NO: 109          moltype = AA  length = 6
FEATURE                 Location/Qualifiers
MOD_RES                 1..2
                        note = D-amino acid
MOD_RES                 4
                        note = L-4-(phosphonodifluoromethyl)phenylalanine
source                  1..6
                        mol_type = protein
                        organism = synthetic construct
SEQUENCE: 109
NTYXAR                                                                      6

SEQ ID NO: 110          moltype = AA  length = 6
FEATURE                 Location/Qualifiers
MOD_RES                 1
                        note = D-amino acid
MOD_RES                 3
                        note = L-phenylglycine
MOD_RES                 4
                        note = L-4-(phosphonodifluoromethyl)phenylalanine
```

```
MOD_RES               5
                      note = D-amino acid
source                1..6
                      mol_type = protein
                      organism = synthetic construct
SEQUENCE: 110
EAXXVR                                                      6

SEQ ID NO: 111        moltype = AA  length = 6
FEATURE               Location/Qualifiers
MOD_RES               2
                      note = D-amino acid
MOD_RES               3
                      note = L-phenylglycine
MOD_RES               4
                      note = L-4-(phosphonodifluoromethyl)phenylalanine
source                1..6
                      mol_type = protein
                      organism = synthetic construct
SEQUENCE: 111
IVXXAR                                                      6

SEQ ID NO: 112        moltype = AA  length = 6
FEATURE               Location/Qualifiers
MOD_RES               2
                      note = D-amino acid
MOD_RES               3
                      note = L-phenylglycine
MOD_RES               4
                      note = L-4-(phosphonodifluoromethyl)phenylalanine
source                1..6
                      mol_type = protein
                      organism = synthetic construct
SEQUENCE: 112
YTXXAR                                                      6

SEQ ID NO: 113        moltype =   length =
SEQUENCE: 113
000

SEQ ID NO: 114        moltype = AA  length = 6
FEATURE               Location/Qualifiers
MOD_RES               1
                      note = L-homoproline
MOD_RES               2
                      note = D-amino acid
MOD_RES               4
                      note = L-4-(phosphonodifluoromethyl)phenylalanine
source                1..6
                      mol_type = protein
                      organism = synthetic construct
SEQUENCE: 114
XNWXHR                                                      6

SEQ ID NO: 115        moltype = AA  length = 6
FEATURE               Location/Qualifiers
MOD_RES               2
                      note = L-homoproline
MOD_RES               3
                      note = D-amino acid
MOD_RES               4
                      note = L-4-(phosphonodifluoromethyl)phenylalanine
source                1..6
                      mol_type = protein
                      organism = synthetic construct
SEQUENCE: 115
YXVXIR                                                      6

SEQ ID NO: 116        moltype = AA  length = 6
FEATURE               Location/Qualifiers
MOD_RES               1
                      note = D-amino acid
MOD_RES               3
                      note = D-amino acid
MOD_RES               4
                      note = L-4-(phosphonodifluoromethyl)phenylalanine
source                1..6
                      mol_type = protein
                      organism = synthetic construct
```

```
SEQUENCE: 116
NSAXGR                                                                    6

SEQ ID NO: 117          moltype = AA  length = 6
FEATURE                 Location/Qualifiers
MOD_RES                 1..3
                        note = D-amino acid
MOD_RES                 4
                        note = L-4-(phosphonodifluoromethyl)phenylalanine
MOD_RES                 5
                        note = D-amino acid
source                  1..6
                        mol_type = protein
                        organism = synthetic construct
SEQUENCE: 117
TNVXAR                                                                    6

SEQ ID NO: 118          moltype = AA  length = 6
FEATURE                 Location/Qualifiers
MOD_RES                 1..3
                        note = D-amino acid
MOD_RES                 4
                        note = L-4-(phosphonodifluoromethyl)phenylalanine
MOD_RES                 5
                        note = D-amino acid
source                  1..6
                        mol_type = protein
                        organism = synthetic construct
SEQUENCE: 118
NTVXTR                                                                    6

SEQ ID NO: 119          moltype = AA  length = 6
FEATURE                 Location/Qualifiers
MOD_RES                 3
                        note = D-amino acid
MOD_RES                 4
                        note = L-4-(phosphonodifluoromethyl)phenylalanine
MOD_RES                 5
                        note = D-amino acid
source                  1..6
                        mol_type = protein
                        organism = synthetic construct
SEQUENCE: 119
SITXYR                                                                    6

SEQ ID NO: 120          moltype = AA  length = 6
FEATURE                 Location/Qualifiers
MOD_RES                 1
                        note = D-amino acid
MOD_RES                 2
                        note = L-4-fluorophenylalanine
MOD_RES                 3
                        note = D-amino acid
MOD_RES                 4
                        note = L-4-(phosphonodifluoromethyl)phenylalanine
MOD_RES                 5
                        note = D-amino acid
source                  1..6
                        mol_type = protein
                        organism = synthetic construct
SEQUENCE: 120
NXNXLR                                                                    6

SEQ ID NO: 121          moltype = AA  length = 6
FEATURE                 Location/Qualifiers
MOD_RES                 2..3
                        note = D-amino acid
MOD_RES                 4
                        note = L-4-(phosphonodifluoromethyl)phenylalanine
MOD_RES                 5
                        note = Nle
source                  1..6
                        mol_type = protein
                        organism = synthetic construct
SEQUENCE: 121
YNNXXR                                                                    6

SEQ ID NO: 122          moltype = AA  length = 6
FEATURE                 Location/Qualifiers
```

-continued

```
MOD_RES                 1
                        note = D-amino acid
MOD_RES                 3
                        note = D-amino acid
MOD_RES                 4
                        note = L-4-(phosphonodifluoromethyl)phenylalanine
source                  1..6
                        mol_type = protein
                        organism = synthetic construct
SEQUENCE: 122
NYNXGR                                                                      6

SEQ ID NO: 123          moltype = AA  length = 6
FEATURE                 Location/Qualifiers
MOD_RES                 3
                        note = D-amino acid
MOD_RES                 4
                        note = L-4-(phosphonodifluoromethyl)phenylalanine
source                  1..6
                        mol_type = protein
                        organism = synthetic construct
SEQUENCE: 123
AWNXAR                                                                      6

SEQ ID NO: 124          moltype = AA  length = 6
FEATURE                 Location/Qualifiers
MOD_RES                 1..2
                        note = D-amino acid
MOD_RES                 4
                        note = L-4-(phosphonodifluoromethyl)phenylalanine
source                  1..6
                        mol_type = protein
                        organism = synthetic construct
SEQUENCE: 124
VTHXYR                                                                      6

SEQ ID NO: 125          moltype =   length =
SEQUENCE: 125
000

SEQ ID NO: 126          moltype = AA  length = 6
FEATURE                 Location/Qualifiers
MOD_RES                 1
                        note = D-amino acid
MOD_RES                 2
                        note = L-phenylglycine
MOD_RES                 4
                        note = L-4-(phosphonodifluoromethyl)phenylalanine
source                  1..6
                        mol_type = protein
                        organism = synthetic construct
SEQUENCE: 126
NXHXGR                                                                      6

SEQ ID NO: 127          moltype = AA  length = 6
FEATURE                 Location/Qualifiers
MOD_RES                 4
                        note = L-4-(phosphonodifluoromethyl)phenylalanine
source                  1..6
                        mol_type = protein
                        organism = synthetic construct
SEQUENCE: 127
PAHXGR                                                                      6

SEQ ID NO: 128          moltype = AA  length = 6
FEATURE                 Location/Qualifiers
MOD_RES                 4
                        note = L-4-(phosphonodifluoromethyl)phenylalanine
source                  1..6
                        mol_type = protein
                        organism = synthetic construct
SEQUENCE: 128
AYHXIR                                                                      6

SEQ ID NO: 129          moltype = AA  length = 6
FEATURE                 Location/Qualifiers
MOD_RES                 1
                        note = D-amino acid
MOD_RES                 2
```

-continued

```
                        note = L-homoproline
MOD_RES                 3
                        note = D-amino acid
MOD_RES                 4
                        note = L-4-(phosphonodifluoromethyl)phenylalanine
source                  1..6
                        mol_type = protein
                        organism = synthetic construct
SEQUENCE: 129
NXEXYR                                                                     6

SEQ ID NO: 130          moltype = AA  length = 6
FEATURE                 Location/Qualifiers
MOD_RES                 1
                        note = D-amino acid
MOD_RES                 4
                        note = L-4-(phosphonodifluoromethyl)phenylalanine
MOD_RES                 5
                        note = D-amino acid
source                  1..6
                        mol_type = protein
                        organism = synthetic construct
SEQUENCE: 130
VSSXTR                                                                     6

SEQ ID NO: 131          moltype = AA  length = 7
FEATURE                 Location/Qualifiers
REGION                  1..7
                        note = peptide is circular
MOD_RES                 2
                        note = L-2-naphthylalanine
source                  1..7
                        mol_type = protein
                        organism = synthetic construct
SEQUENCE: 131
FXRRRRQ                                                                    7

SEQ ID NO: 132          moltype = AA  length = 9
FEATURE                 Location/Qualifiers
source                  1..9
                        mol_type = protein
                        organism = synthetic construct
SEQUENCE: 132
RRRRRRRRR                                                                  9

SEQ ID NO: 133          moltype = AA  length = 8
FEATURE                 Location/Qualifiers
MOD_RES                 1
                        note = D-amino acid
MOD_RES                 2
                        note = sarcosine
MOD_RES                 3
                        note = D-phosphothreonine
MOD_RES                 4
                        note = L-pipecolic acid
MOD_RES                 5
                        note = L-beta-naphthylalanine
source                  1..8
                        mol_type = protein
                        organism = synthetic construct
SEQUENCE: 133
AXXXXYQK                                                                   8

SEQ ID NO: 134          moltype =   length =
SEQUENCE: 134
000

SEQ ID NO: 135          moltype = AA  length = 9
FEATURE                 Location/Qualifiers
MOD_RES                 1
                        note = modified with trimesic acid
MOD_RES                 1
                        note = D-amino acid
MOD_RES                 2
                        note = sarcosine
MOD_RES                 3
                        note = D-phosphotheronine
MOD_RES                 4
                        note = L-pipecolic acid
```

```
MOD_RES                 5
                        note = L-beta-naphthylalanine
MOD_RES                 8
                        note = D-amino acid
MOD_RES                 9
                        note = Dpr
source                  1..9
                        mol_type = protein
                        organism = synthetic construct
SEQUENCE: 135
AXXXXRAAX                                                          9

SEQ ID NO: 136          moltype = AA  length = 9
FEATURE                 Location/Qualifiers
MOD_RES                 1
                        note = modified with trimesic acid
MOD_RES                 1
                        note = D-amino acid
MOD_RES                 2
                        note = sarcosine
MOD_RES                 3
                        note = D-amino acid
MOD_RES                 4
                        note = L-pipecolic acid
MOD_RES                 5
                        note = L-beta-naphthylalanine
MOD_RES                 8
                        note = D-amino acid
MOD_RES                 9
                        note = Dpr
source                  1..9
                        mol_type = protein
                        organism = synthetic construct
SEQUENCE: 136
AXXTXRAAX                                                          9

SEQ ID NO: 137          moltype = AA  length = 9
FEATURE                 Location/Qualifiers
MOD_RES                 1
                        note = modified with trimesic acid
MOD_RES                 1
                        note = D-amino acid
MOD_RES                 2
                        note = sarcosine
MOD_RES                 3..4
                        note = D-amino acid
MOD_RES                 5
                        note = L-beta-naphthylalanine
MOD_RES                 8
                        note = D-amino acid
MOD_RES                 9
                        note = Dpr
source                  1..9
                        mol_type = protein
                        organism = synthetic construct
SEQUENCE: 137
AXTAXRAAX                                                          9

SEQ ID NO: 138          moltype = AA  length = 6
FEATURE                 Location/Qualifiers
MOD_RES                 1
                        note = D-amino acid
source                  1..6
                        mol_type = protein
                        organism = synthetic construct
SEQUENCE: 138
ETGEFL                                                             6

SEQ ID NO: 139          moltype = AA  length = 7
FEATURE                 Location/Qualifiers
MOD_RES                 1
                        note = D-amino acid
source                  1..7
                        mol_type = protein
                        organism = synthetic construct
SEQUENCE: 139
LDPETGE                                                            7

SEQ ID NO: 140          moltype = AA  length = 14
```

-continued

```
FEATURE               Location/Qualifiers
REGION                1..14
                      note = peptide is circular
MOD_RES               4
                      note = L-2-naphthylalanine
MOD_RES               6
                      note = D-amino acid
source                1..14
                      mol_type = protein
                      organism = synthetic construct
SEQUENCE: 140
AAFXRPPRRR AAAQ                                                    14

SEQ ID NO: 141        moltype = AA  length = 14
FEATURE               Location/Qualifiers
REGION                1..14
                      note = peptide is circular
MOD_RES               6
                      note = D-amino acid
MOD_RES               10
                      note = L-2-naphthylalanine
source                1..14
                      mol_type = protein
                      organism = synthetic construct
SEQUENCE: 141
AAFRRPPRRX AAAQ                                                    14

SEQ ID NO: 142        moltype = AA  length = 14
FEATURE               Location/Qualifiers
REGION                1..14
                      note = peptide is circular
MOD_RES               4
                      note = L-2-naphthylalanine
MOD_RES               6
                      note = D-amino acid
source                1..14
                      mol_type = protein
                      organism = synthetic construct
SEQUENCE: 142
AAFXFPPRRR AAAQ                                                    14

SEQ ID NO: 143        moltype = AA  length = 14
FEATURE               Location/Qualifiers
REGION                1..14
                      note = peptide is circular
MOD_RES               4
                      note = L-2-naphthylalanine
MOD_RES               6
                      note = D-amino acid
source                1..14
                      mol_type = protein
                      organism = synthetic construct
SEQUENCE: 143
AAFXRPPRRF AAAQ                                                    14

SEQ ID NO: 144        moltype = AA  length = 14
FEATURE               Location/Qualifiers
REGION                1..14
                      note = peptide is circular
MOD_RES               4
                      note = L-2-naphthylalanine
MOD_RES               6
                      note = D-amino acid
MOD_RES               8
                      note = D-amino acid
source                1..14
                      mol_type = protein
                      organism = synthetic construct
SEQUENCE: 144
AAFXRPPRRF AAAQ                                                    14

SEQ ID NO: 145        moltype = AA  length = 14
FEATURE               Location/Qualifiers
REGION                1..14
                      note = peptide is circular
MOD_RES               4
                      note = L-2-naphthylalanine
MOD_RES               5..6
                      note = D-amino acid
```

```
source                  1..14
                        mol_type = protein
                        organism = synthetic construct
SEQUENCE: 145
AAFXRPPRRF AAAQ                                                      14

SEQ ID NO: 146          moltype = AA  length = 14
FEATURE                 Location/Qualifiers
REGION                  1..14
                        note = peptide is circular
MOD_RES                 4
                        note = L-2-naphthylalanine
MOD_RES                 6
                        note = D-amino acid
MOD_RES                 9
                        note = D-amino acid
source                  1..14
                        mol_type = protein
                        organism = synthetic construct
SEQUENCE: 146
AAFXRPPRRF AAAQ                                                      14

SEQ ID NO: 147          moltype = AA  length = 14
FEATURE                 Location/Qualifiers
REGION                  1..14
                        note = peptide is circular
MOD_RES                 4
                        note = D-2-naphthylalanine
MOD_RES                 6
                        note = D-amino acid
source                  1..14
                        mol_type = protein
                        organism = synthetic construct
SEQUENCE: 147
AAFXRPPRRF AAAQ                                                      14

SEQ ID NO: 148          moltype = AA  length = 14
FEATURE                 Location/Qualifiers
REGION                  1..14
                        note = peptide is circular
MOD_RES                 4
                        note = L-2-naphthylalanine
MOD_RES                 5..6
                        note = D-amino acid
source                  1..14
                        mol_type = protein
                        organism = synthetic construct
SEQUENCE: 148
RAFXRPPRRF RARQ                                                      14

SEQ ID NO: 149          moltype = AA  length = 14
FEATURE                 Location/Qualifiers
REGION                  1..14
                        note = peptide is circular
MOD_RES                 4
                        note = L-2-naphthylalanine
MOD_RES                 5..6
                        note = D-amino acid
source                  1..14
                        mol_type = protein
                        organism = synthetic construct
SEQUENCE: 149
DAFXRPPRRF DADQ                                                      14

SEQ ID NO: 150          moltype = AA  length = 16
FEATURE                 Location/Qualifiers
REGION                  1..16
                        note = peptide is circular
SITE                    5
                        note = L-2-naphthylalanine
REGION                  6..7
                        note = D-amino acid
source                  1..16
                        mol_type = protein
                        organism = synthetic construct
SEQUENCE: 150
SASFXRPPRR FSASAQ                                                    16

SEQ ID NO: 151          moltype = AA  length = 17
```

-continued

```
FEATURE                 Location/Qualifiers
REGION                  1..17
                        note = peptide is circular
MOD_RES                 9
                        note = L-2-naphthylalanine
MOD_RES                 10..11
                        note = D-amino acid
source                  1..17
                        mol_type = protein
                        organism = synthetic construct
SEQUENCE: 151
AETGEFLFXR PPRRFLQ                                                    17

SEQ ID NO: 152          moltype = AA  length = 7
FEATURE                 Location/Qualifiers
REGION                  1..7
                        note = peptide is circular
MOD_RES                 2
                        note = L-2-naphthylalanine
source                  1..7
                        mol_type = protein
                        organism = synthetic construct
SEQUENCE: 152
FXRRRRQ                                                               7

SEQ ID NO: 153          moltype = AA  length = 6
FEATURE                 Location/Qualifiers
source                  1..6
                        mol_type = protein
                        organism = synthetic construct
SEQUENCE: 153
RARQRA                                                                6

SEQ ID NO: 154          moltype = AA  length = 6
FEATURE                 Location/Qualifiers
source                  1..6
                        mol_type = protein
                        organism = synthetic construct
SEQUENCE: 154
DADQDA                                                                6

SEQ ID NO: 155          moltype = AA  length = 10
FEATURE                 Location/Qualifiers
MOD_RES                 1
                        note = N-terminal acetylation
DISULFID                1..10
                        note = Intrachain via Cys-Cys
source                  1..10
                        mol_type = protein
                        organism = synthetic construct
SEQUENCE: 155
CTWEGNKLTC                                                            10

SEQ ID NO: 156          moltype = AA  length = 8
FEATURE                 Location/Qualifiers
source                  1..8
                        mol_type = protein
                        organism = synthetic construct
SEQUENCE: 156
SASAQSAS                                                              8

SEQ ID NO: 157          moltype = AA  length = 16
FEATURE                 Location/Qualifiers
source                  1..16
                        mol_type = protein
                        organism = synthetic construct
SEQUENCE: 157
AFFAQLQLDE ETGEFL                                                     16

SEQ ID NO: 158          moltype = AA  length = 4
FEATURE                 Location/Qualifiers
MOD_RES                 1
                        note = D-amino acid
source                  1..4
                        mol_type = protein
                        organism = synthetic construct
SEQUENCE: 158
ETGE                                                                  4
```

-continued

```
SEQ ID NO: 159         moltype = AA  length = 9
FEATURE                Location/Qualifiers
MOD_RES                1
                       note = D-amino acid
source                 1..9
                       mol_type = protein
                       organism = synthetic construct
SEQUENCE: 159
LDEETGEFL                                                      9

SEQ ID NO: 160         moltype = AA  length = 17
FEATURE                Location/Qualifiers
source                 1..17
                       mol_type = protein
                       organism = synthetic construct
SEQUENCE: 160
HAFFAQLQLD EETGEFL                                             17

SEQ ID NO: 161         moltype = AA  length = 17
FEATURE                Location/Qualifiers
REGION                 1..17
                       note = peptide is circular
MOD_RES                3
                       note = L-2-naphthylalanine
MOD_RES                4..5
                       note = D-amino acid
source                 1..17
                       mol_type = protein
                       organism = synthetic construct
SEQUENCE: 161
FFXRPPRRFQ LDPETGE                                             17

SEQ ID NO: 162         moltype = AA  length = 17
FEATURE                Location/Qualifiers
REGION                 1..17
                       note = peptide is circular
MOD_RES                3
                       note = L-2-naphthylalanine
MOD_RES                4..5
                       note = D-amino acid
source                 1..17
                       mol_type = protein
                       organism = synthetic construct
SEQUENCE: 162
FFXRPPRRFQ LNAETGE                                             17

SEQ ID NO: 163         moltype = AA  length = 16
FEATURE                Location/Qualifiers
REGION                 1..16
                       note = peptide is circular
MOD_RES                3
                       note = L-2-naphthylalanine
MOD_RES                4..5
                       note = D-amino acid
source                 1..16
                       mol_type = protein
                       organism = synthetic construct
SEQUENCE: 163
FFXRPPRRFL DPETGE                                              16

SEQ ID NO: 164         moltype = AA  length = 16
FEATURE                Location/Qualifiers
REGION                 1..16
                       note = peptide is circular
MOD_RES                3
                       note = L-2-naphthylalanine
MOD_RES                4..5
                       note = D-amino acid
source                 1..16
                       mol_type = protein
                       organism = synthetic construct
SEQUENCE: 164
FFXRPPRRFL NAETGE                                              16

SEQ ID NO: 165         moltype = AA  length = 15
FEATURE                Location/Qualifiers
REGION                 1..15
                       note = peptide is circular
MOD_RES                2
```

-continued

```
                        note = L-2-naphthylalanine
MOD_RES                 3..4
                        note = D-amino acid
source                  1..15
                        mol_type = protein
                        organism = synthetic construct
SEQUENCE: 165
FXRPPRRFLD PETGE                                                    15

SEQ ID NO: 166          moltype = AA  length = 15
FEATURE                 Location/Qualifiers
REGION                  1..15
                        note = peptide is circular
MOD_RES                 2
                        note = L-2-naphthylalanine
MOD_RES                 3..4
                        note = D-amino acid
source                  1..15
                        mol_type = protein
                        organism = synthetic construct
SEQUENCE: 166
FXRPPRRFLN AETGE                                                    15

SEQ ID NO: 167          moltype = AA  length = 14
FEATURE                 Location/Qualifiers
REGION                  1..14
                        note = peptide is circular
MOD_RES                 2
                        note = L-2-naphthylalanine
MOD_RES                 3..4
                        note = D-amino acid
source                  1..14
                        mol_type = protein
                        organism = synthetic construct
SEQUENCE: 167
FXRPPRRFNA ETGE                                                     14

SEQ ID NO: 168          moltype = AA  length = 17
FEATURE                 Location/Qualifiers
REGION                  1..17
                        note = peptide is circular
MOD_RES                 3
                        note = L-2-naphthylalanine
MOD_RES                 4..5
                        note = D-amino acid
MOD_RES                 11
                        note = modified with naphthofluorescein
source                  1..17
                        mol_type = protein
                        organism = synthetic construct
SEQUENCE: 168
FFXRPPRRFQ KDPETGE                                                  17

SEQ ID NO: 169          moltype = AA  length = 15
FEATURE                 Location/Qualifiers
REGION                  1..15
                        note = peptide is circular
MOD_RES                 2
                        note = L-2-naphthylalanine
MOD_RES                 3..4
                        note = D-amino acid
MOD_RES                 9
                        note = modified with naphthofluorescein
source                  1..15
                        mol_type = protein
                        organism = synthetic construct
SEQUENCE: 169
FXRPPRRFKD PETGE                                                    15

SEQ ID NO: 170          moltype = AA  length = 17
FEATURE                 Location/Qualifiers
REGION                  1..17
                        note = peptide is circular
MOD_RES                 3
                        note = L-2-naphthylalanine
MOD_RES                 4
                        note = D-amino acid
MOD_RES                 6
                        note = D-amino acid
```

```
MOD_RES              11
                     note = modified with naphthofluorescein
source               1..17
                     mol_type = protein
                     organism = synthetic construct
SEQUENCE: 170
FFXRPPRRFQ KDPETGE                                              17

SEQ ID NO: 171       moltype = AA  length = 7
FEATURE              Location/Qualifiers
REGION               1..7
                     note = peptide is circular
MOD_RES              2
                     note = L-2-naphthylalanine
source               1..7
                     mol_type = protein
                     organism = synthetic construct
SEQUENCE: 171
FXRRRRQ                                                         7

SEQ ID NO: 172       moltype = AA  length = 7
FEATURE              Location/Qualifiers
MOD_RES              1
                     note = L-homoproline
MOD_RES              2
                     note = L-2-naphthylalanine
MOD_RES              5..7
                     note = D-amino acid
source               1..7
                     mol_type = protein
                     organism = synthetic construct
SEQUENCE: 172
XXRERRE                                                         7

SEQ ID NO: 173       moltype = AA  length = 7
FEATURE              Location/Qualifiers
MOD_RES              1
                     note = L-homoproline
MOD_RES              2
                     note = L-2-naphthylalanine
MOD_RES              5..7
                     note = D-amino acid
source               1..7
                     mol_type = protein
                     organism = synthetic construct
SEQUENCE: 173
XXRRRRE                                                         7

SEQ ID NO: 174       moltype = AA  length = 7
FEATURE              Location/Qualifiers
MOD_RES              1
                     note = L-homoproline
MOD_RES              2..3
                     note = L-2-naphthylalanine
MOD_RES              5..7
                     note = D-amino acid
source               1..7
                     mol_type = protein
                     organism = synthetic construct
SEQUENCE: 174
XXXRRRE                                                         7

SEQ ID NO: 175       moltype = AA  length = 7
FEATURE              Location/Qualifiers
MOD_RES              1
                     note = L-homoproline
MOD_RES              2..3
                     note = L-2-naphthylalanine
MOD_RES              5..6
                     note = D-amino acid
source               1..7
                     mol_type = protein
                     organism = synthetic construct
SEQUENCE: 175
XXXRRRE                                                         7

SEQ ID NO: 176       moltype =   length =
SEQUENCE: 176
000
```

```
SEQ ID NO: 177          moltype =   length =
SEQUENCE: 177
000

SEQ ID NO: 178          moltype = AA  length = 7
FEATURE                 Location/Qualifiers
MOD_RES                 1
                        note = L-homoproline
MOD_RES                 2
                        note = L-2-naphthylalanine
MOD_RES                 5..7
                        note = D-amino acid
source                  1..7
                        mol_type = protein
                        organism = synthetic construct
SEQUENCE: 178
XXFRRRE                                                                      7

SEQ ID NO: 179          moltype = AA  length = 7
FEATURE                 Location/Qualifiers
MOD_RES                 1
                        note = L-homoproline
MOD_RES                 2
                        note = L-2-naphthylalanine
MOD_RES                 5..6
                        note = D-amino acid
source                  1..7
                        mol_type = protein
                        organism = synthetic construct
SEQUENCE: 179
XXFRRRE                                                                      7

SEQ ID NO: 180          moltype = AA  length = 7
FEATURE                 Location/Qualifiers
MOD_RES                 1
                        note = L-homoproline
MOD_RES                 2
                        note = L-2-naphthylalanine
MOD_RES                 3
                        note = D-amino acid
MOD_RES                 5..7
                        note = D-amino acid
source                  1..7
                        mol_type = protein
                        organism = synthetic construct
SEQUENCE: 180
XXFRRRE                                                                      7

SEQ ID NO: 181          moltype = AA  length = 7
FEATURE                 Location/Qualifiers
MOD_RES                 1
                        note = L-homoproline
MOD_RES                 2
                        note = L-2-naphthylalanine
MOD_RES                 3
                        note = D-amino acid
MOD_RES                 5..6
                        note = D-amino acid
source                  1..7
                        mol_type = protein
                        organism = synthetic construct
SEQUENCE: 181
XXFRRRE                                                                      7

SEQ ID NO: 182          moltype = AA  length = 7
FEATURE                 Location/Qualifiers
MOD_RES                 1
                        note = L-homoproline
MOD_RES                 2
                        note = L-2-naphthylalanine
MOD_RES                 3
                        note = D-2-naphthylalanine
MOD_RES                 5..6
                        note = D-amino acid
source                  1..7
                        mol_type = protein
                        organism = synthetic construct
SEQUENCE: 182
```

-continued

```
XXXRRRE                                                             7

SEQ ID NO: 183          moltype = AA  length = 7
FEATURE                 Location/Qualifiers
MOD_RES                 1
                        note = L-homoproline
MOD_RES                 2
                        note = L-2-naphthylalanine
MOD_RES                 3
                        note = D-2-naphthylalanine
MOD_RES                 5..7
                        note = D-amino acid
source                  1..7
                        mol_type = protein
                        organism = synthetic construct
SEQUENCE: 183
XXXRRRE                                                             7

SEQ ID NO: 184          moltype = AA  length = 10
FEATURE                 Location/Qualifiers
MOD_RES                 2
                        note = D-amino acid
MOD_RES                 3
                        note = D-amino acid
MOD_RES                 4
                        note = L-cyclohexylalanine
MOD_RES                 5
                        note = D-amino acid
MOD_RES                 6
                        note = L-cyclohexylalanine
MOD_RES                 7
                        note = D-amino acid
MOD_RES                 8
                        note = L-cyclohexylalanine
MOD_RES                 9
                        note = D-amino acid
source                  1..10
                        mol_type = protein
                        organism = synthetic construct
CROSSLNK                1..10
                        note = Macrocyclization by multicomponent reaction with
                         aziridine aldehyde and isocyanide
MOD_RES                 2
                        note = L-cyclohexylalanine
SEQUENCE: 184
PXRXRXRXRG                                                          10

SEQ ID NO: 185          moltype = AA  length = 13
FEATURE                 Location/Qualifiers
MOD_RES                 1
                        note = Ser is modified with trimesic acid
REGION                  1..13
                        note = N-terminal amine and side chains of two
                         L-2,3-diaminopropionic acid residues bicyclized with
                         trimesic acid
MOD_RES                 2
                        note = D-amino acid
MOD_RES                 4
                        note = L-difluorophosphonomethyl phenylalanine
MOD_RES                 6
                        note = L-2,3-diaminopropionic acid
MOD_RES                 8
                        note = L-naphthylalanine
MOD_RES                 13
                        note = L-2,3-diaminopropionic acid
source                  1..13
                        mol_type = protein
                        organism = synthetic construct
SEQUENCE: 185
SXPXHXFXRR RRX                                                      13

SEQ ID NO: 186          moltype = AA  length = 17
FEATURE                 Location/Qualifiers
MOD_RES                 1
                        note = modified with trimesic acid
MOD_RES                 1
                        note = D-amino acid
REGION                  1..17
                        note = MISC_FEATURE - N-terminal amine and side chains of
```

```
                         two L-2,3-diaminopropionic acid residues bicyclized with
                         trimesic acid
MOD_RES                 2
                        note = L-sarcosine
MOD_RES                 4
                        note = D-phosphothreonine
MOD_RES                 5
                        note = L-homoproline
MOD_RES                 6
                        note = L-naphthylalanine
MOD_RES                 9
                        note = D-amino acid
MOD_RES                 10
                        note = L-2,3-diaminopropionic acid
MOD_RES                 12
                        note = L-naphthylalanine
MOD_RES                 17
                        note = L-2,3-diaminopropionic acid
source                  1..17
                        mol_type = protein
                        organism = synthetic construct
SEQUENCE: 186
AXDXXXRAAX FXRRRRX                                                    17

SEQ ID NO: 187          moltype = AA  length = 16
FEATURE                 Location/Qualifiers
REGION                  1..15
                        note = Three Cys side chains bicyclized with
                         tris(bromomethyl)benzene
source                  1..16
                        mol_type = protein
                        organism = synthetic construct
SEQUENCE: 187
CRRSRRGCGR RSRRCG                                                     16

SEQ ID NO: 188          moltype = AA  length = 5
FEATURE                 Location/Qualifiers
REGION                  1..5
                        note = Synthetic Construct
REGION                  1..2
                        note = linked by dodecanoyl moiety
source                  1..5
                        mol_type = protein
                        organism = synthetic construct
SEQUENCE: 188
KRRRR                                                                 5

SEQ ID NO: 189          moltype = AA  length = 16
FEATURE                 Location/Qualifiers
source                  1..16
                        mol_type = protein
                        organism = synthetic construct
SEQUENCE: 189
LKKLCKLLKK LCKLAG                                                     16

SEQ ID NO: 190          moltype = AA  length = 9
FEATURE                 Location/Qualifiers
source                  1..9
                        mol_type = protein
                        organism = synthetic construct
CROSSLNK                5..9
                        note = Cyclization between Lys-Glu
SEQUENCE: 190
RRRRKRRRE                                                             9

SEQ ID NO: 191          moltype = AA  length = 9
FEATURE                 Location/Qualifiers
REGION                  1..9
                        note = Synthetic Construct
REGION                  4..9
                        note = Cyclization between Lys and Glu
source                  1..9
                        mol_type = protein
                        organism = synthetic construct
SEQUENCE: 191
RRRKRRRRE                                                             9

SEQ ID NO: 192          moltype = AA  length = 9
FEATURE                 Location/Qualifiers
```

```
source                  1..9
                        mol_type = protein
                        organism = synthetic construct
CROSSLNK                3..9
                        note = Cyclization between Lys-Glu
SEQUENCE: 192
RRKRRRRRE                                                          9

SEQ ID NO: 193          moltype = AA  length = 9
FEATURE                 Location/Qualifiers
source                  1..9
                        mol_type = protein
                        organism = synthetic construct
CROSSLNK                2..9
                        note = Cyclization between Lys-Glu
SEQUENCE: 193
RKRRRRRRE                                                          9

SEQ ID NO: 194          moltype = AA  length = 8
FEATURE                 Location/Qualifiers
source                  1..8
                        mol_type = protein
                        organism = synthetic construct
SEQUENCE: 194
CRCRCRCR                                                           8

SEQ ID NO: 195          moltype = AA  length = 12
FEATURE                 Location/Qualifiers
MOD_RES                 1
                        note = L-propargylglycine
MOD_RES                 12
                        note = L-6-Azido-2-amino-hexanoic
source                  1..12
                        mol_type = protein
                        organism = synthetic construct
CROSSLNK                1..12
                        note = Cyclization by the click reaction between
                         L-propargylglycine and L-6-Azido-2-amino-hexanoic
SEQUENCE: 195
XLRKRLRKFR NX                                                      12

SEQ ID NO: 196          moltype = AA  length = 9
FEATURE                 Location/Qualifiers
MOD_RES                 2..4
                        note = Dpr
MOD_RES                 5
                        note = D-amino acid
MOD_RES                 7..8
                        note = Dpr
source                  1..9
                        mol_type = protein
                        organism = synthetic construct
SEQUENCE: 196
TXXXFLXXT                                                          9

SEQ ID NO: 197          moltype = AA  length = 9
FEATURE                 Location/Qualifiers
MOD_RES                 2
                        note = L-2-amino-3-guanidinylpropionic acid
MOD_RES                 3
                        note = Dpr
MOD_RES                 4
                        note = L-2-amino-3-guanidinylpropionic acid
MOD_RES                 5
                        note = D-amino acid
MOD_RES                 7..8
                        note = L-2-amino-3-guanidinylpropionic acid
source                  1..9
                        mol_type = protein
                        organism = synthetic construct
SEQUENCE: 197
TXXXFLXXT                                                          9

SEQ ID NO: 198          moltype = AA  length = 7
FEATURE                 Location/Qualifiers
MOD_RES                 2
                        note = L-2-naphthylalanine
MOD_RES                 3
                        note = D-amino acid
```

```
source                  1..7
                        mol_type = protein
                        organism = synthetic construct
SEQUENCE: 198
FXPPRRR                                                                   7

SEQ ID NO: 199          moltype = AA  length = 8
FEATURE                 Location/Qualifiers
MOD_RES                 1
                        note = D-amino acid
MOD_RES                 3
                        note = D-2-naphthylalanine
MOD_RES                 4
                        note = D-amino acid
MOD_RES                 6
                        note = D-amino acid
MOD_RES                 8
                        note = D-amino acid
source                  1..8
                        mol_type = protein
                        organism = synthetic construct
SEQUENCE: 199
FFXPPRRR                                                                  8

SEQ ID NO: 200          moltype = AA  length = 8
FEATURE                 Location/Qualifiers
MOD_RES                 1
                        note = D-amino acid
MOD_RES                 2
                        note = L-2-naphthylalanine
MOD_RES                 3..4
                        note = D-amino acid
MOD_RES                 6
                        note = D-amino acid
MOD_RES                 8
                        note = D-amino acid
source                  1..8
                        mol_type = protein
                        organism = synthetic construct
SEQUENCE: 200
FXFPPRRR                                                                  8

SEQ ID NO: 201          moltype = AA  length = 8
FEATURE                 Location/Qualifiers
MOD_RES                 2
                        note = D-2-naphthylalanine
MOD_RES                 3
                        note = D-amino acid
MOD_RES                 5
                        note = D-amino acid
MOD_RES                 7
                        note = D-amino acid
source                  1..8
                        mol_type = protein
                        organism = synthetic construct
SEQUENCE: 201
FXPPRRRR                                                                  8

SEQ ID NO: 202          moltype = AA  length = 8
FEATURE                 Location/Qualifiers
MOD_RES                 2
                        note = D-2-naphthylalanine
MOD_RES                 3
                        note = D-amino acid
MOD_RES                 5
                        note = D-amino acid
MOD_RES                 7
                        note = D-amino acid
source                  1..8
                        mol_type = protein
                        organism = synthetic construct
SEQUENCE: 202
FXPPRRRR                                                                  8

SEQ ID NO: 203          moltype = AA  length = 8
FEATURE                 Location/Qualifiers
MOD_RES                 1
                        note = D-amino acid
MOD_RES                 2
```

```
                          note = L-2-naphthylalanine
MOD_RES                   3
                          note = D-amino acid
MOD_RES                   6
                          note = D-amino acid
MOD_RES                   8
                          note = D-amino acid
source                    1..8
                          mol_type = protein
                          organism = synthetic construct
SEQUENCE: 203
FXPPRRRR                                                                  8

SEQ ID NO: 204            moltype = AA  length = 7
FEATURE                   Location/Qualifiers
MOD_RES                   2
                          note = L-2-naphthylalanine
MOD_RES                   4
                          note = D-amino acid
source                    1..7
                          mol_type = protein
                          organism = synthetic construct
SEQUENCE: 204
FXPPRRR                                                                   7

SEQ ID NO: 205            moltype = AA  length = 8
FEATURE                   Location/Qualifiers
MOD_RES                   1
                          note = D-amino acid
MOD_RES                   3
                          note = D-2-naphthylalanine
MOD_RES                   5..6
                          note = D-amino acid
MOD_RES                   8
                          note = D-amino acid
source                    1..8
                          mol_type = protein
                          organism = synthetic construct
SEQUENCE: 205
FFXPPRRR                                                                  8

SEQ ID NO: 206            moltype = AA  length = 8
FEATURE                   Location/Qualifiers
MOD_RES                   1
                          note = D-amino acid
MOD_RES                   2
                          note = L-2-naphthylalanine
MOD_RES                   3
                          note = D-amino acid
MOD_RES                   5..6
                          note = D-amino acid
MOD_RES                   8
                          note = D-amino acid
source                    1..8
                          mol_type = protein
                          organism = synthetic construct
SEQUENCE: 206
FXFPPRRR                                                                  8

SEQ ID NO: 207            moltype = AA  length = 8
FEATURE                   Location/Qualifiers
MOD_RES                   2
                          note = D-2-naphthylalanine
MOD_RES                   4..5
                          note = D-amino acid
MOD_RES                   7
                          note = D-amino acid
source                    1..8
                          mol_type = protein
                          organism = synthetic construct
SEQUENCE: 207
FXPPRRRR                                                                  8

SEQ ID NO: 208            moltype = AA  length = 8
FEATURE                   Location/Qualifiers
MOD_RES                   2
                          note = D-2-naphthylalanine
MOD_RES                   4..5
                          note = D-amino acid
```

```
MOD_RES               7
                      note = D-amino acid
source                1..8
                      mol_type = protein
                      organism = synthetic construct
SEQUENCE: 208
FXPPRRRR                                                          8

SEQ ID NO: 209        moltype = AA  length = 8
FEATURE               Location/Qualifiers
MOD_RES               1
                      note = D-amino acid
MOD_RES               2
                      note = L-2-naphthylalanine
MOD_RES               4
                      note = D-amino acid
MOD_RES               6
                      note = D-amino acid
MOD_RES               8
                      note = D-amino acid
source                1..8
                      mol_type = protein
                      organism = synthetic construct
SEQUENCE: 209
FXPPRRRR                                                          8

SEQ ID NO: 210        moltype = AA  length = 7
FEATURE               Location/Qualifiers
MOD_RES               2
                      note = L-2-naphthylalanine
MOD_RES               4
                      note = D-amino acid
source                1..7
                      mol_type = protein
                      organism = synthetic construct
SEQUENCE: 210
FXRPPRR                                                           7

SEQ ID NO: 211        moltype = AA  length = 8
FEATURE               Location/Qualifiers
MOD_RES               1
                      note = D-amino acid
MOD_RES               3
                      note = D-amino acid
MOD_RES               4
                      note = D-2-naphthylalanine
MOD_RES               5
                      note = D-amino acid
MOD_RES               8
                      note = D-amino acid
source                1..8
                      mol_type = protein
                      organism = synthetic construct
SEQUENCE: 211
FFRXPPRR                                                          8

SEQ ID NO: 212        moltype = AA  length = 8
FEATURE               Location/Qualifiers
MOD_RES               1
                      note = D-amino acid
MOD_RES               2
                      note = L-2-naphthylalanine
MOD_RES               3..5
                      note = D-amino acid
MOD_RES               8
                      note = D-amino acid
source                1..8
                      mol_type = protein
                      organism = synthetic construct
SEQUENCE: 212
FXFRPPRR                                                          8

SEQ ID NO: 213        moltype = AA  length = 8
FEATURE               Location/Qualifiers
MOD_RES               2
                      note = D-2-naphthylalanine
MOD_RES               3..4
                      note = D-amino acid
MOD_RES               7
```

```
                        note = D-amino acid
source                  1..8
                        mol_type = protein
                        organism = synthetic construct
SEQUENCE: 213
FXRPPRRR                                                                    8

SEQ ID NO: 214          moltype = AA  length = 8
FEATURE                 Location/Qualifiers
MOD_RES                 2
                        note = D-2-naphthylalanine
MOD_RES                 3
                        note = D-amino acid
MOD_RES                 5
                        note = D-amino acid
MOD_RES                 7
                        note = D-amino acid
source                  1..8
                        mol_type = protein
                        organism = synthetic construct
SEQUENCE: 214
FXRRPPRR                                                                    8

SEQ ID NO: 215          moltype = AA  length = 8
FEATURE                 Location/Qualifiers
MOD_RES                 1
                        note = D-amino acid
MOD_RES                 2
                        note = L-2-naphthylalanine
MOD_RES                 4
                        note = D-amino acid
MOD_RES                 6
                        note = D-amino acid
MOD_RES                 8
                        note = D-amino acid
source                  1..8
                        mol_type = protein
                        organism = synthetic construct
SEQUENCE: 215
FXRPPRRR                                                                    8

SEQ ID NO: 216          moltype = AA  length = 7
FEATURE                 Location/Qualifiers
MOD_RES                 2
                        note = L-2-naphthylalanine
MOD_RES                 5
                        note = D-amino acid
source                  1..7
                        mol_type = protein
                        organism = synthetic construct
SEQUENCE: 216
FXRPPRR                                                                     7

SEQ ID NO: 217          moltype = AA  length = 8
FEATURE                 Location/Qualifiers
MOD_RES                 1
                        note = D-amino acid
MOD_RES                 3
                        note = D-2-naphthylalanine
MOD_RES                 4
                        note = D-amino acid
MOD_RES                 6
                        note = D-amino acid
MOD_RES                 8
                        note = D-amino acid
source                  1..8
                        mol_type = protein
                        organism = synthetic construct
SEQUENCE: 217
FFXRPPRR                                                                    8

SEQ ID NO: 218          moltype = AA  length = 8
FEATURE                 Location/Qualifiers
MOD_RES                 1
                        note = D-amino acid
MOD_RES                 2
                        note = L-2-naphthylalanine
MOD_RES                 5..6
                        note = D-amino acid
```

```
MOD_RES                 8
                        note = D-amino acid
source                  1..8
                        mol_type = protein
                        organism = synthetic construct
SEQUENCE: 218
FXFPPRRR                                                                8

SEQ ID NO: 219          moltype = AA  length = 8
FEATURE                 Location/Qualifiers
MOD_RES                 2
                        note = D-2-naphthylalanine
MOD_RES                 3
                        note = D-amino acid
MOD_RES                 5
                        note = D-amino acid
MOD_RES                 7
                        note = D-amino acid
source                  1..8
                        mol_type = protein
                        organism = synthetic construct
SEQUENCE: 219
FXRPPRRR                                                                8

SEQ ID NO: 220          moltype = AA  length = 8
FEATURE                 Location/Qualifiers
MOD_RES                 2
                        note = D-2-naphthylalanine
MOD_RES                 3
                        note = D-amino acid
MOD_RES                 5
                        note = D-amino acid
MOD_RES                 7
                        note = D-amino acid
source                  1..8
                        mol_type = protein
                        organism = synthetic construct
SEQUENCE: 220
FXRPPRRR                                                                8

SEQ ID NO: 221          moltype = AA  length = 8
FEATURE                 Location/Qualifiers
MOD_RES                 1
                        note = D-amino acid
MOD_RES                 2
                        note = L-2-naphthylalanine
MOD_RES                 5..6
                        note = D-amino acid
MOD_RES                 8
                        note = D-amino acid
source                  1..8
                        mol_type = protein
                        organism = synthetic construct
SEQUENCE: 221
FXRPPRRR                                                                8

SEQ ID NO: 222          moltype =   length =
SEQUENCE: 222
000

SEQ ID NO: 223          moltype = AA  length = 10
FEATURE                 Location/Qualifiers
MOD_RES                 1
                        note = PHOSPHORYLATION
MOD_RES                 5
                        note = L-2-naphthylalanine
MOD_RES                 6..7
                        note = D-amino acid
source                  1..10
                        mol_type = protein
                        organism = synthetic construct
SEQUENCE: 223
YVNFXRPPRR                                                              10

SEQ ID NO: 224          moltype = AA  length = 4
FEATURE                 Location/Qualifiers
MOD_RES                 1
                        note = PHOSPHORYLATION
source                  1..4
```

```
                        mol_type = protein
                        organism = synthetic construct
SEQUENCE: 224
YVNF                                                                4

SEQ ID NO: 225          moltype = AA  length = 7
FEATURE                 Location/Qualifiers
MOD_RES                 2
                        note = L-2-naphthylalanine
MOD_RES                 3..4
                        note = D-amino acid
source                  1..7
                        mol_type = protein
                        organism = synthetic construct
SEQUENCE: 225
FXRPPRR                                                             7

SEQ ID NO: 226          moltype = AA  length = 10
FEATURE                 Location/Qualifiers
MOD_RES                 3
                        note = PHOSPHORYLATION
MOD_RES                 9
                        note = beta-alanine
MOD_RES                 10
                        note = modified with fluorescein (FAM)
source                  1..10
                        mol_type = protein
                        organism = synthetic construct
SEQUENCE: 226
AAYVNFFQXK                                                          10

SEQ ID NO: 227          moltype = AA  length = 7
FEATURE                 Location/Qualifiers
MOD_RES                 1
                        note = D-amino acid
MOD_RES                 2
                        note = L-2-naphthylalanine
MOD_RES                 4
                        note = D-amino acid
MOD_RES                 6
                        note = D-amino acid
source                  1..7
                        mol_type = protein
                        organism = synthetic construct
SEQUENCE: 227
FXRRRRQ                                                             7

SEQ ID NO: 228          moltype = AA  length = 10
FEATURE                 Location/Qualifiers
MOD_RES                 2
                        note = L-2-naphthylalanine
MOD_RES                 3..4
                        note = D-amino acid
MOD_RES                 8
                        note = PHOSPHORYLATION
source                  1..10
                        mol_type = protein
                        organism = synthetic construct
SEQUENCE: 228
FXRPPRRYVN                                                          10

SEQ ID NO: 229          moltype = AA  length = 10
FEATURE                 Location/Qualifiers
MOD_RES                 2
                        note = L-2-naphthylalanine
MOD_RES                 3..4
                        note = D-amino acid
MOD_RES                 8
                        note = PHOSPHORYLATION
source                  1..10
                        mol_type = protein
                        organism = synthetic construct
SEQUENCE: 229
FXRPPRRYVN                                                          10

SEQ ID NO: 230          moltype = AA  length = 10
FEATURE                 Location/Qualifiers
MOD_RES                 3..4
                        note = D-amino acid
```

```
MOD_RES                 8
                        note = PHOSPHORYLATION
source                  1..10
                        mol_type = protein
                        organism = synthetic construct
SEQUENCE: 230
FAAPPRRYVN                                                          10

SEQ ID NO: 231          moltype = AA  length = 10
FEATURE                 Location/Qualifiers
MOD_RES                 2
                        note = L-2-naphthylalanine
MOD_RES                 3..4
                        note = D-amino acid
source                  1..10
                        mol_type = protein
                        organism = synthetic construct
SEQUENCE: 231
FXRPPRRFAA                                                          10

SEQ ID NO: 232          moltype = AA  length = 10
FEATURE                 Location/Qualifiers
MOD_RES                 3
                        note = L-2-naphthylalanine
MOD_RES                 4..5
                        note = D-amino acid
source                  1..10
                        mol_type = protein
                        organism = synthetic construct
SEQUENCE: 232
AFXRPPRRFQ                                                          10

SEQ ID NO: 233          moltype = AA  length = 10
FEATURE                 Location/Qualifiers
MOD_RES                 2
                        note = L-2-naphthylalanine
MOD_RES                 3..4
                        note = D-amino acid
source                  1..10
                        mol_type = protein
                        organism = synthetic construct
SEQUENCE: 233
FXRPPRRFAQ                                                          10

SEQ ID NO: 234          moltype = AA  length = 6
FEATURE                 Location/Qualifiers
source                  1..6
                        mol_type = protein
                        organism = synthetic construct
REGION                  1..6
                        note = peptide is circular
SEQUENCE: 234
FFRRRQ                                                              6

SEQ ID NO: 235          moltype = AA  length = 6
FEATURE                 Location/Qualifiers
REGION                  1..6
                        note = peptide is circular
MOD_RES                 3
                        note = D-amino acid
MOD_RES                 5
                        note = D-amino acid
source                  1..6
                        mol_type = protein
                        organism = synthetic construct
SEQUENCE: 235
FFRRRQ                                                              6

SEQ ID NO: 236          moltype = AA  length = 6
FEATURE                 Location/Qualifiers
REGION                  1..6
                        note = peptide is circular
MOD_RES                 4
                        note = D-amino acid
source                  1..6
                        mol_type = protein
                        organism = synthetic construct
SEQUENCE: 236
FFRRRQ                                                              6
```

-continued

```
SEQ ID NO: 237          moltype = AA  length = 6
FEATURE                 Location/Qualifiers
REGION                  1..6
                        note = peptide is circular
source                  1..6
                        mol_type = protein
                        organism = synthetic construct
SEQUENCE: 237
FRFRRQ                                                                    6

SEQ ID NO: 238          moltype = AA  length = 6
FEATURE                 Location/Qualifiers
REGION                  1..6
                        note = peptide is circular
source                  1..6
                        mol_type = protein
                        organism = synthetic construct
SEQUENCE: 238
FRRFRQ                                                                    6

SEQ ID NO: 239          moltype = AA  length = 6
FEATURE                 Location/Qualifiers
REGION                  1..6
                        note = peptide is circular
source                  1..6
                        mol_type = protein
                        organism = synthetic construct
SEQUENCE: 239
FRRRFQ                                                                    6

SEQ ID NO: 240          moltype = AA  length = 6
FEATURE                 Location/Qualifiers
REGION                  1..6
                        note = peptide is circular
MOD_RES                 2
                        note = L-2-naphthylalanine
source                  1..6
                        mol_type = protein
                        organism = synthetic construct
SEQUENCE: 240
GXRRRQ                                                                    6

SEQ ID NO: 241          moltype = AA  length = 6
FEATURE                 Location/Qualifiers
REGION                  1..6
                        note = peptide is circular
source                  1..6
                        mol_type = protein
                        organism = synthetic construct
SEQUENCE: 241
FFFRAQ                                                                    6

SEQ ID NO: 242          moltype = AA  length = 6
FEATURE                 Location/Qualifiers
REGION                  1..6
                        note = peptide is circular
source                  1..6
                        mol_type = protein
                        organism = synthetic construct
SEQUENCE: 242
FFFRRQ                                                                    6

SEQ ID NO: 243          moltype = AA  length = 7
FEATURE                 Location/Qualifiers
REGION                  1..7
                        note = peptide is circular
source                  1..7
                        mol_type = protein
                        organism = synthetic construct
SEQUENCE: 243
FFRRRRQ                                                                   7

SEQ ID NO: 244          moltype = AA  length = 7
FEATURE                 Location/Qualifiers
REGION                  1..7
                        note = peptide is circular
source                  1..7
                        mol_type = protein
```

```
                        organism = synthetic construct
SEQUENCE: 244
FRRFRRQ                                                                 7

SEQ ID NO: 245          moltype = AA  length = 7
FEATURE                 Location/Qualifiers
REGION                  1..7
                        note = peptide is circular
source                  1..7
                        mol_type = protein
                        organism = synthetic construct
SEQUENCE: 245
FRRRFRQ                                                                 7

SEQ ID NO: 246          moltype = AA  length = 7
FEATURE                 Location/Qualifiers
REGION                  1..7
                        note = peptide is circular
source                  1..7
                        mol_type = protein
                        organism = synthetic construct
SEQUENCE: 246
RFFRRRQ                                                                 7

SEQ ID NO: 247          moltype = AA  length = 7
FEATURE                 Location/Qualifiers
REGION                  1..7
                        note = peptide is circular
source                  1..7
                        mol_type = protein
                        organism = synthetic construct
SEQUENCE: 247
RFRRRFQ                                                                 7

SEQ ID NO: 248          moltype = AA  length = 7
FEATURE                 Location/Qualifiers
REGION                  1..7
                        note = peptide is circular
source                  1..7
                        mol_type = protein
                        organism = synthetic construct
SEQUENCE: 248
FRFRRRQ                                                                 7

SEQ ID NO: 249          moltype = AA  length = 7
FEATURE                 Location/Qualifiers
REGION                  1..7
                        note = peptide is circular
source                  1..7
                        mol_type = protein
                        organism = synthetic construct
SEQUENCE: 249
FFFRRRQ                                                                 7

SEQ ID NO: 250          moltype = AA  length = 7
FEATURE                 Location/Qualifiers
REGION                  1..7
                        note = peptide is circular
source                  1..7
                        mol_type = protein
                        organism = synthetic construct
SEQUENCE: 250
FFRRRFQ                                                                 7

SEQ ID NO: 251          moltype = AA  length = 7
FEATURE                 Location/Qualifiers
REGION                  1..7
                        note = peptide is circular
source                  1..7
                        mol_type = protein
                        organism = synthetic construct
SEQUENCE: 251
FRFFRRQ                                                                 7

SEQ ID NO: 252          moltype = AA  length = 7
FEATURE                 Location/Qualifiers
REGION                  1..7
                        note = peptide is circular
source                  1..7
```

```
                        mol_type = protein
                        organism = synthetic construct
SEQUENCE: 252
RRFFFRQ                                                                     7

SEQ ID NO: 253          moltype = AA  length = 7
FEATURE                 Location/Qualifiers
REGION                  1..7
                        note = peptide is circular
source                  1..7
                        mol_type = protein
                        organism = synthetic construct
SEQUENCE: 253
FFRFRRQ                                                                     7

SEQ ID NO: 254          moltype = AA  length = 7
FEATURE                 Location/Qualifiers
REGION                  1..7
                        note = peptide is circular
source                  1..7
                        mol_type = protein
                        organism = synthetic construct
SEQUENCE: 254
FFRRFRQ                                                                     7

SEQ ID NO: 255          moltype = AA  length = 7
FEATURE                 Location/Qualifiers
REGION                  1..7
                        note = peptide is circular
source                  1..7
                        mol_type = protein
                        organism = synthetic construct
SEQUENCE: 255
FRRFFRQ                                                                     7

SEQ ID NO: 256          moltype = AA  length = 7
FEATURE                 Location/Qualifiers
REGION                  1..7
                        note = peptide is circular
source                  1..7
                        mol_type = protein
                        organism = synthetic construct
SEQUENCE: 256
FRRFRFQ                                                                     7

SEQ ID NO: 257          moltype = AA  length = 7
FEATURE                 Location/Qualifiers
REGION                  1..7
                        note = peptide is circular
source                  1..7
                        mol_type = protein
                        organism = synthetic construct
SEQUENCE: 257
FRFRFRQ                                                                     7

SEQ ID NO: 258          moltype = AA  length = 7
FEATURE                 Location/Qualifiers
REGION                  1..7
                        note = peptide is circular
source                  1..7
                        mol_type = protein
                        organism = synthetic construct
SEQUENCE: 258
RFFRFRQ                                                                     7

SEQ ID NO: 259          moltype = AA  length = 7
FEATURE                 Location/Qualifiers
REGION                  1..7
                        note = peptide is circular
MOD_RES                 2
                        note = L-2-naphthylalanine
source                  1..7
                        mol_type = protein
                        organism = synthetic construct
SEQUENCE: 259
GXRRRRQ                                                                     7

SEQ ID NO: 260          moltype = AA  length = 8
FEATURE                 Location/Qualifiers
```

```
REGION               1..8
                     note = peptide is circular
source               1..8
                     mol_type = protein
                     organism = synthetic construct
SEQUENCE: 260
FFFRRRRQ                                                            8

SEQ ID NO: 261       moltype = AA  length = 8
FEATURE              Location/Qualifiers
REGION               1..8
                     note = peptide is circular
source               1..8
                     mol_type = protein
                     organism = synthetic construct
SEQUENCE: 261
RFFRRRRQ                                                            8

SEQ ID NO: 262       moltype = AA  length = 8
FEATURE              Location/Qualifiers
REGION               1..8
                     note = peptide is circular
source               1..8
                     mol_type = protein
                     organism = synthetic construct
SEQUENCE: 262
RRFFRRRQ                                                            8

SEQ ID NO: 263       moltype = AA  length = 8
FEATURE              Location/Qualifiers
REGION               1..8
                     note = peptide is circular
source               1..8
                     mol_type = protein
                     organism = synthetic construct
SEQUENCE: 263
RFFFRRRQ                                                            8

SEQ ID NO: 264       moltype = AA  length = 8
FEATURE              Location/Qualifiers
REGION               1..8
                     note = peptide is circular
source               1..8
                     mol_type = protein
                     organism = synthetic construct
SEQUENCE: 264
RRFFFRRQ                                                            8

SEQ ID NO: 265       moltype = AA  length = 8
FEATURE              Location/Qualifiers
REGION               1..8
                     note = peptide is circular
source               1..8
                     mol_type = protein
                     organism = synthetic construct
SEQUENCE: 265
FFRRFRRQ                                                            8

SEQ ID NO: 266       moltype = AA  length = 8
FEATURE              Location/Qualifiers
REGION               1..8
                     note = peptide is circular
source               1..8
                     mol_type = protein
                     organism = synthetic construct
SEQUENCE: 266
FFRRRRFQ                                                            8

SEQ ID NO: 267       moltype = AA  length = 8
FEATURE              Location/Qualifiers
REGION               1..8
                     note = peptide is circular
source               1..8
                     mol_type = protein
                     organism = synthetic construct
SEQUENCE: 267
FRRFFRRQ                                                            8

SEQ ID NO: 268       moltype = AA  length = 9
```

-continued

| | | |
|---|---|---|
| FEATURE | Location/Qualifiers | |
| REGION | 1..9 | |
| | note = peptide is circular | |
| source | 1..9 | |
| | mol_type = protein | |
| | organism = synthetic construct | |
| SEQUENCE: 268 | | |
| FFFRRRRRQ | | 9 |
| | | |
| SEQ ID NO: 269 | moltype = AA length = 10 | |
| FEATURE | Location/Qualifiers | |
| REGION | 1..10 | |
| | note = peptide is circular | |
| source | 1..10 | |
| | mol_type = protein | |
| | organism = synthetic construct | |
| SEQUENCE: 269 | | |
| FFFRRRRRRQ | | 10 |
| | | |
| SEQ ID NO: 270 | moltype = AA length = 7 | |
| FEATURE | Location/Qualifiers | |
| REGION | 1..7 | |
| | note = peptide is circular | |
| MOD_RES | 2 | |
| | note = L-2-naphthylalanine | |
| MOD_RES | 4 | |
| | note = D-amino acid | |
| MOD_RES | 6 | |
| | note = D-amino acid | |
| source | 1..7 | |
| | mol_type = protein | |
| | organism = synthetic construct | |
| SEQUENCE: 270 | | |
| FXRRRRQ | | 7 |
| | | |
| SEQ ID NO: 271 | moltype = AA length = 7 | |
| FEATURE | Location/Qualifiers | |
| REGION | 1..7 | |
| | note = peptide is circular | |
| MOD_RES | 1..2 | |
| | note = L-4-fluorophenylalanine | |
| source | 1..7 | |
| | mol_type = protein | |
| | organism = synthetic construct | |
| SEQUENCE: 271 | | |
| XXRRRRQ | | 7 |
| | | |
| SEQ ID NO: 272 | moltype = AA length = 7 | |
| FEATURE | Location/Qualifiers | |
| REGION | 1..7 | |
| | note = peptide is circular | |
| MOD_RES | 2 | |
| | note = D-amino acid | |
| MOD_RES | 5 | |
| | note = D-amino acid | |
| source | 1..7 | |
| | mol_type = protein | |
| | organism = synthetic construct | |
| SEQUENCE: 272 | | |
| FFFRRRQ | | 7 |
| | | |
| SEQ ID NO: 273 | moltype = AA length = 7 | |
| FEATURE | Location/Qualifiers | |
| REGION | 1..7 | |
| | note = peptide is circular | |
| MOD_RES | 1 | |
| | note = D-amino acid | |
| MOD_RES | 3..4 | |
| | note = D-amino acid | |
| MOD_RES | 6 | |
| | note = D-amino acid | |
| source | 1..7 | |
| | mol_type = protein | |
| | organism = synthetic construct | |
| SEQUENCE: 273 | | |
| FFFRRRQ | | 7 |
| | | |
| SEQ ID NO: 274 | moltype = AA length = 7 | |
| FEATURE | Location/Qualifiers | |

```
REGION               1..7
                     note = peptide is circular
MOD_RES              1
                     note = D-amino acid
MOD_RES              3
                     note = D-amino acid
MOD_RES              5
                     note = D-amino acid
source               1..7
                     mol_type = protein
                     organism = synthetic construct
SEQUENCE: 274
FFFRRRQ                                                                  7

SEQ ID NO: 275       moltype = AA  length = 7
FEATURE              Location/Qualifiers
REGION               1..7
                     note = peptide is circular
MOD_RES              2
                     note = D-amino acid
MOD_RES              4
                     note = D-amino acid
MOD_RES              6
                     note = D-amino acid
source               1..7
                     mol_type = protein
                     organism = synthetic construct
SEQUENCE: 275
FFFRRRQ                                                                  7

SEQ ID NO: 276       moltype = AA  length = 7
FEATURE              Location/Qualifiers
REGION               1..7
                     note = peptide is circular
MOD_RES              1
                     note = D-amino acid
MOD_RES              3
                     note = D-2-naphthylalanine
MOD_RES              4
                     note = D-amino acid
MOD_RES              6
                     note = D-amino acid
source               1..7
                     mol_type = protein
                     organism = synthetic construct
SEQUENCE: 276
FFXRRRQ                                                                  7

SEQ ID NO: 277       moltype = AA  length = 7
FEATURE              Location/Qualifiers
REGION               1..7
                     note = peptide is circular
MOD_RES              1
                     note = D-amino acid
MOD_RES              2
                     note = L-2-naphthylalanine
MOD_RES              3..4
                     note = D-amino acid
MOD_RES              6
                     note = D-amino acid
source               1..7
                     mol_type = protein
                     organism = synthetic construct
SEQUENCE: 277
FXFRRRQ                                                                  7

SEQ ID NO: 278       moltype = AA  length = 7
FEATURE              Location/Qualifiers
REGION               1..7
                     note = peptide is circular
MOD_RES              1
                     note = D-2-naphthylalanine
MOD_RES              3..4
                     note = D-amino acid
MOD_RES              6
                     note = D-amino acid
source               1..7
                     mol_type = protein
                     organism = synthetic construct
```

```
SEQUENCE: 278
XFFRRRQ                                                                 7

SEQ ID NO: 279         moltype = AA  length = 6
FEATURE                Location/Qualifiers
REGION                 1..6
                       note = peptide is circular
MOD_RES                2
                       note = L-2-naphthylalanine
MOD_RES                3
                       note = D-amino acid
MOD_RES                5
                       note = D-amino acid
source                 1..6
                       mol_type = protein
                       organism = synthetic construct
SEQUENCE: 279
FXRRRQ                                                                  6

SEQ ID NO: 280         moltype = AA  length = 6
FEATURE                Location/Qualifiers
REGION                 1..6
                       note = peptide is circular
MOD_RES                1
                       note = D-amino acid
MOD_RES                2
                       note = L-2-naphthylalanine
MOD_RES                3
                       note = D-amino acid
MOD_RES                5
                       note = D-amino acid
source                 1..6
                       mol_type = protein
                       organism = synthetic construct
SEQUENCE: 280
FXRRRQ                                                                  6

SEQ ID NO: 281         moltype = AA  length = 8
FEATURE                Location/Qualifiers
MOD_RES                1
                       note = ACETYLATION
MOD_RES                2
                       note = D-amino acid
MOD_RES                5
                       note = D-amino acid
MOD_RES                7
                       note = D-amino acid
source                 1..8
                       mol_type = protein
                       organism = synthetic construct
SEQUENCE: 281
KFFRRRRD                                                                8

SEQ ID NO: 282         moltype = AA  length = 8
FEATURE                Location/Qualifiers
MOD_RES                1
                       note = ACETYLATION
MOD_RES                1
                       note = Dpr
MOD_RES                2
                       note = D-amino acid
MOD_RES                5
                       note = D-amino acid
MOD_RES                7
                       note = D-amino acid
source                 1..8
                       mol_type = protein
                       organism = synthetic construct
SEQUENCE: 282
XFFRRRRD                                                                8

SEQ ID NO: 283         moltype = AA  length = 8
FEATURE                Location/Qualifiers
DISULFID               1..8
                       note = Intrachain via Cys-Cys
source                 1..8
                       mol_type = protein
                       organism = synthetic construct
SEQUENCE: 283
```

-continued

```
CWWRRRRC                                                          8

SEQ ID NO: 284          moltype = AA  length = 9
FEATURE                 Location/Qualifiers
DISULFID                1..9
                        note = Intrachain via Cys-Cys
source                  1..9
                        mol_type = protein
                        organism = synthetic construct
SEQUENCE: 284
CWWWRRRRC                                                         9

SEQ ID NO: 285          moltype = AA  length = 8
FEATURE                 Location/Qualifiers
DISULFID                1..8
                        note = Intrachain via Cys-Cys
source                  1..8
                        mol_type = protein
                        organism = synthetic construct
SEQUENCE: 285
CFWRRRRC                                                          8

SEQ ID NO: 286          moltype = AA  length = 8
FEATURE                 Location/Qualifiers
DISULFID                1..8
                        note = Intrachain via Cys-Cys
source                  1..8
                        mol_type = protein
                        organism = synthetic construct
SEQUENCE: 286
CWWWRRRC                                                          8
```

We claim:

1. A compound comprising;

i. a cyclic cell penetrating 8 amino acid peptide, wherein the amino acids are connected through peptide bonds, that contains;

a. one arginine within two amino acids of another arginine;

b. a phenylalanine within two amino acids of another phenylalanine; and ii. an exocyclic cargo moiety conjugated to a side chain of the cell penetrating peptide wherein the conjugation is through glutamine and wherein the cargo comprises an amino acid sequence that targets an enzyme.

2. The compound of claim 1, wherein the cargo moiety also comprises a therapeutic moiety and a linker moiety.

3. The compound of claim 1, wherein the cargo moiety also comprises a therapeutic moiety and a linker moiety.

4. The compound of claim 1, wherein the cargo moiety also comprises one or more detectable moieties or one or more therapeutic moieties or any combination thereof.

5. The compound of claim 1, wherein the cyclic cell penetrating peptide comprises at least three amino acids with a hydrophobic side chain.

6. The compound of claim 5, wherein at least one of the amino acids with a hydrophobic side chain is a glycine.

7. The compound of claim 1, wherein the cyclic cell penetrating peptide comprises at least three amino acids which have a hydrophobic side chain, wherein at least two amino acids having a hydrophobic side chain are consecutive.

8. The compound of claim 7, wherein at least one of the amino acids with a hydrophobic side chain is a glycine.

9. The compound of claim 1, wherein the cyclic cell penetrating peptide comprises at least two consecutive L amino acids.

10. The compound of claim 1, wherein each amino acid of the cyclic cell penetrating peptide is a natural amino acid.

* * * * *